United States Patent
Patel et al.

(10) Patent No.: US 10,857,187 B2
(45) Date of Patent: Dec. 8, 2020

(54) EXOSOMES FROM HUMAN ADIPOSE-DERIVED STEM CELLS FOR THE TREATMENT OF BRAIN INJURY

(71) Applicants: Niketa A. Patel, Land O Lakes, FL (US); Paula Cole Bickford, Ruskin, FL (US)

(72) Inventors: Niketa A. Patel, Land O Lakes, FL (US); Paula Cole Bickford, Ruskin, FL (US)

(73) Assignee: University of South Florida, Tampa, FL (US)

( * ) Notice: Subject to any disclaimer, the term of this patent is extended or adjusted under 35 U.S.C. 154(b) by 0 days.

(21) Appl. No.: 16/011,239

(22) Filed: Jun. 18, 2018

(65) Prior Publication Data

US 2018/0360888 A1    Dec. 20, 2018

Related U.S. Application Data

(60) Provisional application No. 62/520,684, filed on Jun. 16, 2017.

(51) Int. Cl.
| | | |
|---|---|---|
| A61K 48/00 | (2006.01) | |
| C12N 5/02 | (2006.01) | |
| C07H 21/02 | (2006.01) | |
| A61K 35/35 | (2015.01) | |
| A61K 38/28 | (2006.01) | |
| A61K 35/28 | (2015.01) | |

(52) U.S. Cl.
CPC .............. *A61K 35/35* (2013.01); *A61K 38/28* (2013.01); *A61K 35/28* (2013.01); *A61K 48/00* (2013.01); *C07H 21/02* (2013.01)

(58) Field of Classification Search
CPC ........ A61K 35/28; A61K 35/35; A61K 38/28; A61K 48/00; C07H 21/02
USPC ......................... 435/391; 514/44 R; 536/23.1
See application file for complete search history.

(56) References Cited

FOREIGN PATENT DOCUMENTS

EP    2756847    7/2014

OTHER PUBLICATIONS

Wu et al., 2012, Aging Research reviews, vol. 11, p. 32-40.*
Agrahari et al., 2017, Expert Opinion on Drug Delivery, vol. 14, No. 10, p. 1145-1162.*
Cheng et al., 2017, Stem Cells International, vol. 2017, Article ID 6305295, 10 pages.*
Bassit et al., "MALAT1 in human adipose stem cells modulates survival and alternative splicing of PKδII in HT22 cells," Endocrine Society (2016) DOI: 10.1210/en. 2016-1819, 30 pages.
Bonafede et al. "Exosome derived from murine adipose-derived stromal cells: Neuroprotective effect on in vitro model of amyotrophic lateral sclerosis," research article (2016) Experimental Cell Research 340, pp. 150-158, www.elsevier.com/locate/yexcr.
Cervelli et al., "Platelet-Rich Plasma Greatly Potentiates Insulin-Induced Adipogenic Differentiation of Human Adipose-Derived Stem Cells Through a Serine/Threonine Kinase Akt-Dependent Mechanism and Promotes Clinical Fat Graft Maintenance," Stem Cells Transl Med. (2012) 1(3): 206-220.
Howitt et al., "Exosomes in the Pathology of Neurodegenerative Diseases," Manuscript R116.757955, J. Biol. Chem. (2016) pp. 1-24, http://www.jbc.org/cgi/doi/10.1074/jbc.R116.757955.
Salgado et al., "Adipose Tissue Derived Stem Cells Secretome: Soluble Factors and Their Roles in Regenerative Medicine," Current Stem Cell Research & Therapy, 2010, 5, 103-110.
Zhang et al., "Physiological and pathological impact of exosomes of adipose tissue," Cell Prolif. (2016) 49, 3-13.

* cited by examiner

*Primary Examiner* — Shin Lin Chen
(74) *Attorney, Agent, or Firm* — Fish & Richardson P.C.

(57) ABSTRACT

Brain injury can be caused by trauma or may occur in stroke or neurodegenerative diseases. The disclosure relates to compositions that can include exosomes isolated from human adipose-derived stem cells (hASC) and methods where exosomes from hASC may be used alone or in combination with insulin for the treatment of brain injury.

12 Claims, 42 Drawing Sheets
(41 of 42 Drawing Sheet(s) Filed in Color)
Specification includes a Sequence Listing.

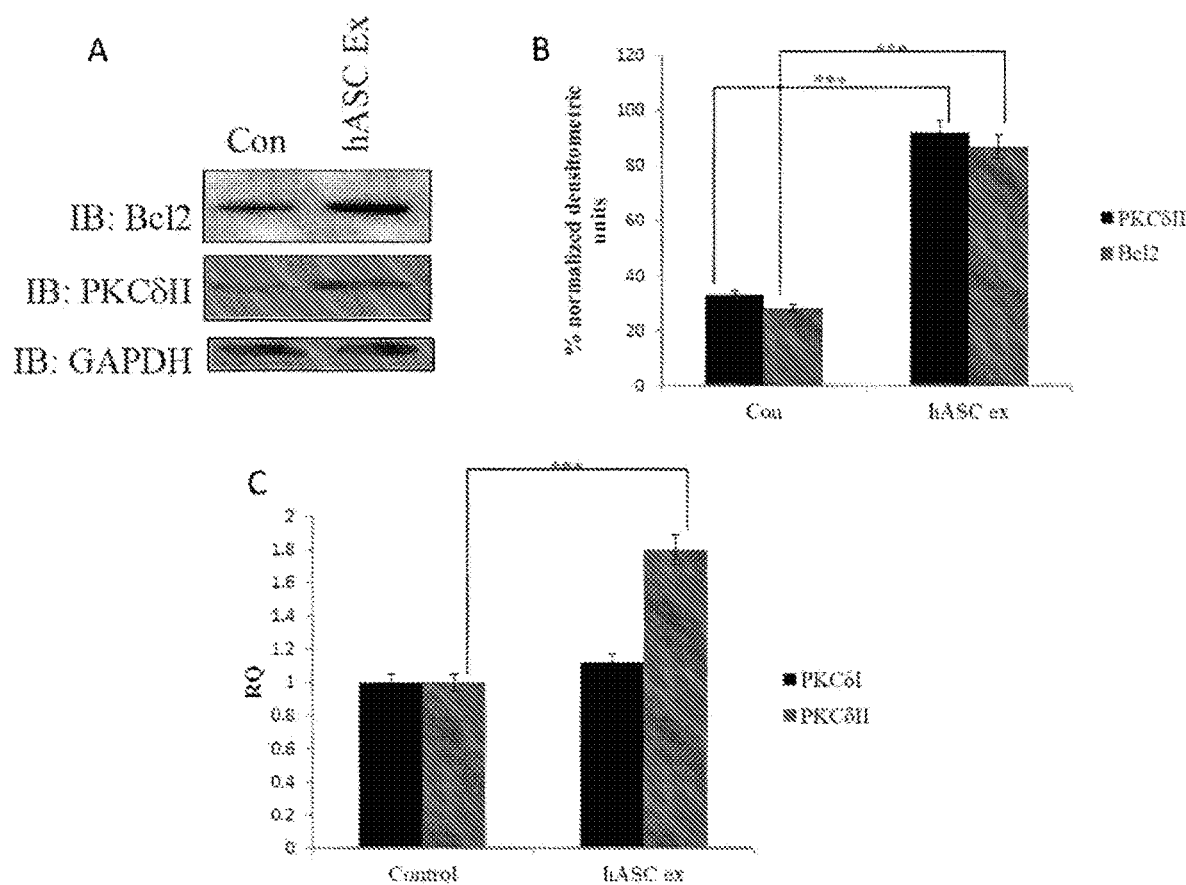
FIGS. 1A-C

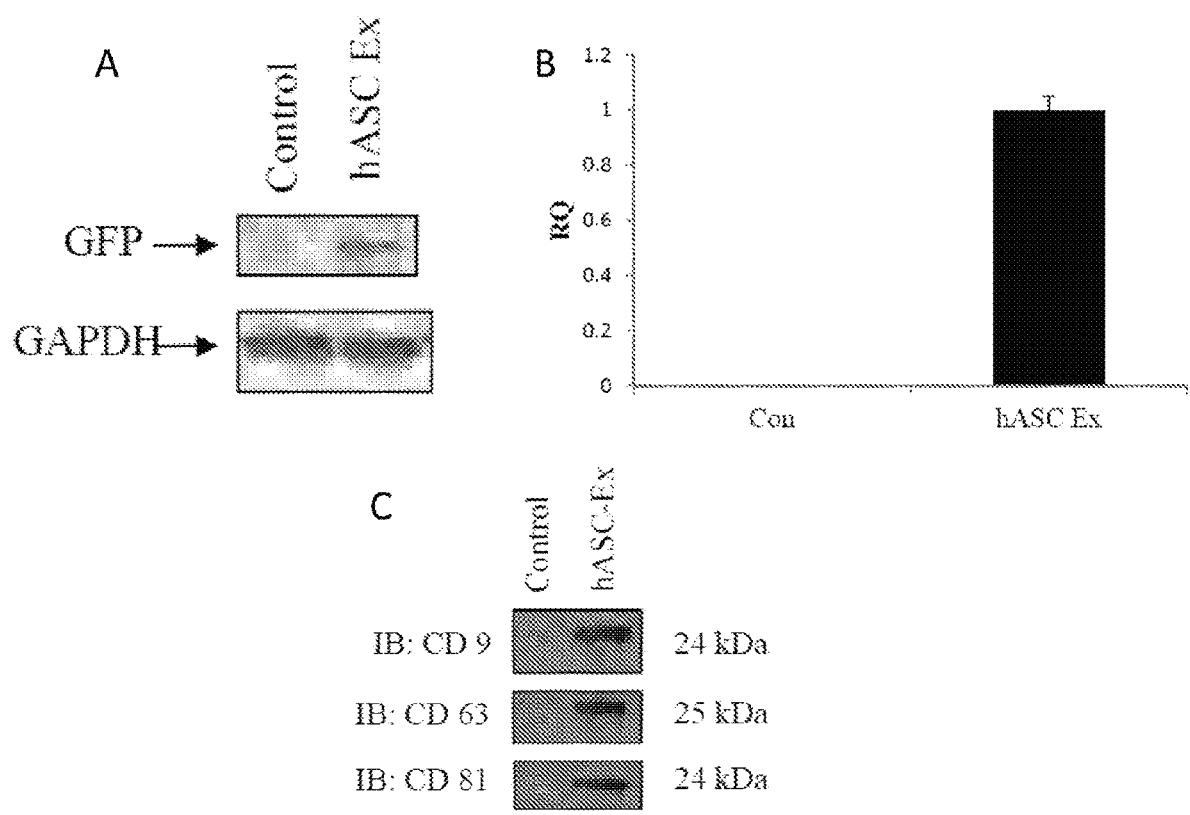
FIGS. 2A-C

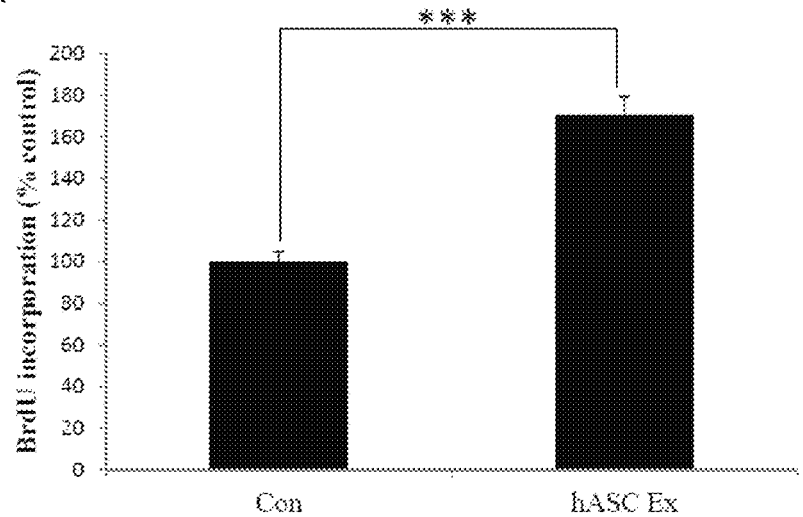
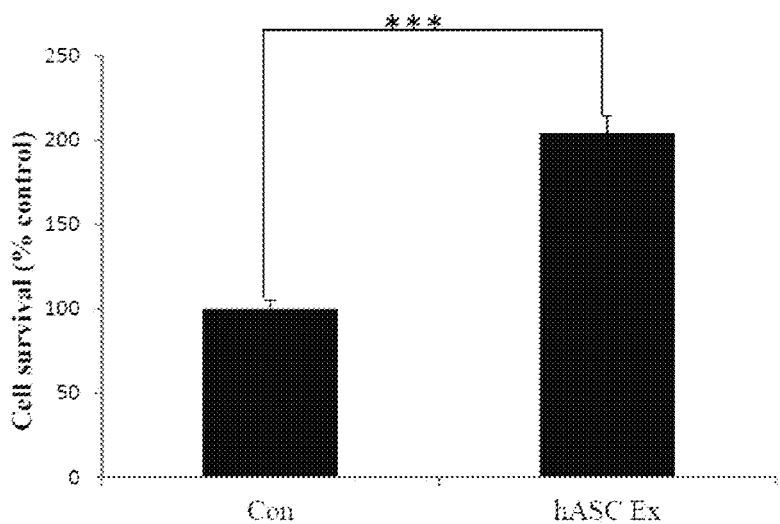
FIGS. 3A-B

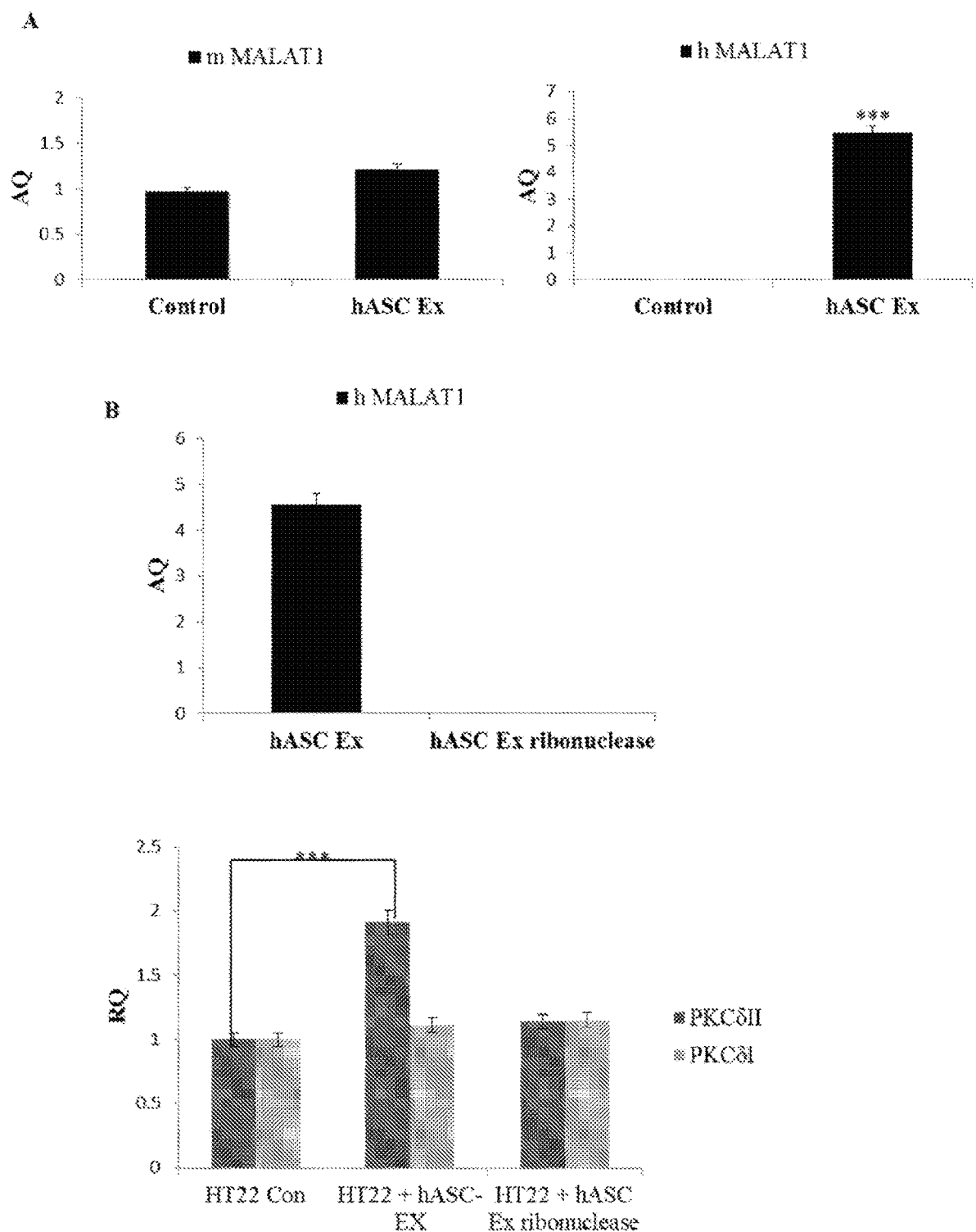
FIGS. 4A-B

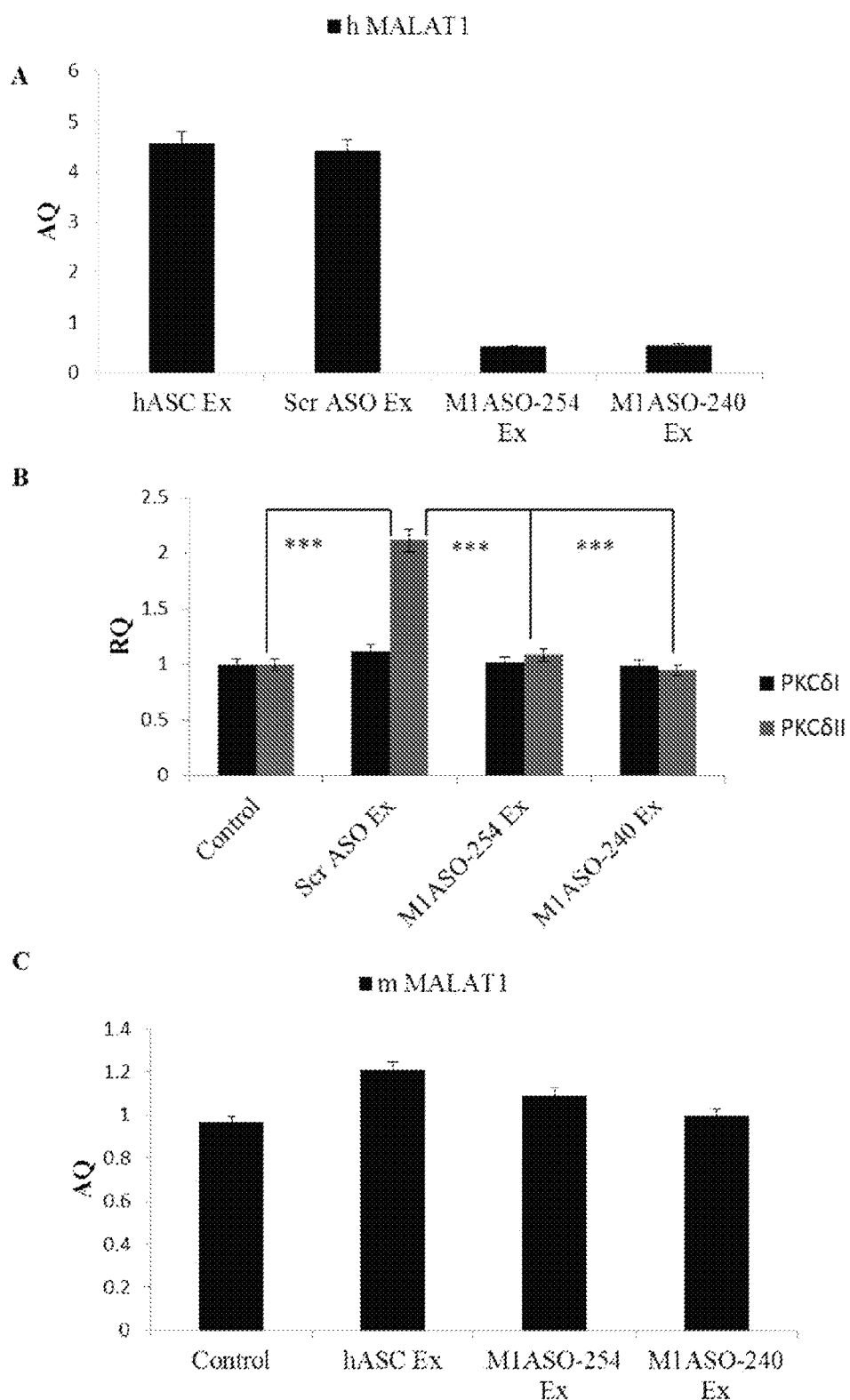
FIGS. 5A-C

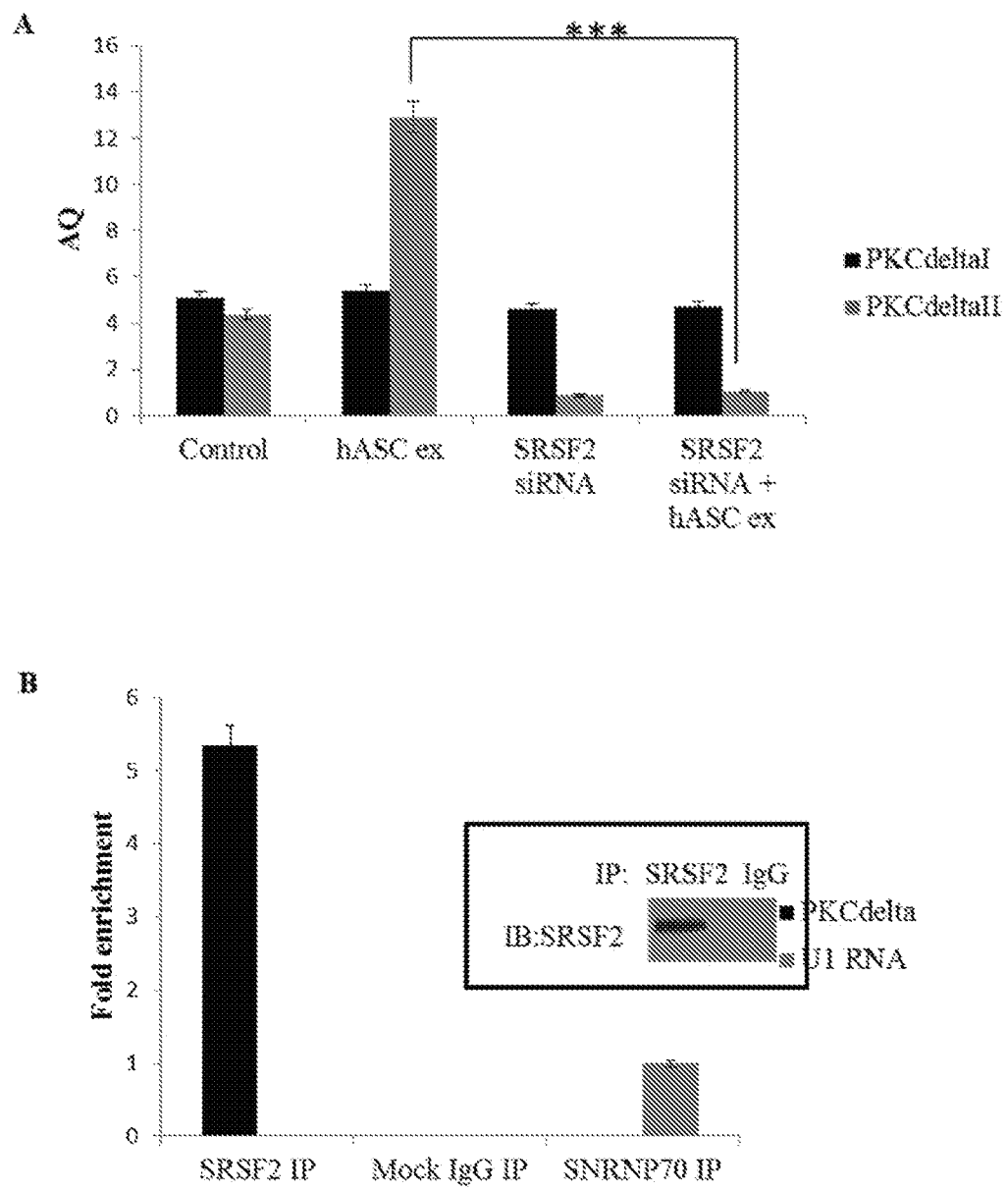
FIGS. 6A-B

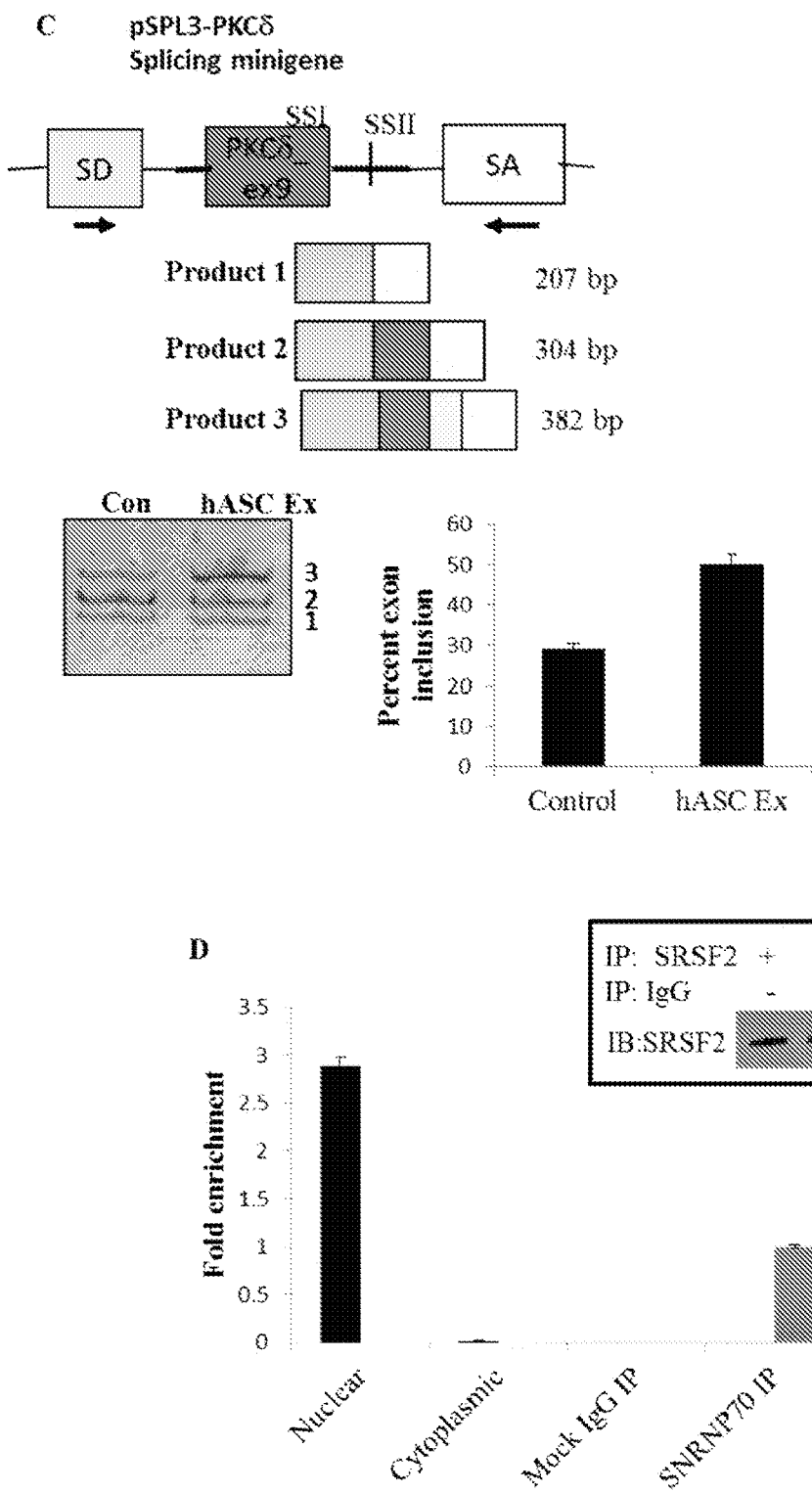
FIGS. 6C-D

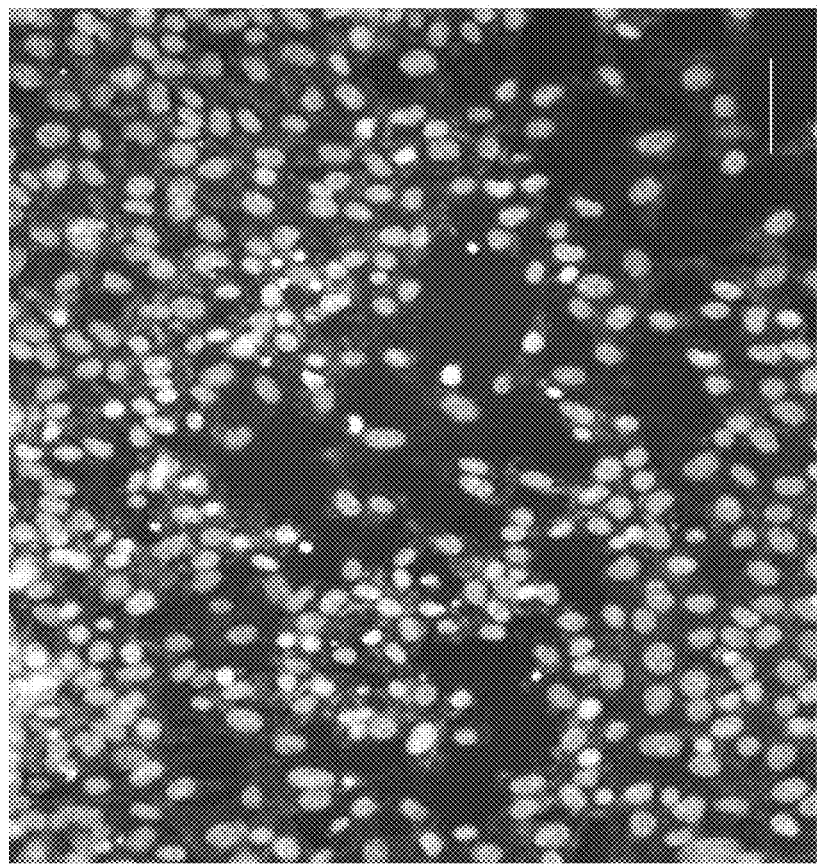
FIG. 7A

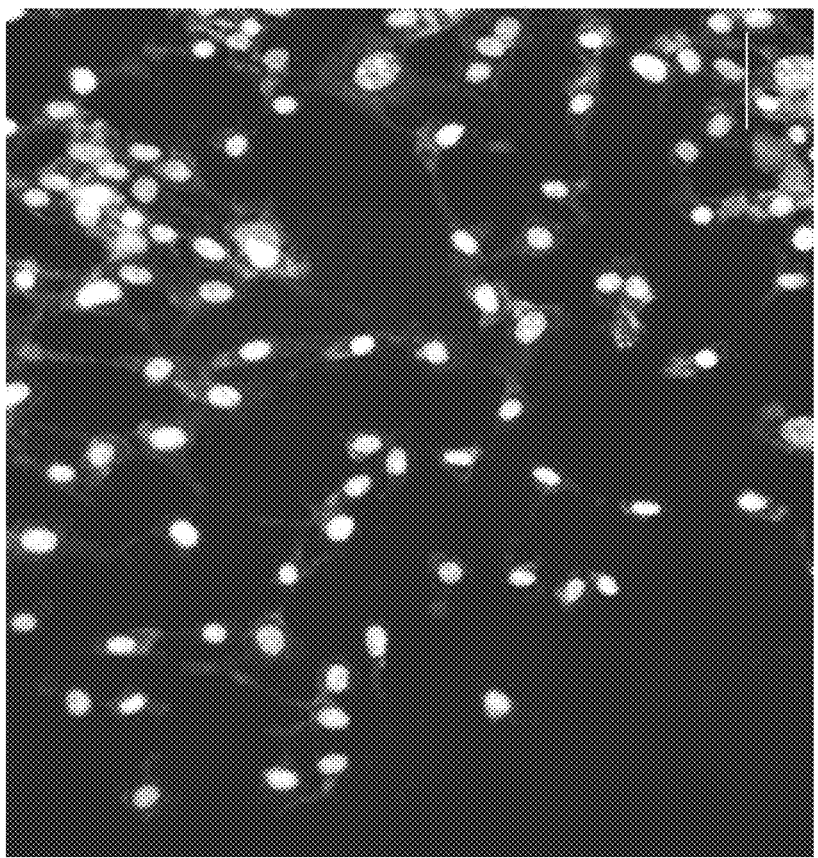
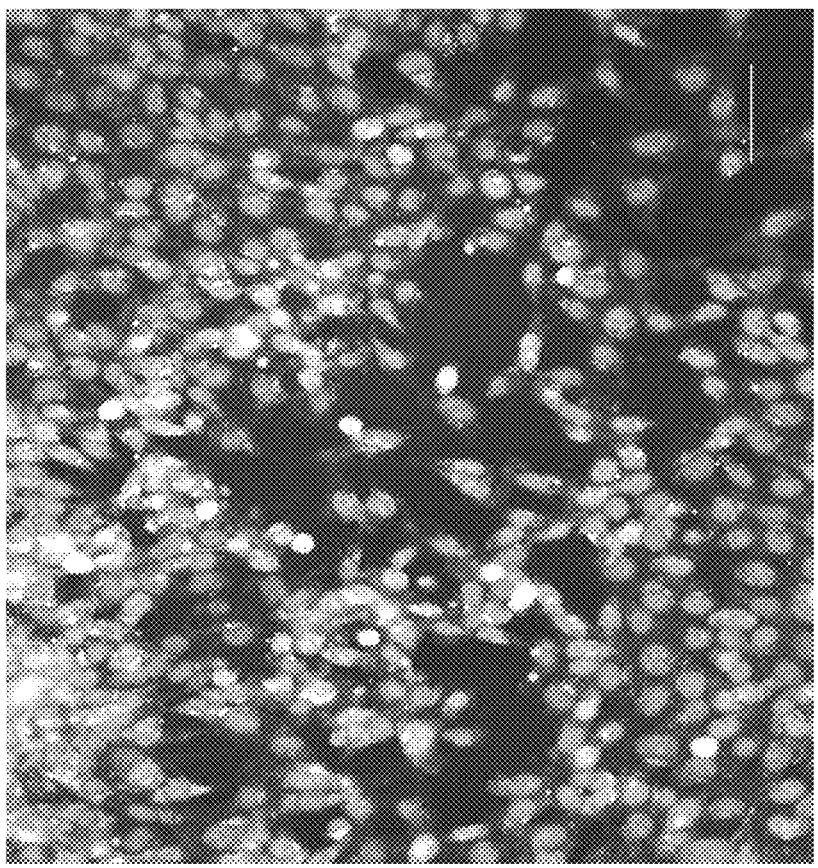
FIG. 7A, CONTINUED

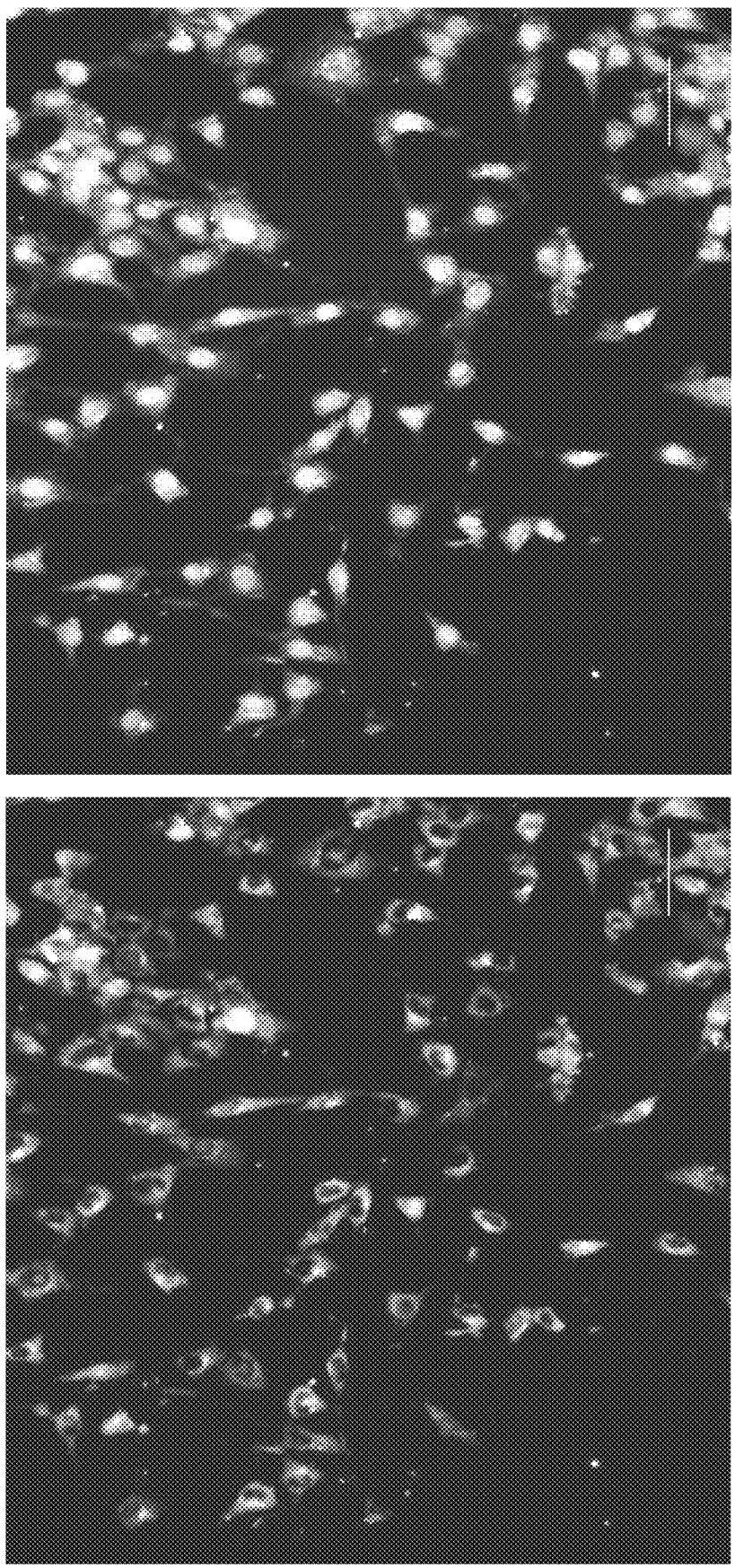
FIG. 7A, CONTINUED

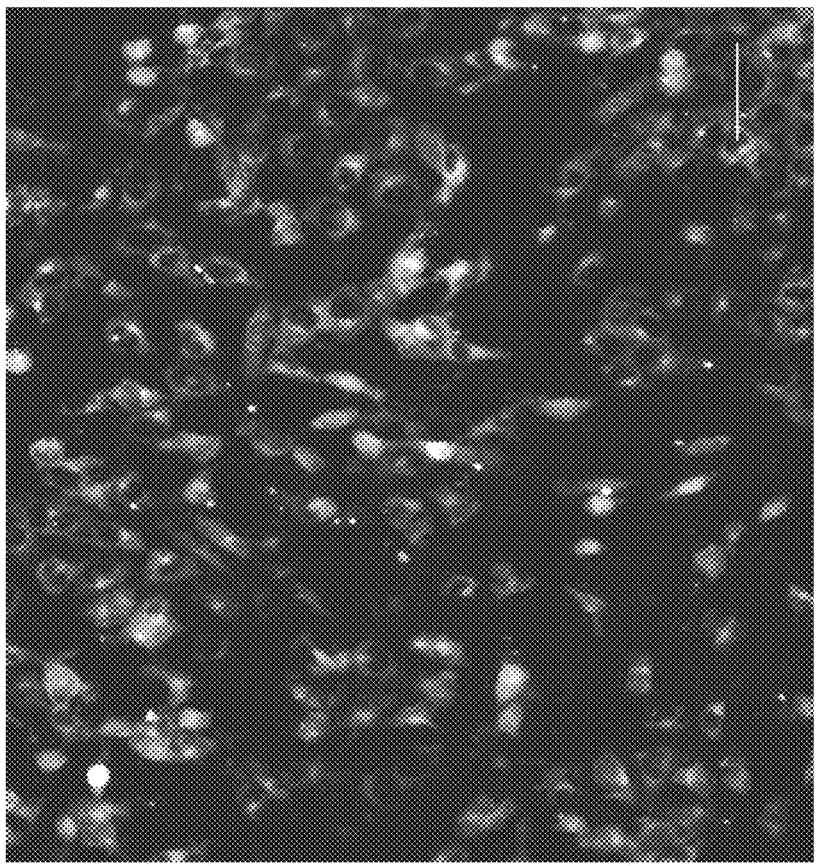
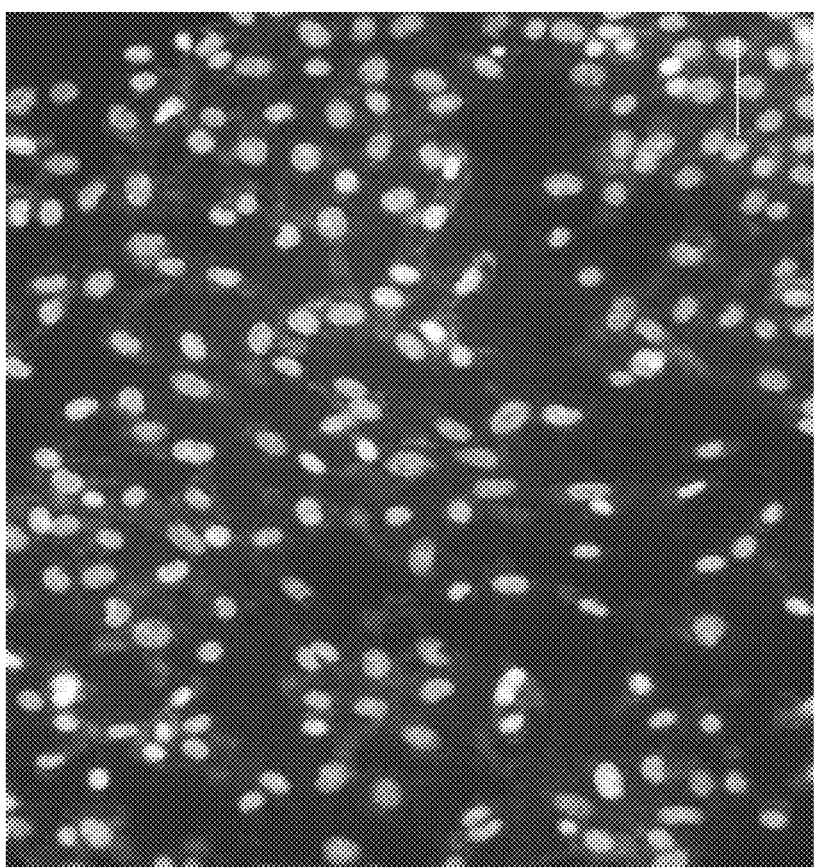
FIG. 7A, CONTINUED

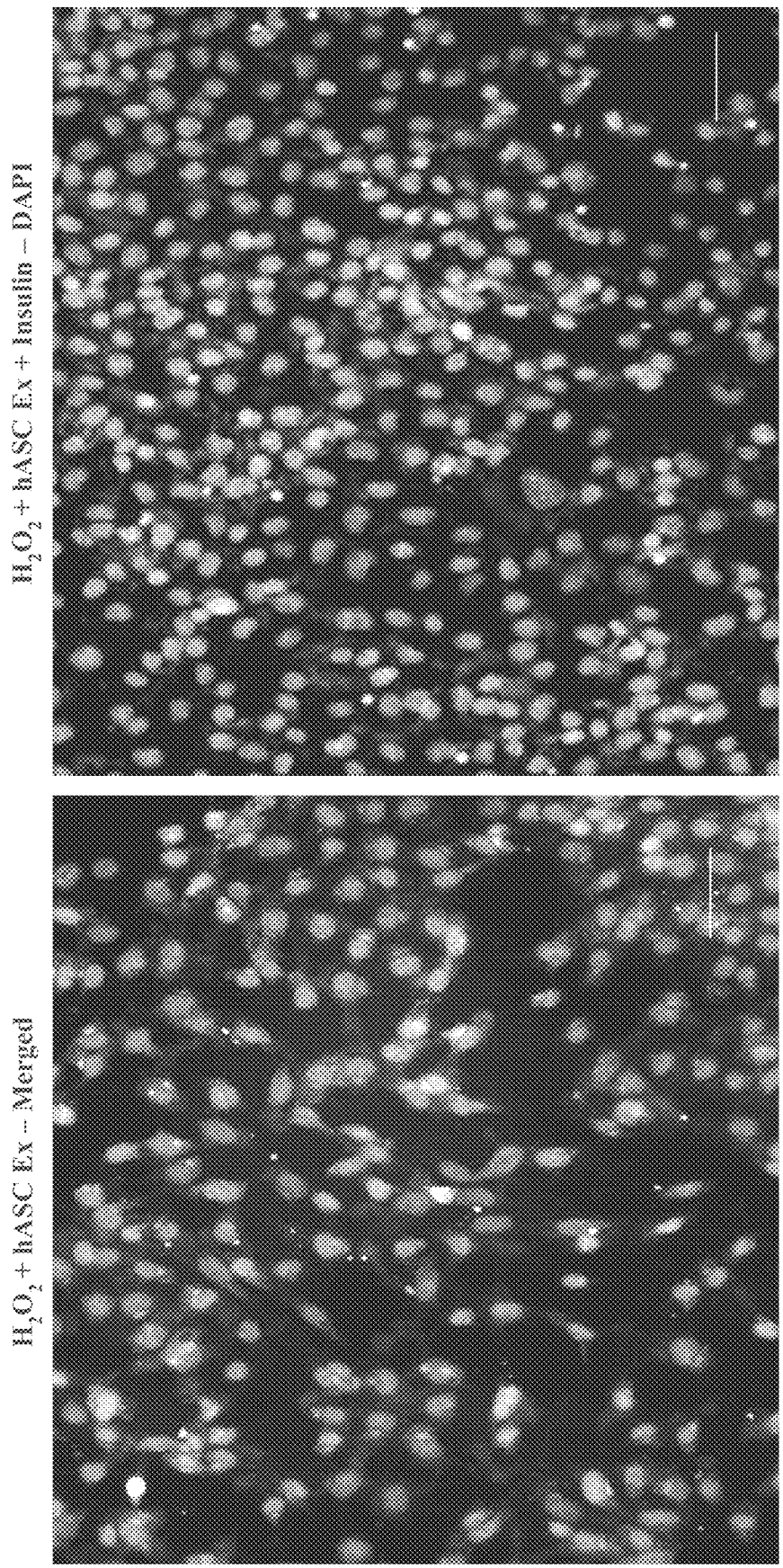
FIG. 7A, CONTINUED

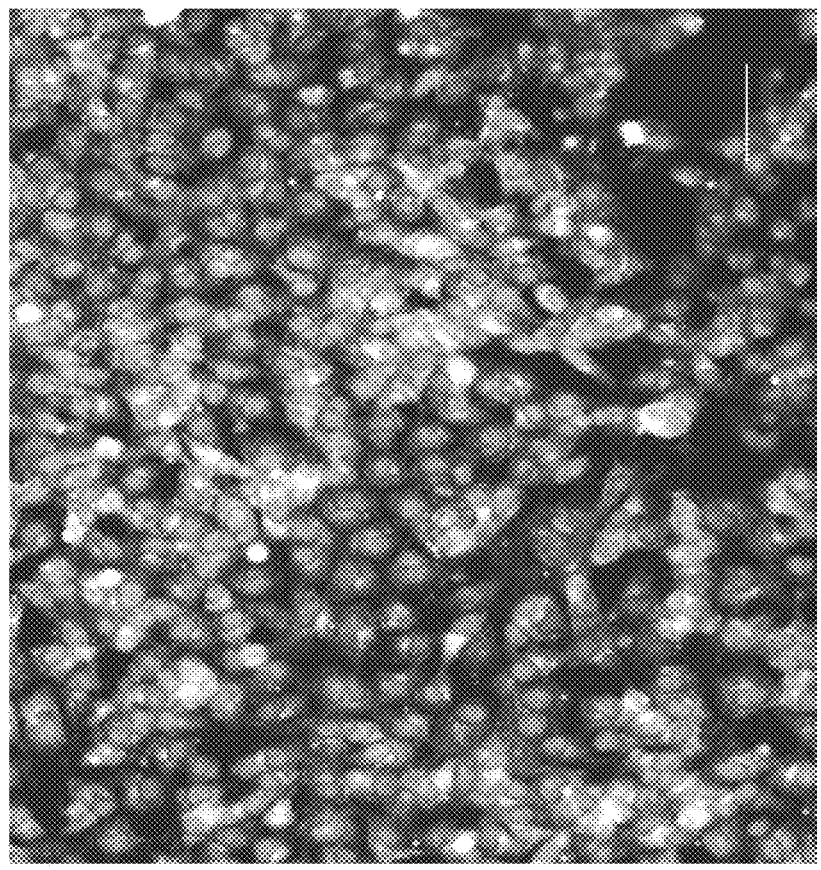
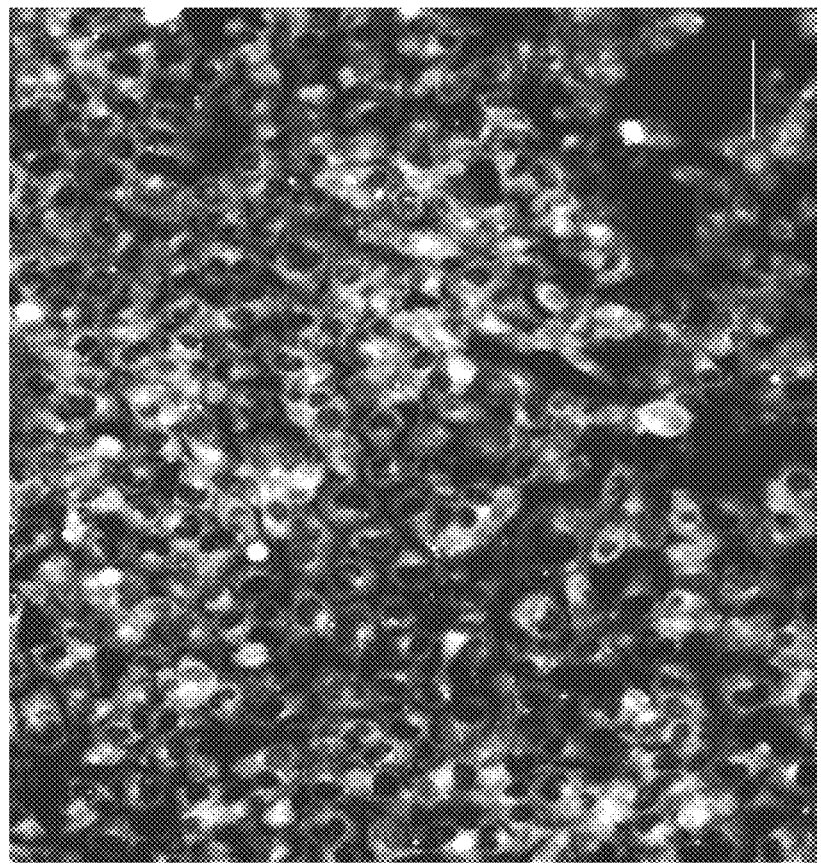
FIG. 7A, CONTINUED

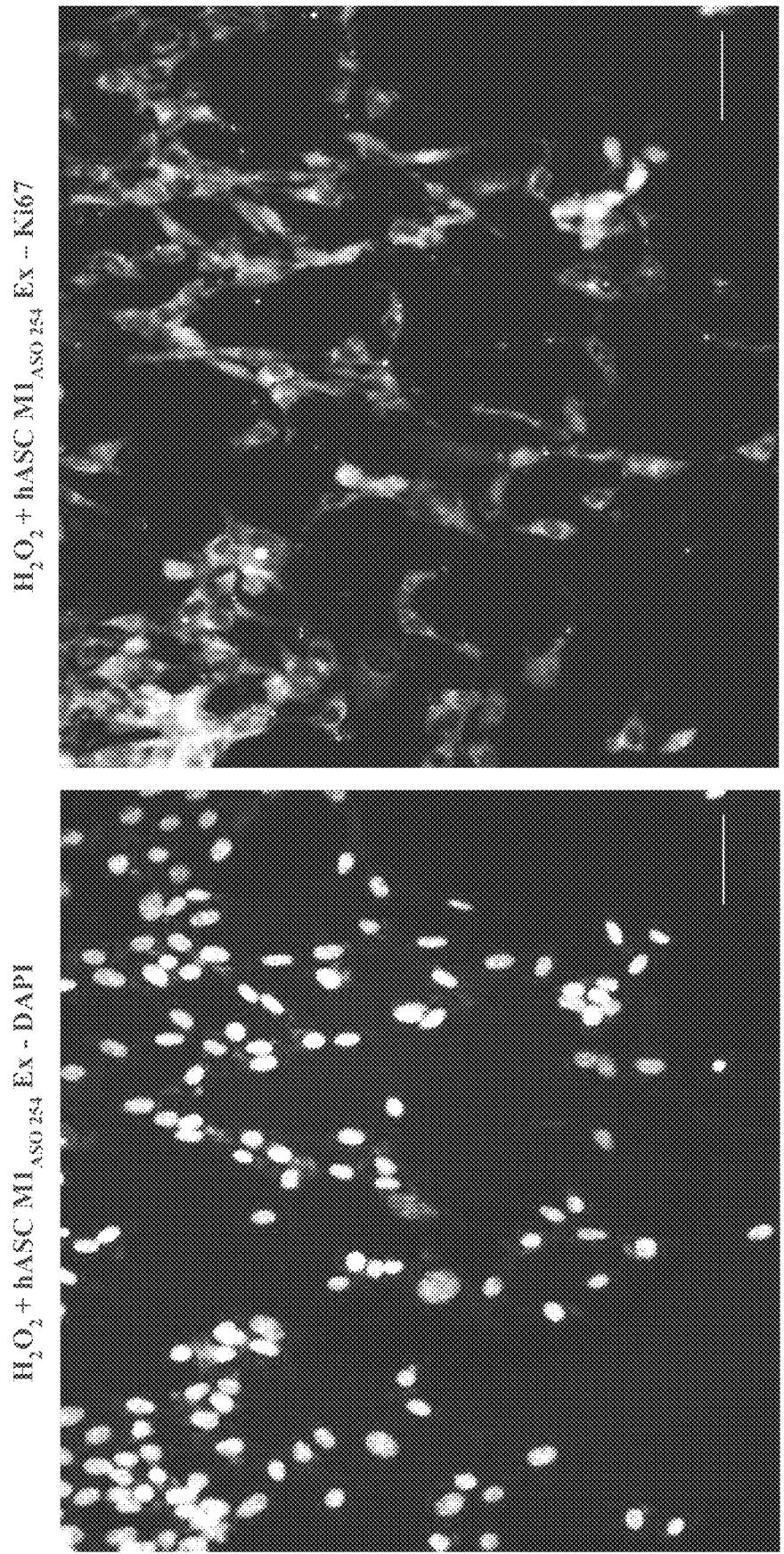
FIG. 7A, CONTINUED

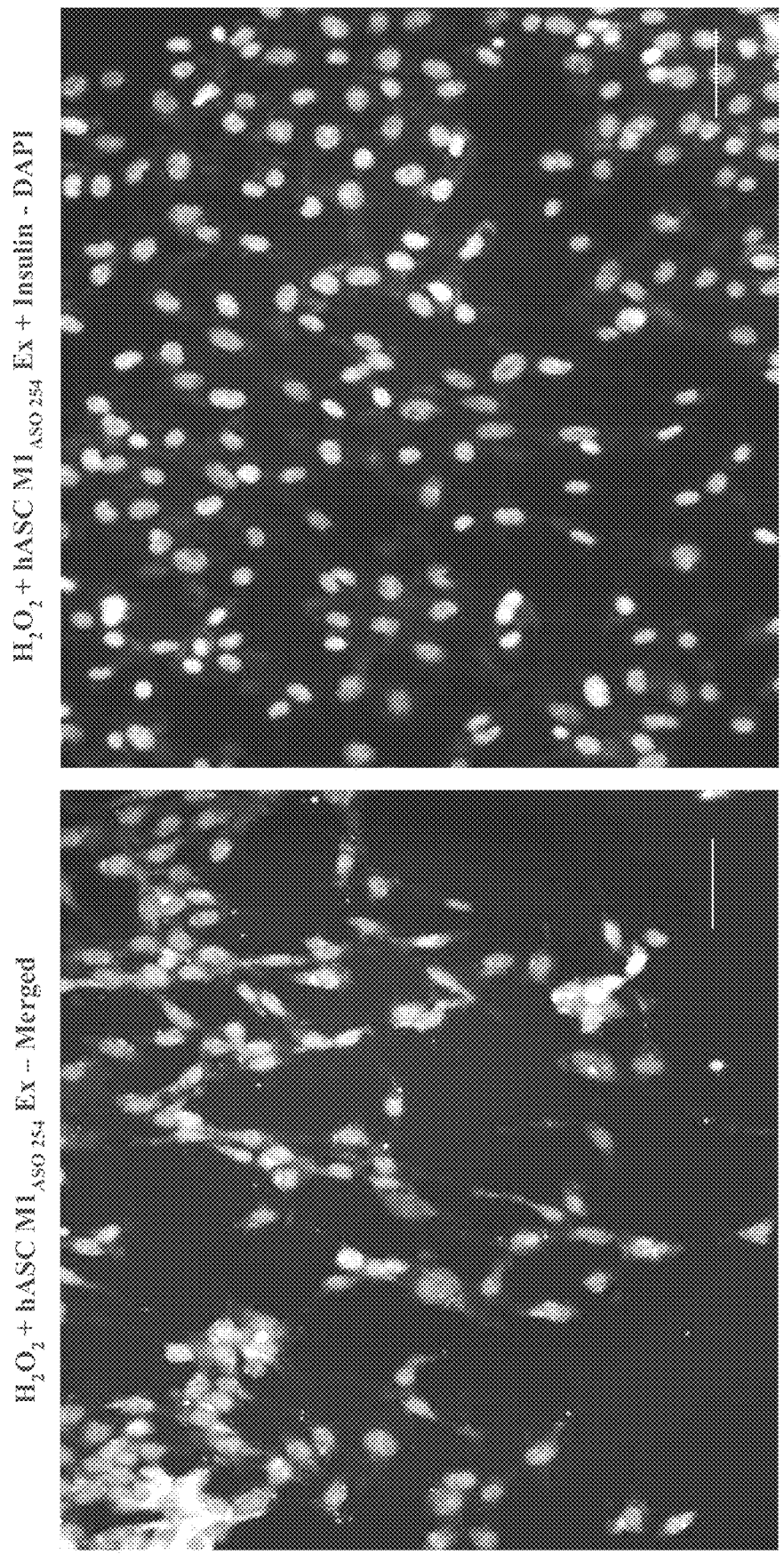
FIG. 7A, CONTINUED

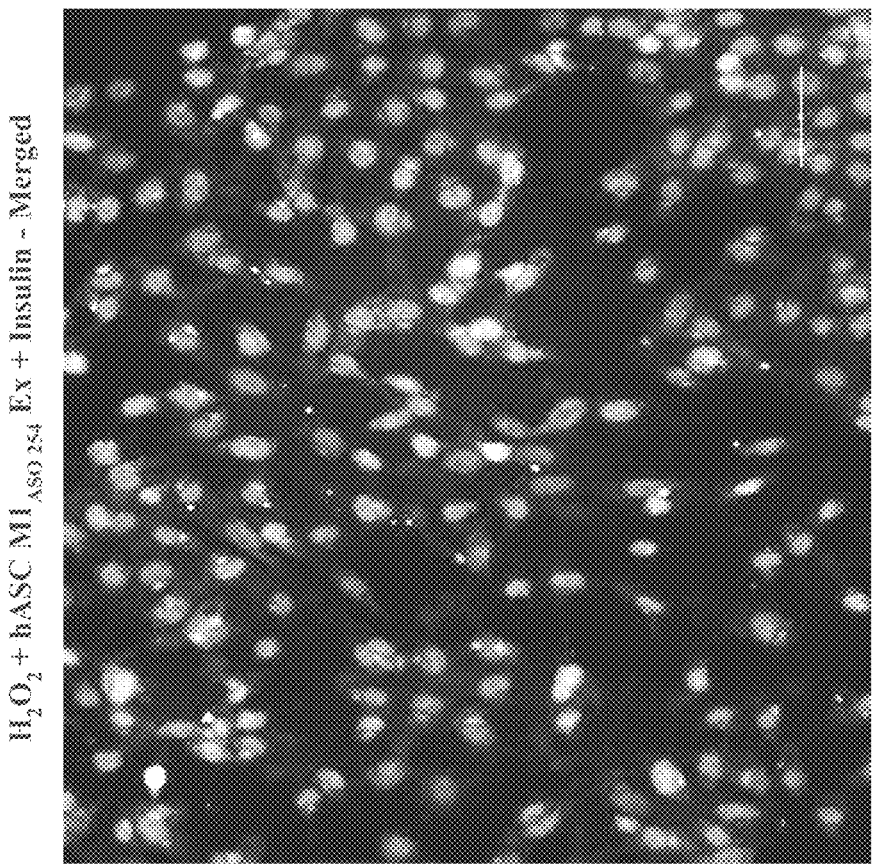
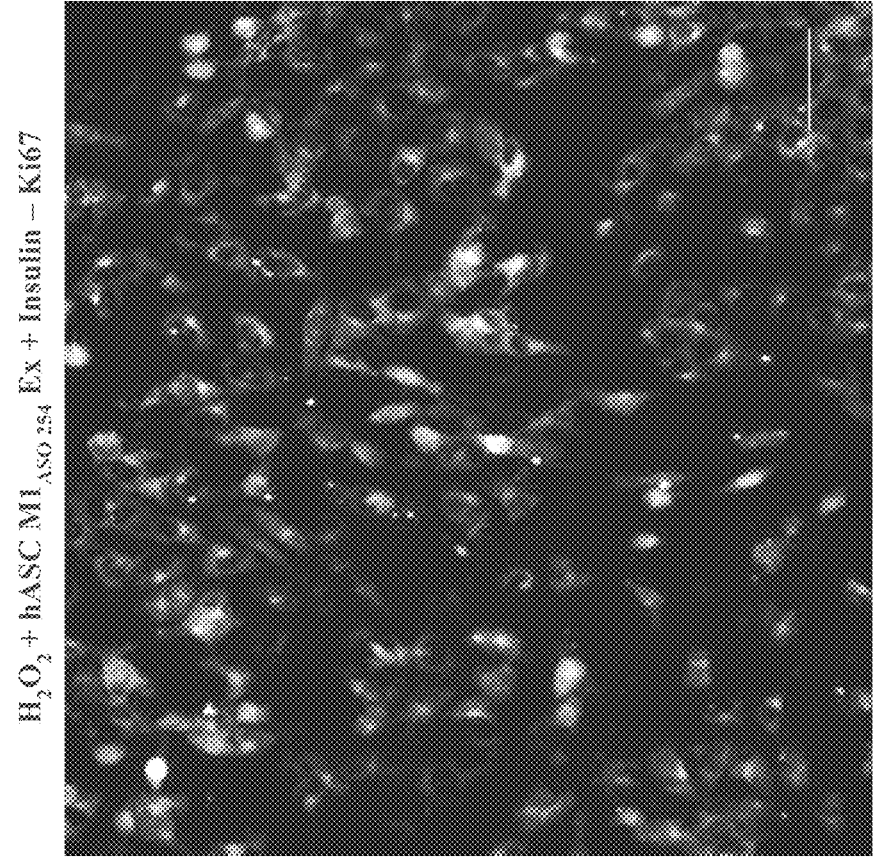
FIG. 7A CONTINUED

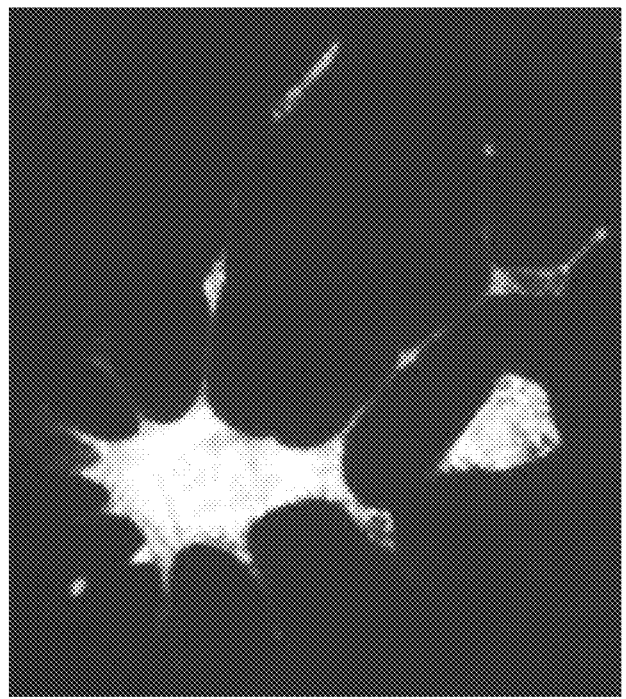
FIG. 7A, CONTINUED

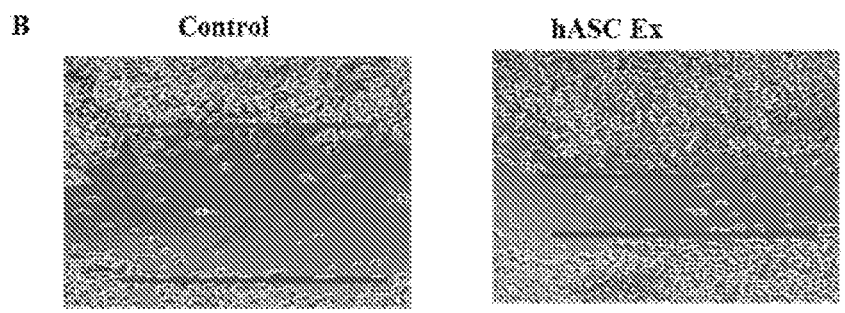
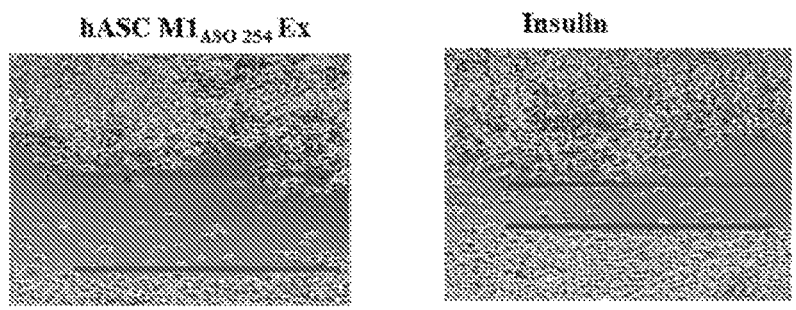
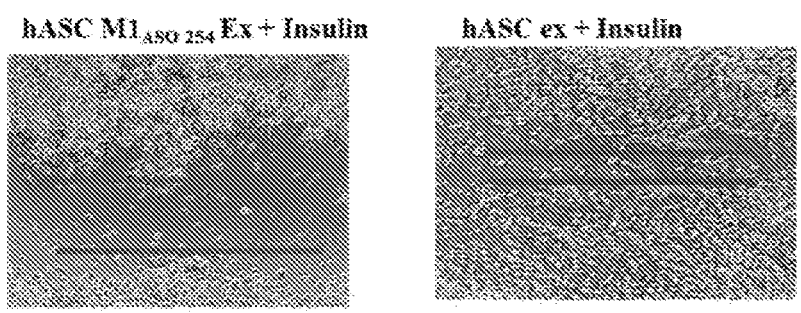
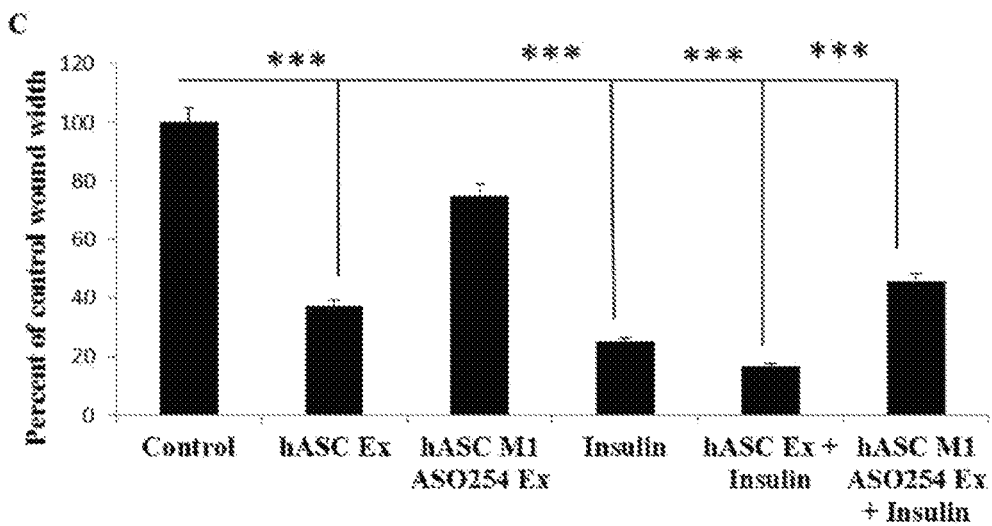
FIGS. 7B-C

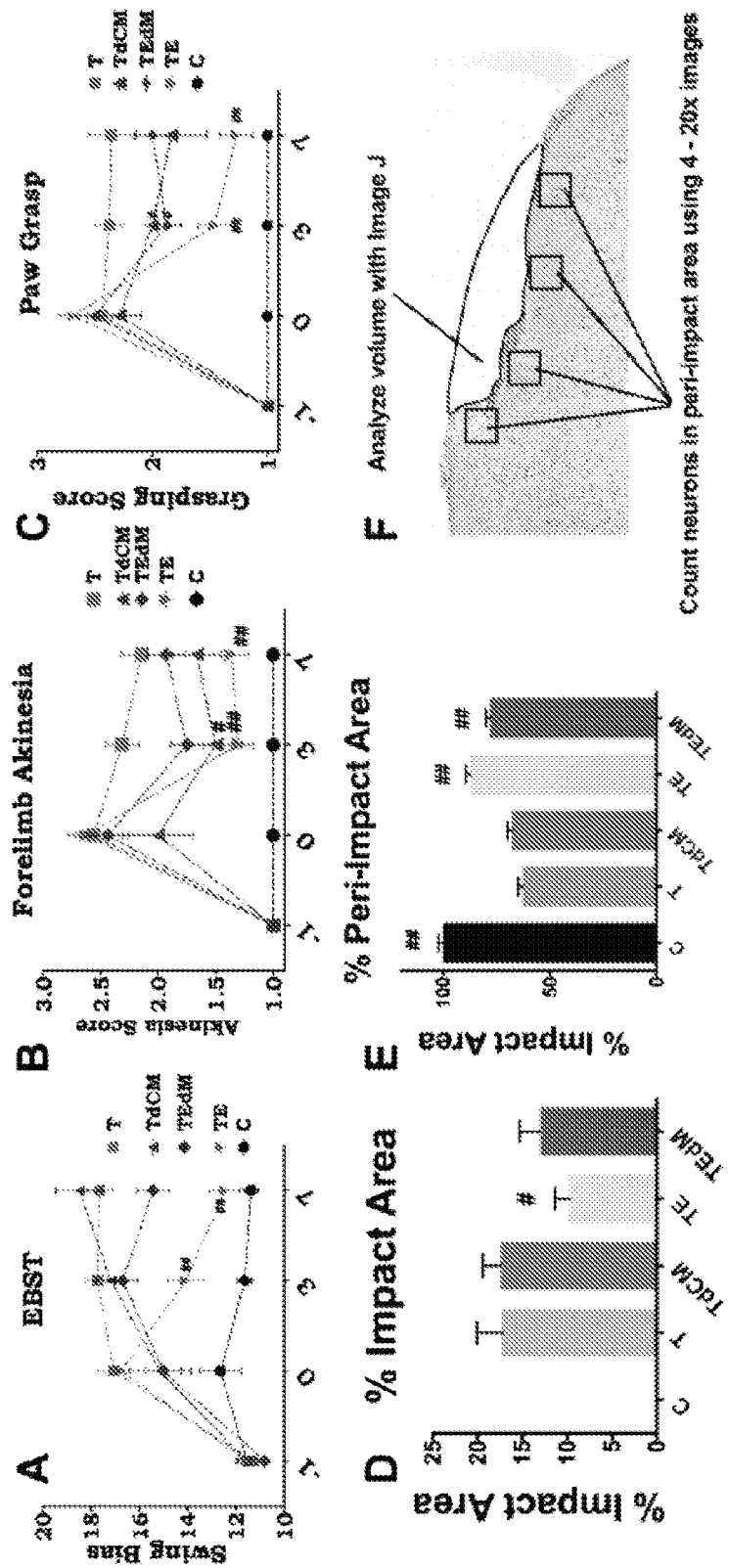
FIGS. 9A-F

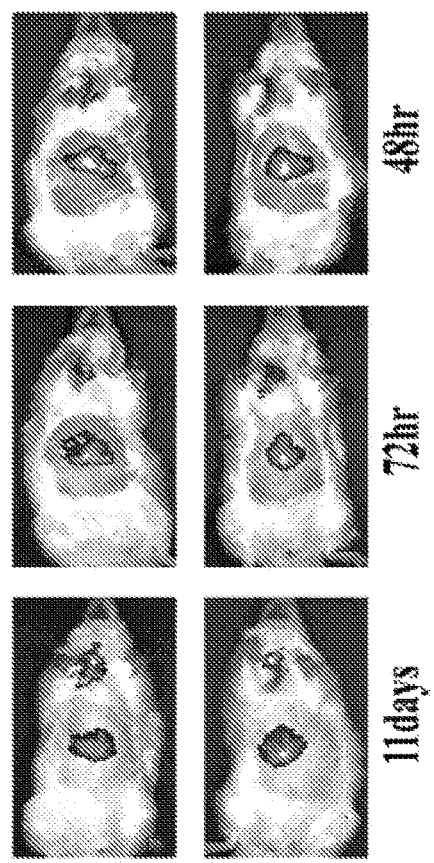
FIG. 10B, CONTINUED

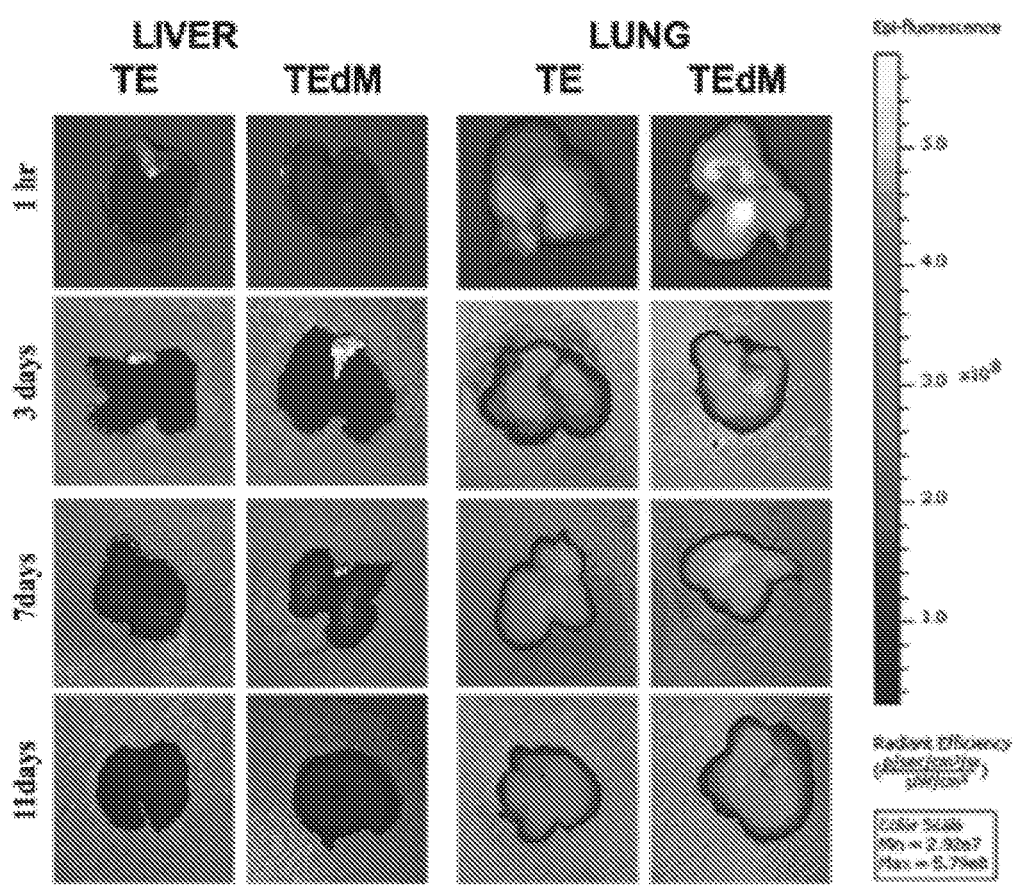
FIG. 11A, CONTINUED

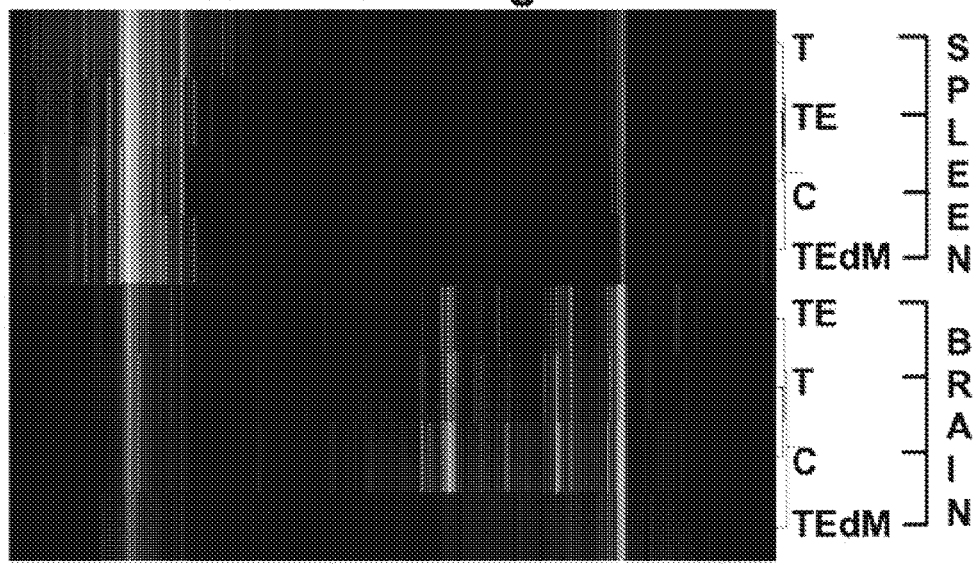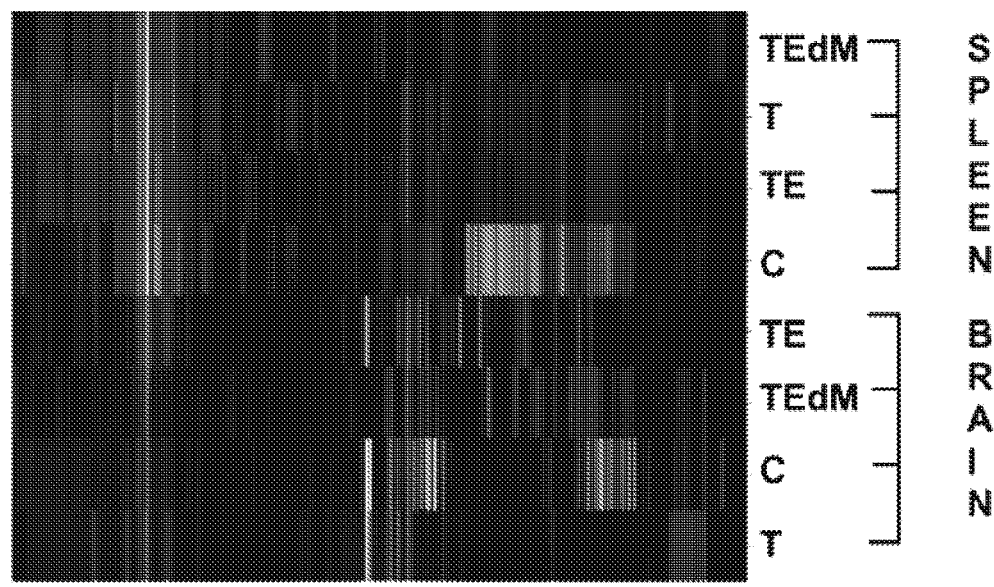
FIG. 12A-B

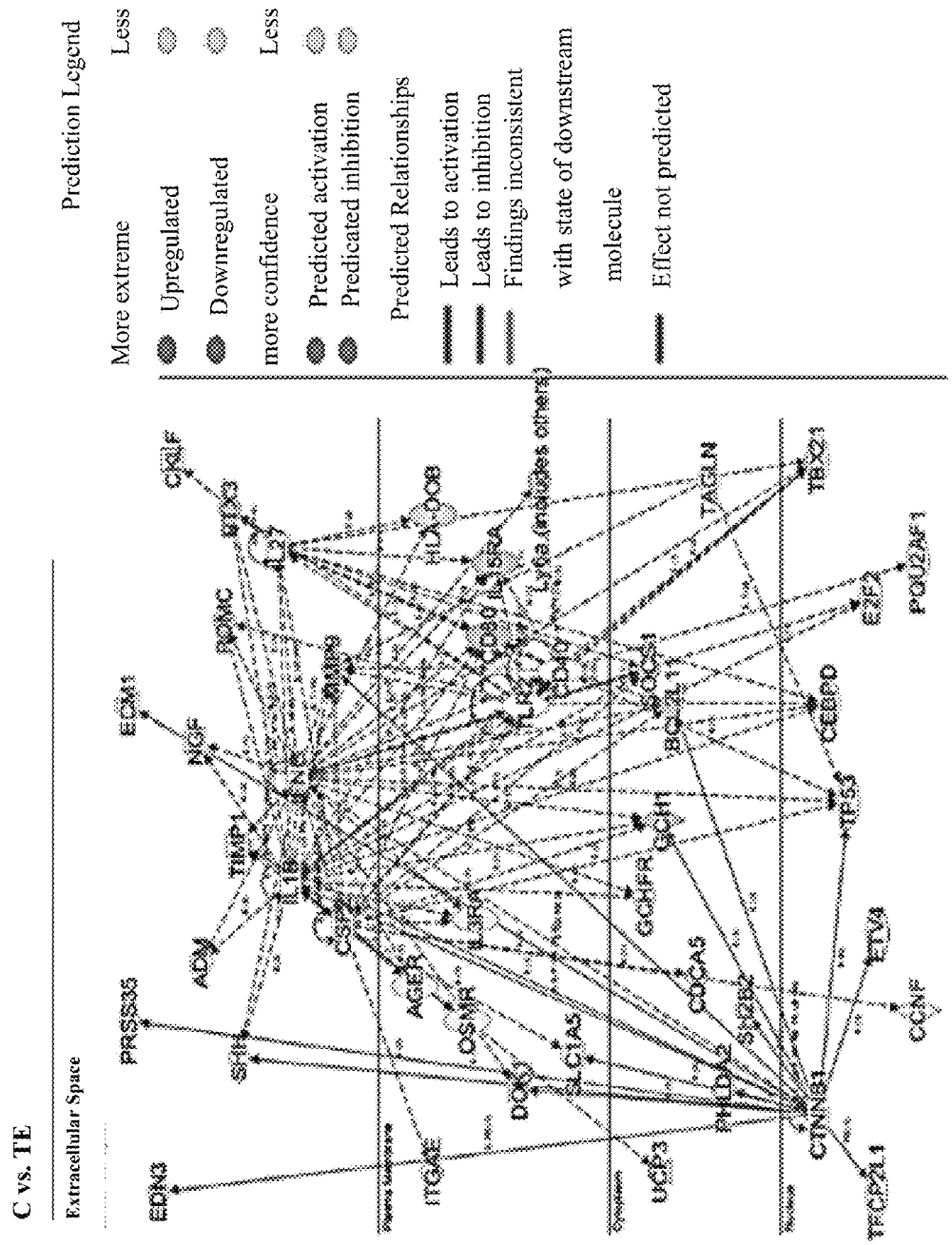
FIG. 13, CONTINUED

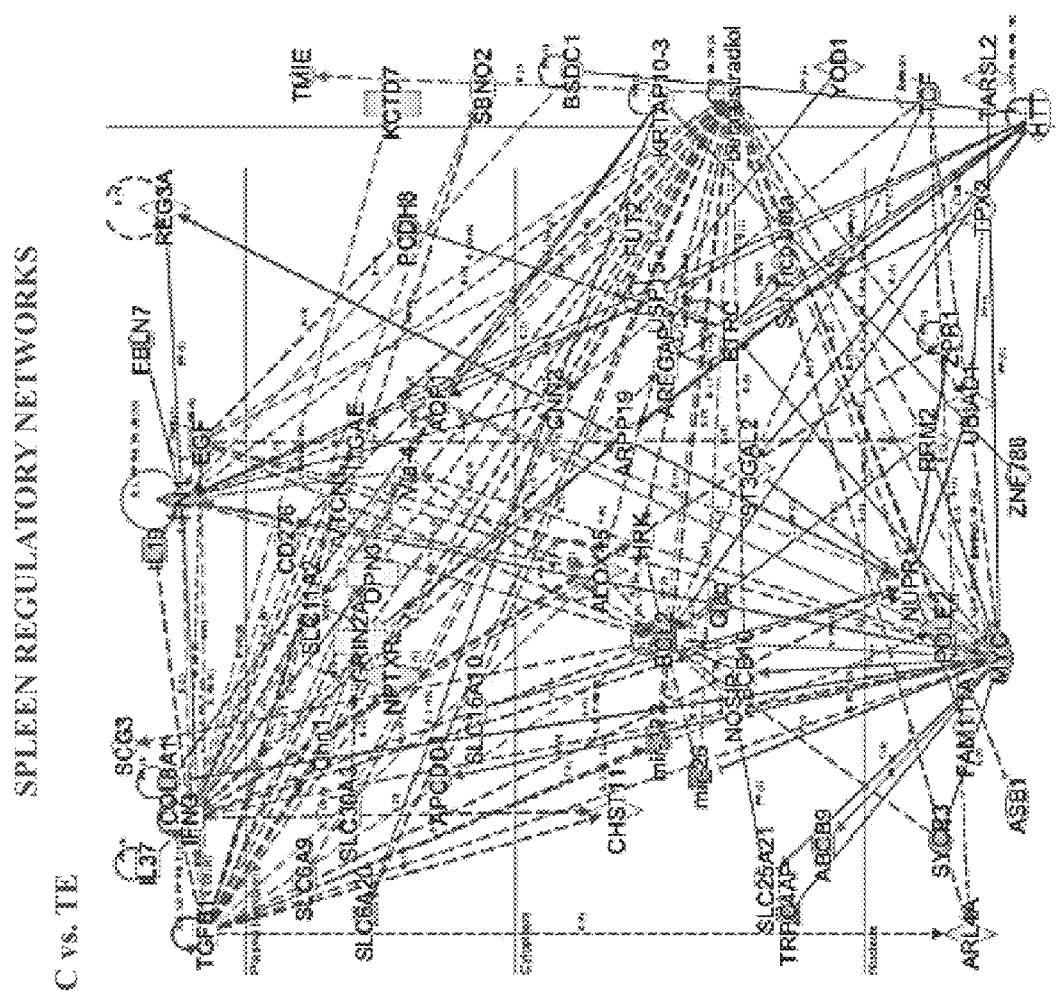
FIG. 14, CONTINUED

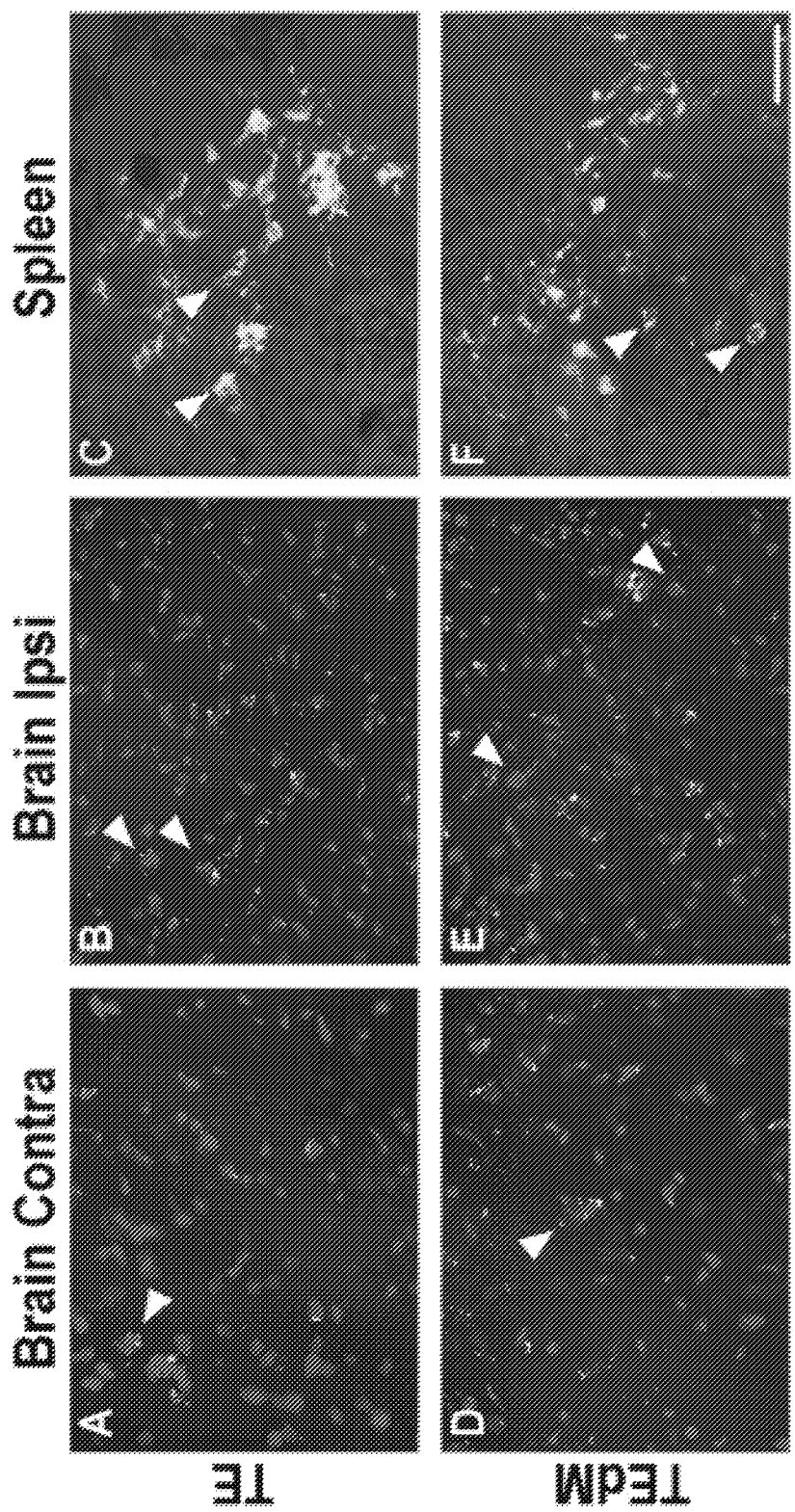
FIG. 15A-F

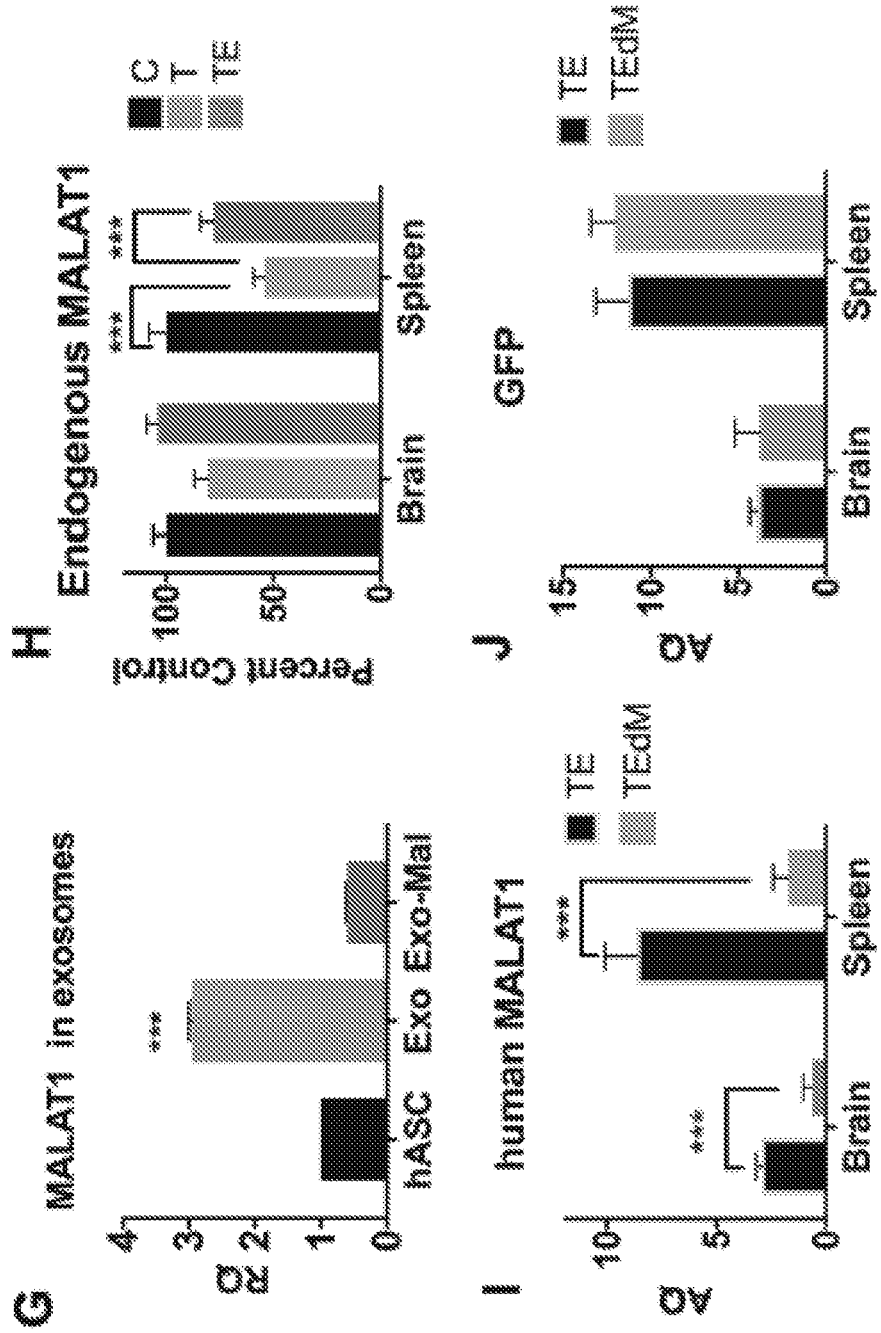
FIG. 15G-J

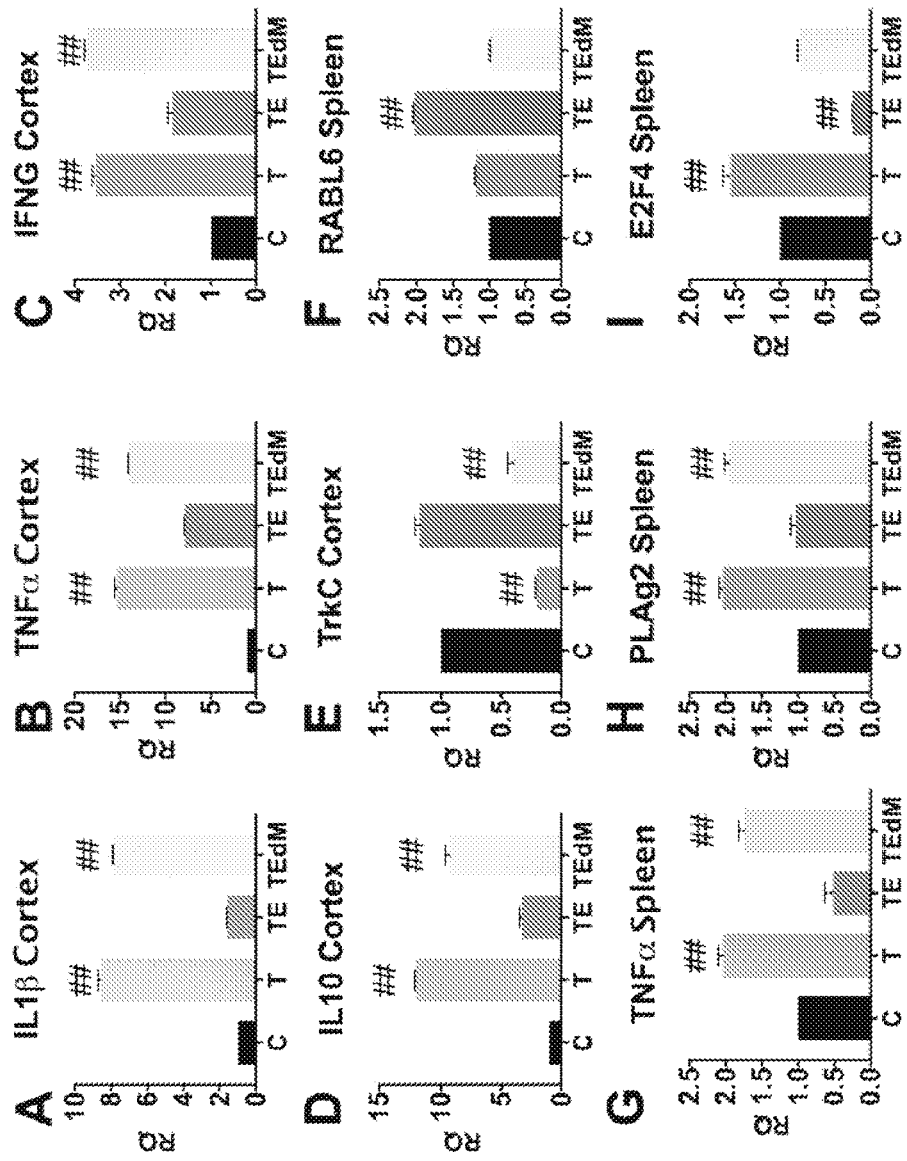
FIG. 16A-I

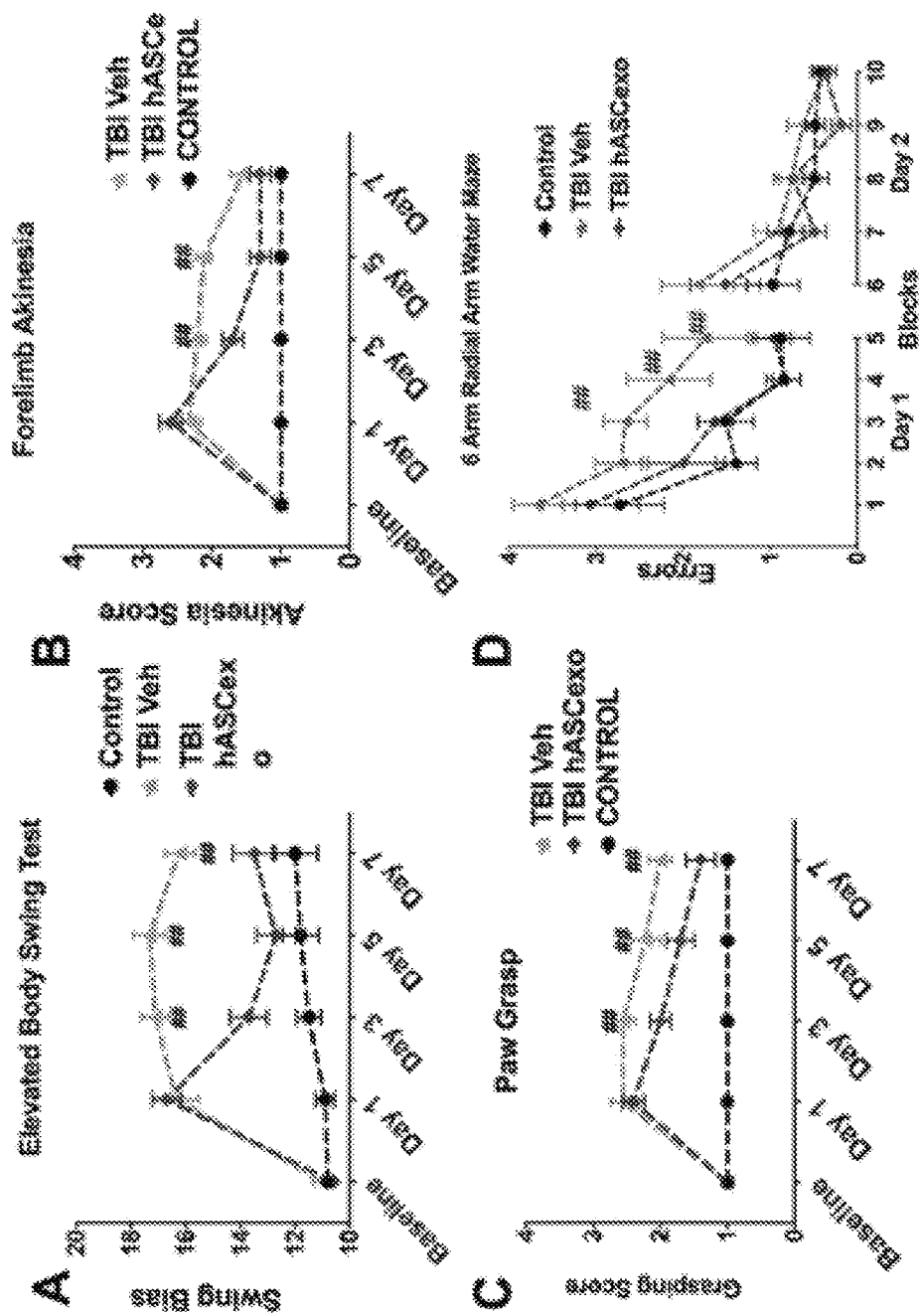
FIGS. 18A-D

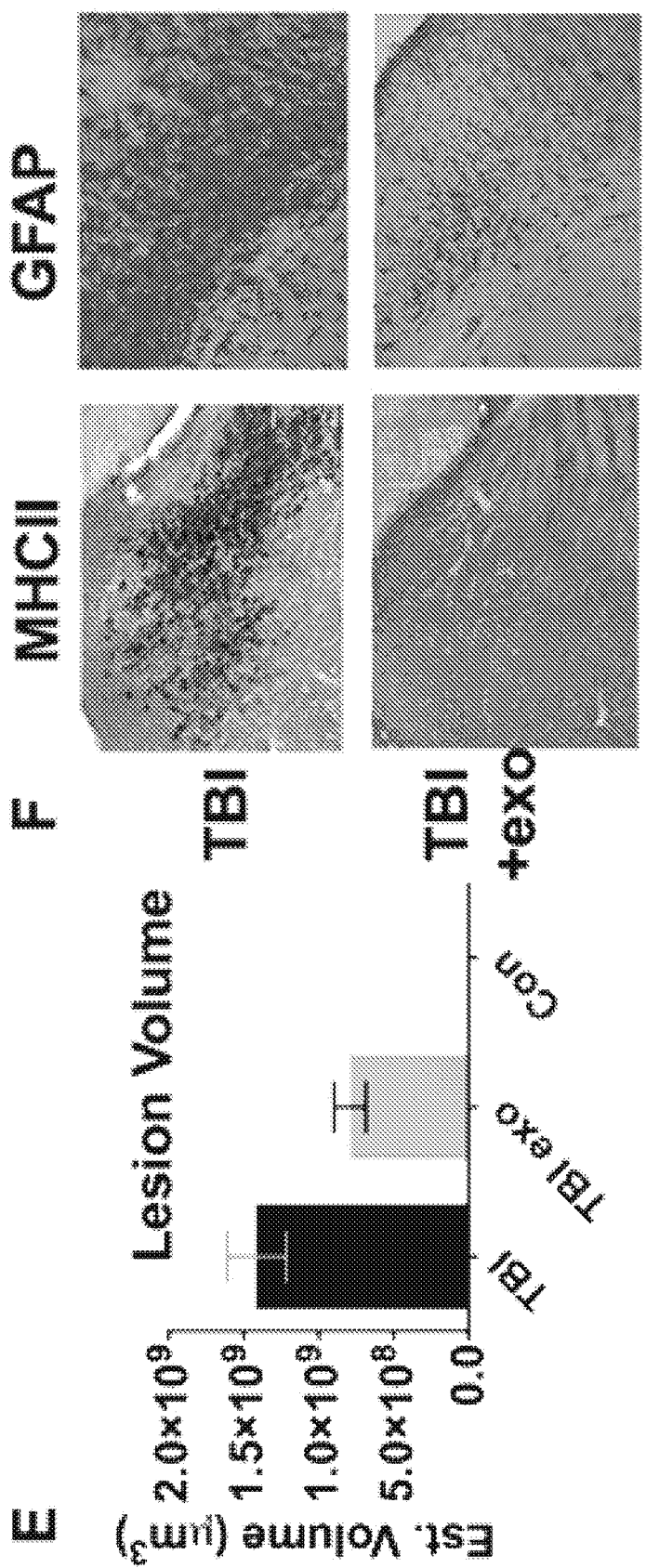
FIGS. 18E-F

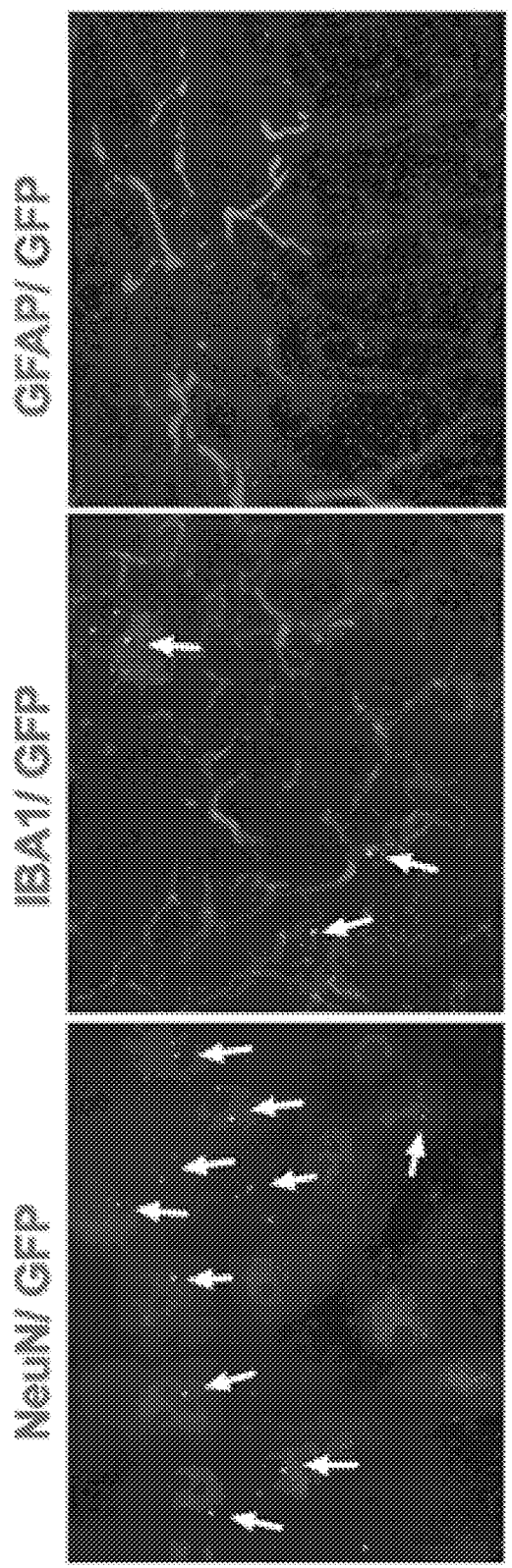
FIGS. 19A-C

Upstream Regulators

Inflammation, Apoptosis, Transcription, cardiovascular, RNA processing, metabolism

| BRAIN | | SPLEEN | |
|---|---|---|---|
| Pattern 1 | Pattern -1 | Pattern 1 | Pattern -1 |
| IL1B* | TNNI1 | CDKN1A# | CACNG8 |
| IFNG* | PIH1D3 | E2F4 | KRT18 |
| CSF2* | SOX15 | PABL6* | CYP1A1 |
| TLR2* | mir-194 | CSF2* | CAV1 |
| P38 MAPK* | LNX2 | PTGER2* | EFNA4 |
| STAT3 | RFX3 | EP400* | EFNA3 |
| CTNNB1 | SFPQ | CCND1* | EFNA5 |
| IL27* | OXT | E2F3* | ADCY6 |
| NFkB (complex)* | SIX1 | Irgm1# | NAB1 |
| TNF* | Ubiquitin | ABCB6# | CYP1A2 |
| TAGLN | HEY2 | BNIP3L# | PTPN1 |
| Immunoglobulin | TCF7L1 | E2F* | CYP1B1 |
| S100A4 | UPF2 | FOXM1* | EFNA2 |
| STAT1 | ADRB2 | ERBB2* | GATA4 |
| Jnk | COMMD3-BMI1 | let-7# | PREB1 |
| CTF1 | Hsp70 | E2F1* | EOMES |
| Mek | PAX5 | E2F7 | SLC12A2 |
| STAT | | GATA1* | TBX5 |
| NFKBIA | | KLF1 | FOXN3 |
| MAPK8* | | NUPR1# | PTGDS |
| CNTF | | | |

* indicates a positive Z score indicating a predicted activation;
# indicates a negative Z score

FIG. 20

EXOSOMES FROM HUMAN ADIPOSE-DERIVED STEM CELLS FOR THE TREATMENT OF BRAIN INJURY

CROSS-REFERENCE TO RELATED APPLICATION(S)

This application claims priority to U.S. Provisional Patent Application No. 62/520,684, filed on Jun. 16, 2017, the entire contents of which are fully incorporated herein by reference.

STATEMENT REGARDING FEDERALLY FUNDED RESEARCH

This invention was made with government support under grant number 821-MR-EN-20606 awarded by the Department of Veterans Affairs. The government has certain rights in the invention.

INCORPORATION-BY-REFERENCE OF MATERIAL SUBMITTED ELECTRONICALLY

Incorporated by reference in its entirety herein is a computer-readable nucleotide/amino acid sequence listing submitted concurrently herewith and identified as follows: One 2,520 Bytes ASCII (Text) file named "17A043PRC-210112-9058-US02_ST25.txt", created on Jun. 18, 2018.

TECHNICAL FIELD

This invention relates to methods of treating brain injury. Specifically, the invention describes methods of treating brain injury using exosomes from human adipose-derived stem cells (hASC). Exosomes from hASC may be used alone or in combination with insulin for the treatment of brain injury.

BACKGROUND

Brain injury may be caused by trauma or may occur in stroke and neurodegenerative diseases. As the central nervous system is unable to regenerate efficiently, there is utmost interest in the development of methods to enhance regeneration and survival of neurons following brain injury in order to improve patient outcome.

SUMMARY OF INVENTION

The invention discloses a method of treating brain injury in a subject, comprising administering to the subject a composition comprising exosomes isolated from human adipose-derived stem cells. The composition may be administered alone or in combination with insulin. The subject may be a mammal, such as a human.

BRIEF DESCRIPTION OF THE DRAWINGS

This patent or application file contains at least one drawing executed in color. Copies of this patent or patent application publication with color drawing(s) will be provided by the Office upon request and payment of the necessary fee.

FIGS. 1A-C show increased PKCδII and Bcl2 expression in HT22 cells following treatment with exosomes from hASC.

FIGS. 2A-C show that exosomes from hASC are taken up by HT22 cells.

FIGS. 3A-B show that exosomes from hASC increase proliferation and survival in HT22 cells.

FIGS. 4A-B show that exosomes from hASC contain the lncRNA MALAT1.

FIGS. 5A-C show depletion of MALAT1 inhibits hASC exosome-mediated increase of PKCδII expression.

FIGS. 6A-D show MALAT1 promotes splicing of PKCδII via SRSF2.

FIGS. 7A-D show hASC exosomes and insulin treatment promotes neuronal proliferation and survival.

FIGS. 9A-C show that treatment with exosomes (TE) significantly rescued the TBI-associated motor deficits relative to TBI-Veh (T) and controls (C). Graphs show motor assessment using EBST (FIG. 9A), forelimb akinesia (FIG. 9B) and paw grasp test (FIG. 9C). Two-way ANOVA showed significant effects as follows: EBST, Treatment effects $F(4)=27.04$; Forelimb Akinesia Treatment effect $F(4)=30.3$; Paw grasp treatment effect $F(4)=42.2$. Post-hoc Bonferonni multiple comparisons are reported for differences versus TBI vehicle (T) #=p<0.01##=P<0.001. Treatment with exosomes depleted of MALAT1 (TEdM) did not improve motor performance on EBST and only improved forelimb akinesia and paw grasp at Day 3. Treatment with conditioned media depleted of exosomes (TdCM) also showed no improvement on EBST and only improved scores at Day 3 on the other 2 tasks. Groups: Sham N=11; TBI vehicle N=16; TBI exosomes N=16; TBI exosomes depleted of MALAT1 N=16; TBI conditioned media depleted of exosomes N=7.

FIGS. 9D-G show lesion assessment in mice. Treatment with exosomes derived from hASC's significantly reduces impact and peri-impact areas of rats after mild TBI. Nissl staining as shown in (FIG. 9F) was performed on Day 11 to assess damage to cortical region post TBI. Graphs (FIG. 9D) and (FIG. 9E) quantify the data from images. The panel shown in FIG. 9F demonstrates the methods for quantifying the impact area and for choosing images for analysis of the peri-impact area. Data for impact area (FIG. 9D) showed significant reduction in cortical lesion area following treatment with exosomes in the TE group and no rescue by of any other treatment. Representative images of sections used for quantifying impact area and peri-impact are shown in FIG. 9G. For the peri-impact area (FIG. 9E) there was a significant rescue in the TE group, whereas TEdM group displayed partial rescue of the peri-impact areas when compared with vehicle (T) and sham controls (C). Data in the bar graphs represent the mean±SEM values. Impact area $F=14.78$; Peri-Impact area $F=56.58$. Data were analyzed by one way ANOVA followed by Dunnet's multiple comparison test. # (p<0.1) ## (p<0.01).

(FIG. 11A) Imaging revealed exosomes migrating to the spleen, liver and lungs 1 hour after transplantation and migrating to the impact site of the brain on day 3 after TBI relative to sham controls. ex vivo analysis shows the fluorescent signal intensity was highest in the spleen and liver one hour after transplantation and gradually declined through day 11, whereas the lungs slightly increased after day 3 before declining through days 7 and 11. The brain impact site showed no apparent signal when compared to TBI-sham treatment animals one hour after exosome transplantation, but increased by day 3 where the signal remained through day 7 and only TEdM radiant efficiency declined by day 11. (FIG. 11B) Radiant efficiency is expressed as photons per second per square centimeter per steridian divided by microwatts per square centimeter(((p/s)/[cm)^2/sr)/(μW/[cm)^2)). Data represent the mean±SEM values N=3 per group.

FIGS. 12A-B show the hierarchical heat map of gene expression of (FIG. 12A) coding genes or (FIG. 12B) noncoding RNA from the RNAseq dataset. The gene clustering from the spleen is on the top and brain is the lower half of the dendrograms. For both (FIG. 12A) and (FIG. 12B) RPKM data from 19,058 detectable rat genes were used in analysis by hierarchical clustering with Gene Cluster 3.0. RPKMs were log-2-transformed and adjusted by centering genes using the median. Clustering was performed on genes and arrays using centered correlation as distance measure and average linkage as method. Data shows clusters of genes or noncoding RNA that are affected by TBI and restored towards the no TBI pattern with exosomes treatment.

FIGS. 15A-J show localization of exosomes and validation of MALAT1 and GFP levels. Localization of exosomes and MALAT1 to brain and spleen. Confocal imaging of exosome-positive expression of GFP in the brain and spleen of TBI rats. Images reveal migration of exosomes to both the contralateral and ipsilateral cortical region of the TBI-impacted brains near the impact site (FIG. 15A, B, D, E) and the spleen (FIG. 15C, F) of TE and TEdM rats as shown by detecting GFP expression (green) in cells with DAPI positive staining (blue) 11 days after transplantation. White arrows indicate cells with exosomes. There was higher migration to the ipsilateral cortex near the impact site than that observed in the contralateral cortex. Scale bar in F equals 50 microns. (FIG. 15G) MALAT1 expression was measured in hASC-isolated exosomes and isolated exosomes with MALAT1 knockdown. Relative to the MALAT1 level in hASC there is an increase in MALAT1 in the secreted exosomes, and this was knocked down significantly with the anti-sense oligonucleotide treatment. (FIG. 15H) endogenous MALAT1 levels in rat brain and spleen decrease with TBI: Following TBI and treatment with hASC exosomes, the levels of MALAT1 within the rat brain and spleen were analyzed by PCR using rat specific primers. RNA was extracted and samples were pooled from 4 rats each from the no TBI, TBI treated with vehicle and TBI treated with exosomes. Graph represents percent control with no TBI group designated as 100 percent. The experiment was repeated five times. The results were analyzed with two-tailed Student's t-test using PRISM4 statistical analysis software (GraphPad, San Diego, Calif.). A level of p<0.05 was considered statistically significant. * is p<0.0001 highly significant between control (no TBI) and TBI with vehicle treatment and between TBI and TBI treated with hASC exosomes for MALAT1. (FIG. 15I) Verification that hASC exosomes were taken up by brain and spleen: SYBR Green Real Time qPCR using human MALAT1 primers and (FIG. 15J) GFP primers was performed for absolute quantification. GAPDH served as control. For absolute quantification, a standard curve was generated for each gene in every assay. Absolute quantification of mRNA expression levels for MALAT1 and GFP was calculated by normalizing the values to GAPDH. The experiments were repeated four times with similar results. The results were analyzed with two-tailed Student's t-test using PRISM4 statistical analysis software (GraphPad, San Diego, Calif.). A level of p<0.05 was considered statistically significant. * is p<0.0001 highly significant between TBI treated with hASC exosomes and TBI treated with MALAT1-depleted (M1 aso) exosomes for MALAT1. The levels of GFP did not change with depletion of MALAT1.

FIGS. 16A-I show validation of RNA Seq data using qPCR. Real time qPCR validation of representative genes identified by RNA Seq data in cortex and spleen that are affected by TBI and treatment with exosomes. All assays were run in triplicate and data is expressed as the mean+/−

SEM. Data for each gene was analyzed by One-Way ANOVA followed by Dunnet's multiple comparison test. ## indicates that group was different from control p<0.01. ANOVA for each graph are IL1ß cortex (F(3, 8)=16008); TNFα cortex (F(3, 8)=5989); IFNG cortex (F(3, 8)=1784); TrkC cortex (F(3, 8)=814); IL10 cortex (F(3, 8)=2980); RABL6 spleen (F(3, 8)=4640); TNFα spleen (F(3, 8)=286); E2F4 spleen (F(3, 8)=516); PLAg2 spleen (F(3, 8)=451).

Figure 17:
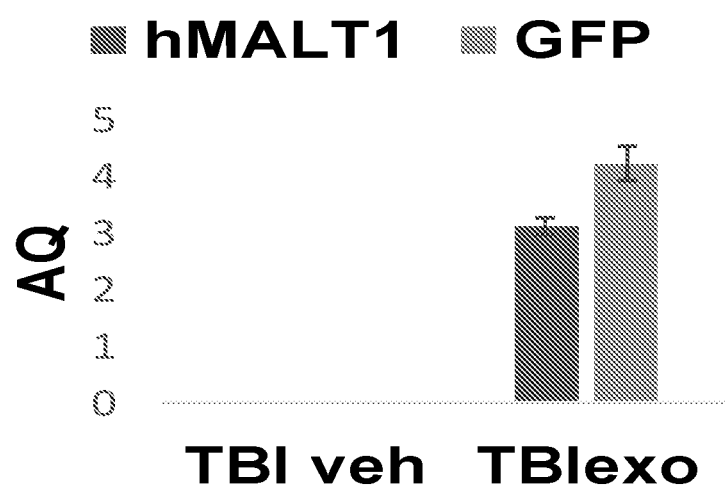

FIG. 17 shows brain levels of human MALAT1 and GFP (that was transfected into exosomes). Real time qPCR was performed for absolute quantitation of RNA. Exosomes were delivered intranasally 48 hours following injury. Human MALAT1 and GFP were detected in the cortex 7 days later. This validates that the intransal delivery route was successful in delivery of exosomes containing MALAT1 into the brain. No human MALAT1 or GFP were detected in the brain of vehicle (phosphate buffered saline) treated mice.

FIG. 18A-F show that intranasal hAS exosomes at 48 hours post CCI rescues injury. Groups of 10 C57BL/6 mice were subjected to CCI, a craniectomy with center point 2.0 ML, 2.0 AP from bregma was drilled 3.5 mm in diameter. Contusion was achieved using a 3.0 mm tip attached to an electromagnetic impactor (Leica). Impact parameters were: depth 0.95 mm from dura, velocity 4.0 m/s, dwell time 300 ms. Control mice received a craniectomy but no impact. Forty eight hours following CCI mice received either vehicle or hASCexo (10 μg total dose, intranasal 4 μl per nostril). There was a significant improvement in motor behaviors by day 3 that continued up to 7 days, forelimb akinesia recovery is seen by day 7 in the CCI group (FIGS. 18A-C). Cognitive assessment was done with the 6 arm RAWM. As can be observed mice perform more errors following CCI on blocks 3-5 and there is a rescue of this deficit following hASCexo (FIG. 18D). At the end of testing mice were euthanized and brains removed for histology or biochemistry. Lesion volume was reduced by 50% in the hASCexo treated mice (FIG. 18E). FIG. 18F demonstrates a reduction in expression of MHC II expressing microglia (thalamus), and GFAP expression (cortex) following intranasal exosome treatment. All statistics were done using two-way ANOVA, if ANOVA was significant this was followed by post-hoc analysis of simple effects across test days, ## indicates p<0.01.

FIGS. 19A-C shows merged confocal images of GFP labelled hASC exosomes with either NeuN (FIG. 19A), IBA1 (FIG. 19B) or GFAP (FIG. 19C) in the hippocampus following CHI. Numerous exosomes are found co-localized with neurons and microglia; however, few are observed in astrocytes. White arrows indicate the GFP localization.

FIG. 20 shows the top upstream regulators that fit the Pattern +1 and −1 for brain and spleen.

DETAILED DESCRIPTION

Adult stem cells have the potential for healing dermal wounds, pressure sores, as well as promoting survival of neurons after injury. Stem cells residing in the adipose tissue have significant advantages due to ease of isolation, ability to obtain large quantities, and potential of personalized regenerative medicine. However, direct injection of hASC to the site of injury may result in growth and integration of stem cells into neurons, which may be detrimental to the brain.

Human adipose-derived stem cells secrete factors in their secretome that function in a paracrine manner to enhance cell survival and proliferation. The secretome content is rich in proteins and RNA, which are transported in vesicles and smaller exosomes to the recipient cells where they exert their effects. The secretome contains micro-vesicles amongst which exosomes are the smallest vesicles at 50-100 nM in diameter.

The present disclosure describes a method of treating brain injury in a subject, comprising administering to the subject a composition comprising exosomes isolated from human adipose-derived stem cells.

1. Definitions

Unless otherwise defined, all technical and scientific terms used herein have the same meaning as commonly understood by one of ordinary skill in the art. In case of conflict, the present document, including definitions, will control. Preferred methods and materials are described below, although methods and materials similar or equivalent to those described herein can be used in practice or testing of the present invention. All publications, patent applications, patents and other references mentioned herein are incorporated by reference in their entirety. The materials, methods, and examples disclosed herein are illustrative only and not intended to be limiting.

For the recitation of numeric ranges herein, each intervening number there between with the same degree of precision is explicitly contemplated. For example, for the range of 6-9, the numbers 7 and 8 are contemplated in addition to 6 and 9, and for the range 6.0-7.0, the number 6.0, 6.1, 6.2, 6.3, 6.4, 6.5, 6.6, 6.7, 6.8, 6.9, and 7.0 are explicitly contemplated.

The use of the terms "a" and "an" and "the" and "at least one" and similar referents in the context of describing the invention (especially in the context of the following claims) are to be construed to cover both the singular and the plural, unless otherwise indicated herein or clearly contradicted by context. The use of the term "at least one" followed by a list of one or more items (for example, "at least one of A and B") is to be construed to mean one item selected from the listed items (A or B) or any combination of two or more of the listed items (A and B), unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

The modifier "about" used in connection with a quantity is inclusive of the stated value and has the meaning dictated by the context (for example, it includes at least the degree of error associated with the measurement of the particular quantity). The modifier "about" should also be considered as disclosing the range defined by the absolute values of the two endpoints. For example, the expression "from about 2 to about 4" also discloses the range "from 2 to 4." The term "about" may refer to plus or minus 10% of the indicated number. For example, "about 10%" may indicate a range of 9% to 11%, and "about 1" may mean from 0.9-1.1. Other meanings of "about" may be apparent from the context, such as rounding off, so, for example "about 1" may also mean from 0.5 to 1.4.

The term "administration" or "administering" is used throughout the specification to describe the process by which the disclosed exosome compositions may be delivered to a subject. Administration will often depend upon the amount of composition administered, the number of doses, and duration of treatment. Multiple doses of the composition may be administered. The frequency and duration of administration of the composition can vary, depending on any of a variety of factors, including patient response, etc. The exosome compositions may be administered to the subject by any suitable route. For example, the compositions may be administered orally, parenterally, (including intravenous, subcutaneous, topical, transdermal, intradermal, transmucosal, intraperitoneal, intramuscular, intracapsular, intraorbital, intracardiac, transtracheal, subcutaneous, subcuticular, intraarticular, subcapsular, subarachnoid, intraspinal, and epidural injection) by infusion, by electroporation, or co-administered as a component of any medical device or object to be inserted (temporarily or permanently) into a subject. For example, the exosome compositions may be administered intranasally.

The term "brain injury" as used herein refers to any injury to the brain. The brain injury may be a traumatic brain injury, caused by an external force to the head. For example, the traumatic brain injury may be a diffuse axonal injury, a concussion, a contusion, a coup-countrecoup injury, a recurrent traumatic brain injury (sometimes referred to as second impact syndrome), an open head injury, a closed head injury, a penetrating injury, Shaken Baby Syndrome, Locked in Syndrome, and the like. The brain injury may be an anoxic brain injury, caused by a complete interruption of the supply of oxygen to the brain. The brain injury may be a hypoxic brain injury, caused by inadequate supply of oxygen to the brain. Examples of anoxic and hypoxic brain injuries include, but are not limited to, hypoxic ischemic encephalopathy, diffuse cerebral hypoxia, focal cerebral ischemia, global cerebral ischemia, and cerebral infarction.

The terms "comprise(s)," "include(s)," "having," "has," "can," "contain(s)," and variants thereof, as used herein, are intended to be open-ended transitional phrases, terms, or words that do not preclude the possibility of additional acts or structures. The singular forms "a," "and," and "the" include plural references unless the context clearly dictates otherwise. The present disclosure also contemplates other embodiments "comprising," "consisting of," and "consisting essentially of," the embodiments or elements presented herein, whether explicitly set forth or not.

The term "exosome" as used herein refers to a microvesicle of 50-100 nM diameter. The exosomes of the present invention are secreted from human adipose-derived stem cells.

The terms "exosome composition", "composition", and "pharmaceutical composition" are used interchangeably herein to refer to a composition comprising exosomes isolated from hASCs.

A "pharmaceutically acceptable excipient," "pharmaceutically acceptable diluent," "pharmaceutically acceptable carrier," or "pharmaceutically acceptable adjuvant" as used herein means an excipient, diluent, carrier, and/or adjuvant that are useful in preparing a pharmaceutical composition that are generally safe, non-toxic and neither biologically nor otherwise undesirable, and include an excipient, diluent, carrier, and adjuvant that are acceptable for veterinary use and/or human pharmaceutical use, such as those promulgated by the United States Food and Drug Administration.

The term "sample" as used herein refers to any physical sample that includes a cell or a cell extract from a cell, a tissue, or an organ including a biopsy sample. The sample can be from a biological source such as a subject or animal, or a portion thereof, or can be from a cell culture. Samples from a biological source can be from a normal or an abnormal organism, such as an organism known to be suffering from a condition or a disease state such as a neoplasm, or any portion thereof. Samples can also be from any fluid, tissue or organ including normal and abnormal (diseased or neoplastic) fluid, tissue or organ. Samples from a subject or animal can be used in the present invention as obtained by the subject or animal and processed or cultured such that cells from the sample can be sustained in vitro as a primary or continuous cell culture or cell line.

"Subject" and "patient" as used herein interchangeably refers to any vertebrate, including, but not limited to, a mammal (e.g., cow, pig, camel, llama, horse, goat, rabbit, sheep, hamsters, guinea pig, cat, dog, rat, and mouse, a non-human primate (for example, a monkey, such as a cynomolgous or rhesus monkey, chimpanzee, etc.) and a human). The subject may be a human or a non-human. The subject or patient may be undergoing other forms of treatment.

A "therapeutically effective amount," or "effective dosage" or "effective amount" as used interchangeably herein unless otherwise defined, means a dosage of a drug effective for periods of time necessary, to achieve the desired therapeutic result.

In accordance with the present invention, a suitable single dose size is a dose that is capable of preventing or alleviating a symptom in a subject when administered one or more times over a suitable time period. An effective dosage may be determined by a person skilled in the art and may vary according to factors such as the disease state, age, sex, and weight of the individual, and the ability of the drug to elicit a desired response in the individual. Therapeutically effective amounts for the disclosed exosome compositions can be readily determined by those of ordinary skill in the art.

A therapeutically effective amount may be administered in one or more administrations (e.g., the exosome composition may be given as a preventative treatment or therapeutically at any stage of brain injury, before or after symptoms, and the like), applications or dosages and is not intended to be limited to a particular formulation, combination or administration route. It is within the scope of the present disclosure that the disclosed exosome compositions may be administered at various times during the course of treatment of the subject. The times of administration and dosages used will depend on several factors, such as the disease state, age, sex, and weight of the individual, and the ability of the composition to elicit a desired response in the individual. Administration may be adjusted according to individual need and professional judgment of a person administrating or supervising the administration of the compounds used in the present invention.

The term "treatment", "treat", "treating" or any grammatical variation thereof as used herein, includes but is not limited to, ameliorating or alleviating a symptom of a disease or condition, reducing, preventing, suppressing, inhibiting, lessening, or affecting the progression and/or severity of an undesired physiological change or a diseased condition. For example, treatment may include promoting regeneration of neurons following brain injury. Treatment may include enhancing survival of neurons following brain injury. Treatment may include decreasing wound size after a brain injury. Treatment may include complete elimination of the wound following brain injury.

2. Exosome Compositions

The disclosure provides compositions comprising exosomes isolated from human adipose-derived stem cells. The exosomes may be obtained or isolated from hASCs by any suitable method known in the art. The exosome composition may further comprise insulin.

The exosome composition may further comprise a pharmaceutically acceptable carrier or excipient. Pharmaceutically acceptable carriers typically include at least one of diluents, lubricants, binders, disintegrants, colorants, flavors, sweeteners, antioxidants, preservatives, glidants, solvents, suspending agents, wetting agents, surfactants, pH adjusting additives, combinations thereof, and others. The route by which the disclosed compounds are administered and the form of the composition will dictate the type of carrier to be used.

Such pharmaceutical carriers may be sterile liquids, such as water and oils. For example, the carrier may be a petroleum oil such as mineral oil; vegetable oil such as peanut oil, soybean oil, or sesame oil; animal oil; or oil of synthetic origin. Suitable carriers also include ethanol, dimethyl sulfoxide, glycerol, silica, alumina, starch, sorbitol, inositol, xylitol, D-xylose, mannitol, powdered cellulose, microcrystalline cellulose, talc, colloidal silicon dioxide, calcium carbonate, magnesium carbonate, calcium phosphate, calcium aluminium silicate, aluminium hydroxide, sodium starch phosphate, lecithin, and equivalent carriers and diluents. Saline solutions and aqueous dextrose and glycerol solutions can also be employed as liquid carriers. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol, and the like. The exosome composition may contain minor amounts of wetting or emulsifying agents. The exosome composition may contain pH buffering agents.

The exosome composition may be in a variety of forms. For example, the exosome composition may be in solid form, semi-solid form, or a liquid dosage forms. The exosome composition may be in the form of tablets, pills, powders, liquid solutions or suspensions, suppositories, and injectable or infusible solutions. The preferred form depends on the intended mode of administration and therapeutic application. For example, the exosome composition may be in liquid form for intravenous administration. As another example, the exosome composition may in a form suitable for intranasal administration. For example, the exosome composition may be formulated as an ointment, cream, suspension, lotion, powder, solution, past, gel, spray, aerosol, or oil for intranasal administration.

3. Methods of Treating Brain Injury

The invention discloses a method of treating brain injury in a subject. The method of treating brain injury in a subject may comprise administering the exosome composition to the subject.

The subject may be any vertebrate, including, but not limited to, a mammal (e.g., cow, pig, camel, llama, horse, goat, rabbit, sheep, hamsters, guinea pig, cat, dog, rat, and mouse, a non-human primate (for example, a monkey, such as a cynomolgous or rhesus monkey, chimpanzee, etc.) and a human). The subject may be a human or a non-human. The subject or patient may be undergoing other forms of treatment.

The subject may be diagnosed with brain injury. The brain injury may be a traumatic brain injury, caused by an external force to the head. For example, the traumatic brain injury may be a diffuse axonal injury, a concussion, a contusion, a coup-countrecoup injury, a recurrent traumatic brain injury (sometimes referred to as second impact syndrome), an open head injury, a closed head injury, a penetrating injury, Shaken Baby Syndrome, Locked in Syndrome, and the like. The brain injury may be an anoxic brain injury, caused by a complete interruption of the supply of oxygen to the brain. The brain injury may be a hypoxic brain injury, caused by inadequate supply of oxygen to the brain. Examples of anoxic and hypoxic brain injuries include, but are not limited to, hypoxic ischemic encephalopathy, diffuse cerebral hypoxia, focal cerebral ischemia, global cerebral ischemia, and cerebral infarction.

The exosome composition may be administered to the subject by any suitable route. The exosome composition may be administered orally, parentally (including intravenous, subcutaneous, topical, transdermal, intradermal, transmucosal, intraperitoneal, intramuscular, intracapsular, intraorbital, intracardiac, transtracheal, subcutaneous, subcuticular, intraarticular, subcapsular, subarachnoid, intraspinal, and epidural injection) by infusion, by electroporation, or co-administered as a component of any medical device or object to be inserted (temporarily or permanently) into a subject. For example, the exosome composition may be administered intransally. As another example, the exosome composition may be administered intravenously.

The exosome composition may be administered independently to the subject. The exosome composition may be administered to the subject in combination with insulin. For example, the composition administered to the subject may comprise exosomes isolated from human adipose-derived stem cells and insulin. The exosome composition and insulin may be administered simultaneously to the subject. The exosome composition and insulin may be administered separately to the subject. For example, insulin may be administered to the subject at a different site from the exosome composition. As another example, insulin may be administered to the subject by a different route than the exosome composition. The exosome composition and the insulin may be administered sequentially to the subject. For example, insulin may be administered to the subject before the exosome composition. Insulin may be administered to the subject after the exosome composition. Sequential administration may involve treatment with insulin on the same day (within 24 hours) of treatment with the exosome composition. Sequential administration may also involve continued treatment with insulin on days that the exosome composition is not administered.

The exosome composition may be administered in combination with other therapies for the treatment of brain injury. Other therapies may include emergency treatments, such as removing clotted blood from the brain, repairing skull fractures, and relieving pressure in the skull. Other therapies may include medications to treat symptoms of the brain injury. Other therapies may include medications to reduce other risks associated with brain injury. For example, the exosome composition may be administered in combination with anti-anxiety medications, anticoagulants, anticonvulsants, antidepressants, diuretics, muscle relaxants, stimulants, and the like. Other therapies may include rehabilitation therapies, including physical therapy, occupational therapy, speech therapy, cognitive therapy, and the like.

Administration of the exosome composition may be as a single dose, or multiple doses over a period of time. The exosome composition may be administered to the patient at any frequency necessary to achieve the desired therapeutic effect. For example, the exosome composition may be administered once to several times every month, every two weeks, every week, or every day. Administration of the exosome composition may be repeated until the desired therapeutic effect has been achieved. For example, the exosome composition may be administered once to several times over the course of 1 day, 3 days, 5 days, 1 week, 2 weeks, 3 weeks, 1 month, 2 months, 3 months, 4 months, 5 months, 6 months, 7 months, 8 months, 9 months, 10 months, 11 months, 12 months, or more.

The amount of the exosome composition to be administered may depend on a variety of factors, such as the route of administration and the seriousness of the condition, and should be decided according to the judgment of the practitioner and each patient's circumstances. The exosome composition may be administered in any amount suitable for the treatment of brain injury in a subject. An effective amount of the exosome composition may cause a partial improvement or a complete elimination of symptoms due to brain injury. Treatment may include promoting renegeration of neurons following brain injury. Treatment may include enhancing survival of neurons following brain injury. Treatment may include decreasing wound size after a brain injury. Treatment may include complete elimination of the wound following brain injury.

Suitable dosage ranges of the exosome composition include from about 0.001 µg exosome/kg body weight to about 100 mg/kg, about 0.01 µg/kg to about 90 mg/kg, about 0.1 µg/kg to about 80 mg/kg, about 1 µg/kg about 70 mg/kg, about 10 g/kg to about 60 mg/kg, about 0.1 mg/kg to about 50 mg/kg, about 0.5 mg/kg to about 25 mg/kg, about 1 mg/kg to about 10 mg/kg, or about 2.5 mg/kg to about 5 mg/kg. For example, suitable dosage ranges of the exosome composition include about 0.001 µg/kg, about 0.01 µg/k, about 0.1 µg/k, about 1 µg/k, about 10 µg/kg, about 0.1 mg/kg, about 0.5 mg/kg, about 1 mg/kg, about 2.5 mg/kg, about 5 mg/kg, about 10 mg/kg, about 15 mg/kg, about 20 mg/kg, about 25 mg/kg, about 30 mg/kg, about 40 mg/kg, about 50 mg/kg, about 60 mg/kg, about 70 mg/kg, about 80 mg/kg, about 90 mg/kg, or about 100 mg/kg.

Suitable dosage ranges of insulin include from about 0.001 µg insulin/kg body weight to about 100 mg/kg, about 0.01 µg/kg to about 90 mg/kg, about 0.1 µg/kg to about 80 mg/kg, about 1 µg/kg about 70 mg/kg, about 10 g/kg to about 60 mg/kg, about 0.1 mg/kg to about 50 mg/kg, about 0.5 mg/kg to about 25 mg/kg, about 1 mg/kg to about 10 mg/kg, or about 2.5 mg/kg to about 5 mg/kg. For example, suitable dosage ranges of insulin include about 0.001 µg/kg, about 0.01 µg/k, about 0.1 g/k, about 1 µg/k, about 10 g/kg, about 0.1 mg/kg, about 0.5 mg/kg, about 1 mg/kg, about 2.5 mg/kg, about 5 mg/kg, about 10 mg/kg, about 15 mg/kg, about 20 mg/kg, about 25 mg/kg, about 30 mg/kg, about 40 mg/kg, about 50 mg/kg, about 60 mg/kg, about 70 mg/kg, about 80 mg/kg, about 90 mg/kg, or about 100 mg/kg.

In addition, in vitro assays may optionally be employed to help identify optimal dosage ranges. Effective doses may be extrapolated from dose-response curves derived from in vitro or animal model test systems.

4. Mechanism of Action

Protein kinase C (PKC) is a family of serine/threonine kinases with 11 isoforms. The PKC family is subdivided into three groups based upon their activation by calcium, phosphatidyl serine, diacyl glycerol or phorbol esters: classical or conventional PKCs ($\alpha$, $\beta$I, $\beta$II and $\gamma$), novel PKCs ($\delta$, $\epsilon$, $\eta$ and $\theta$) and atypical PKCs ($\zeta$, $\lambda/\tau$). Activation of these proteins in the brain is essential for learning, synaptogenesis, and neuronal survival. In particular, PKC$\delta$, a novel PKC, has been implicated in memory, neuronal proliferation and activation of survival pathways. PKC$\delta$ is alternatively spliced to PKC$\delta$I (ubiquitous expression in human, mouse and rat), PKC$\delta$II, IV, V, VI, VII (mouse-specific splice variants). PKC$\delta$III (rat specific splice variant) and PKC$\delta$VIII (human specific splice variant). In mouse, PKC$\delta$II is generated via alternative 5' splice site usage of exon 9 and functions as a pro-survival kinase.

Exosomes isolated from hASC CM contain many non-coding RNAs. Long noncoding RNAs (lncRNAs) have varied functions including signaling, molecular decoys, scaffolding and guiding ribonucleoprotein complexes. The lncRNA metastasis associated lung adenocarcinoma transcript 1 (MALAT1), sometimes referred to as NEAT2, was first reported in tumors and is shown to regulate alternative splicing of genes and function as transcriptional regulator, as well as plays a role in cell cycle and cellular mitosis. MALAT1 regulates alternative splicing of several genes including CAMK2B, CDK7, SAT1, HMG2L1, BMYB, MGEA6. In addition, MALAT1 associates with SRSF2 splicing domains in multiple mammalian species. The lncRNA NEAT1 is also shown to regulate alternative splicing of genes. NEAT1 is present in the conditioned media of hASC; however it is not present within the exosomes. It may be possible that NEAT1 is packaged in other vesicles. HT22 cells take up exosomes and that exosomes from hASC increases neuronal survival and proliferation.

The present disclosure identifies exosomes as the important component of the secretome that increases neuronal survival following injury. An advantage to identifying exosomes as the important component of the secretome that increases neuronal survival is that directly injecting hASC to neuronal site of injury may result in growth and integration of stem cells into neurons, which may be detrimental to the brain. Without wishing to be bound by theory, the results below indicate that MALAT1 is an important component of hASC exosomes. These results promise the development of therapeutic regiments targeted to specific areas of neuronal injury and degeneration. However, the usage of MALAT1 in a systemic manner would be discouraged in order to avoid possible malignancy promoting effects of lncRNAs.

MALAT1 locates to the nuclear speckles where it interacts with the pre-mRNA to regulate splicing. The data presented herein using RIP assays shows that MALAT1 associates with SRSF2 in the nuclear fraction. MALAT1 sequesters SRSF2 and promotes its phosphorylation in the RS domain. SRSF2 regulates PKC$\delta$II expression. The results presented herein indicate that MALAT1 from hASC exosomes recruits SRSF2 to regulate PKC$\delta$II alternative splicing in HT22 neuronal cells. In addition, present disclosure indicates that insulin treatment dramatically increases association of SRSF2 with MALAT1. These studies demonstrate that MALAT1 binds tightly to SRSF2 such that kinases may efficiently phosphorylate SRSF2 to promote alternative splicing of PKC$\delta$II in HT22 cells. The data presented herein further indicates that hASC exosomes improved neuronal survival and proliferation to a higher extent than insulin alone; combination treatment of hASC exosomes and insulin further enhanced the ability of hASC to increase neuronal survival. These results show a promise of using hASC exosomes with insulin in models of traumatic brain injury or other neurodegenerative diseases. Without wishing to be bound by theory, the present disclosure study provides the potential mechanism of action of hASC and its secretome in neuronal survival and identifies MALAT1 as a central lncRNA in hASC exosomes and neuronal regenerative medicine. It is also important to note that MALAT1 may have additional targets that play a role in neuronal survival and proliferation. Additionally, apart from MALAT1, other components of the exosomes may contribute to increased neuronal survival.

5. Kits

The invention further discloses a kit, which may be used to treat brain injury in a subject. The kit comprises at least the exosome composition. Instructions included in kits may be affixed to packaging material or may be included as a package insert. While the instructions are typically written or printed materials they are not limited to such. Any medium capable of storing such instructions and communicating them to an end user is contemplated by this disclosure. Such media include, but are not limited to, electronic storage media (e.g., magnetic discs, tapes, cartridges, chips), optical media (e.g., CD ROM), and the like. As used herein, the term "instructions" may include the address of an internet site that provides the instructions.

6. Examples

The disclosed compounds, compositions and methods will be better understood by reference to the following examples, which are intended as an illustration of and not a limitation upon the scope of the invention. Where the term comprising is used herein, it should be understood that the disclosure also contemplates alternative embodiments consisting of or consisting essentially of the recited features.

Example 1: Methods

The University of South Florida Institutional Animal Care and Use Committee (IACUC) approved all experimental procedures with animals. All rats were housed under normal conditions (20° C., 50% relative humidity, and a 12 h light/dark cycle). All studies were performed by personnel blinded to the treatment condition.

Cell Culture:

The studies were carried out using immortalized clonal mouse hippocampal cell line (HT22) obtained from Dr. D. R. Schubert (Salk Institute). HT22 cells were cultured in 75 cm2 flasks in DMEM supplemented with 10%-heat-inactivated fetal bovine serum (FBS), 1% penicillin/streptomycin (50 U/ml) and 2 mM glutamine. Cells were maintained at 37° C. in a humidified incubator containing 5% $CO_2$. HT22 cells were sub-cultured into either 25 $cm_2$ flasks or 100 $mm_2$ dishes and used for experiments at 60-80% confluence.

Western Blot Analysis:

Cell lysates (40 μg) were separated on 10% polyacrylamide gel electrophoresis-SDS (PAGESDS). Proteins were electrophoretically transferred to nitrocellulose membranes, blocked with Tris buffered saline-0.1% Tween 20 containing 5% nonfat dried milk, washed, and incubated with a polyclonal antibody against either anti-Bcl2 (Cell Signaling) or PKCδII-specific polyclonal antibody (Patel laboratory (4)). Anti-GAPDH was purchased from Cell Signaling. Following incubation with anti-rabbit IgG-HRP, enhanced chemiluminesence (Pierce™) was used for detection. Images were digitally captured by ProteinSimple FluorChem™ and densitometric analysis was performed using AlphaView™ Software.

Transient Transfection of Plasmid DNA:

hASC were trypsinized and cell pellets were collected in 100 μL Nucleofector® solution (Lonza) and combined with pMAX GFP (2 μg. The cell/DNA solution was transferred to a cuvette and the program initiated (0.34 kV, 960 microfarads). Medium (500 μL) was added immediately and cells were gently transferred to 60 mm plates and allowed to grow for 24 hours or more according to the experiment.

siRNA Transfection—Two siRNAs that target separate areas were used to knockdown expression of SRSF2. SRSF2 siRNAs (IDs: 12628 and 12444) along with its scrambled control were purchased from Ambion and transfected using Ambion's siRNA transfection kit. These were validated for specificity to eliminate off-target gene effects. Ambion's PARIS kit (catalog 1921) was used to simultaneously isolate proteins and RNA to verify knockdown by siRNA transfection.

Quantitative Real-Time qPCR:

Total RNA was isolated from cells using RNA-Bee™ (Tel Test, Inc) as per manufacturer's instructions. 2 μg of RNA was used to synthesize first strand cDNA using random hexamer primers and Omniscript™ kit (Qiagen). 1 μL of cDNA was amplified by real-time quantitative PCR using Maxima SYBR Green/Rox qPCR master mix (Thermo Scientific) in an ABI ViiA7 sequence detection system (PE Applied Biosystems) to quantify the relative levels of the transcripts in the samples. The primers are: PKCδI sense primer 5'-ACATCCTAGACAACAACGGGAC-3' (SEQ ID NO: 1) and anti-sense 5'-ACCACGTCCTTCTTCAGA-CAC-3' (SEQ ID NO: 2); PKCδII sense primer 5'-CAC-CATCTTCCAGAAAGAACG-3' (SEQ ID NO: 3) and anti-sense 5'-TCGCAGGTCTCACTACTGCCTTTTCC-3' (SEQ ID NO: 4); GAPDH sense primer 5'-TGACGTGCCGC-CTGGAGAAAC-3' (SEQ ID NO: 5) and anti-sense 5'-CCGGCATCGAAGGTGGAAGAG-3' (SEQ ID NO: 6); human MALAT1 sense: 5'-GAGTTCTAATTCTTTTTACT-GCTCAATC-3' (SEQ ID NO: 7) and antisense 5'-TCAAGT-GCCAGCAGACAGCA-3' (SEQ ID NO: 8); mouse MALAT1 sense: 5'-TGCAGTGTGCCAATGTTTCG-3' (SEQ ID NO: 9) and antisense 5'-GGCCAGCTG-CAAACATTCAA-3' (SEQ ID NO: 10); UlsnRNA sense: 5'-TCCCAGGGCGAGGCTTATCCATT-3' (SEQ ID NO: 11) and antisense 5'-GAACGCAGTCCCCCACTACCA-CAAAT-3' (SEQ ID NO: 12). Amplification was performed on the ViiaA 7 (Applied Biosystems). Real-time PCR was then performed in triplicate on samples and standards. The plate setup included a standard series, no template control, no RNA control, no reverse transcriptase control, and no amplification control. After primer concentrations were optimized to give the desired standard curve and a single melt curve, relative quotient (RQ) was determined using the AACT method with U6snRNA or GAPDH as the endogenous control and HT22 control samples as the calibrator sample. Experiments were repeated four times.

Absolute Quantification:

A standard curve was generated for each gene in every assay. To do so, 100 ng to 0.4 ng of RNA were reverse-transcribed as described above. The resulting cDNA was used to obtain a standard curve correlating the amounts with the threshold cycle number ($C_t$ values). A linear relationship ($r_2>0.96$) was obtained for each gene. Real time PCR was then performed on samples and standards in triplicates. The plate setup also included a standard series, no template control, no RNA control, no reverse transcriptase control and no amplification control. The dissociation curve was analyzed for each sample. Absolute quantification of mRNA expression levels for PKCδI and PKCδII was calculated by normalizing the values to GAPDH.

Adipose-Derived Stem Cells:

White adipose tissue was obtained as discarded tissue from surgeries performed at Tampa General Hospital by Dr. Murr. Donors consented to their waste tissue to be used in research. The lean adipose tissue samples were obtained from subcutaneous depot of a female donor with BMI of 21.3 Subject was non-diabetic, non-smoker and did not have any form of cancer. The de-identified samples were obtained under an Institutional Review Board approved protocol (University of South Florida IRB #20295) with a "not human research activities determination" and was transported to the laboratory and processed within 24h of collection. Adipose tissue was cut up into small pieces and digested with 0.075% collagenase Type 1 (Worthington) in modified PBS for 2 h at 37° C. The suspension was filtered and centrifuged at 400 g at room temperature. The pellet contains the stromal vascular fraction (SVF). The pellet was resuspended in 1 mL of the erythrocyte lysis buffer (Stem Cell Technologies) for 10 min and washed in 20 mL of PBS with 2% P/S/A before centrifugation, 300-500 g, 5 min. The supernatant was aspirated and the cell pellet resuspended in a 3 mL stromal medium (α-MEM; Mediatech) with 20% FBS, 1% 1-glutamine (Mediatech), 1% P/S/A. Following three rinses in the stromal medium, SVF cells were plated for initial cell culture at 37° C. with 5% CO2 in HASC medium from ZenBio™ (Cat # PM-1). Subconfluent cells were passaged by trypsinization. Conditioned media (CM) was collected after 24-48 hours. Experiments were conducted within passages 2-3.

Exosome Isolation:

Conditioned media (CM) derived from hASC was collected after 48h and centrifuged at 3000 g for 15 min to remove dead cells. ExoQuick™ (SBI) reagent was added to the CM and incubated overnight at 4° C. Following centrifugation at 1500 g for 30 min, the pellet was further processed. ExoCap™ (JSR Life Sciences) composite reagent containing magnetic beads for CD9, CD63 and CD81 was used to purify exosomes. Exosomes were eluted from beads using the manufacturer's elution buffer and used in experiments as described.

RNA-Immunoprecipitation (RIP) Assay:

The RIP kit was purchased from Sigma and protocol followed as per manufacturer's instruction. SRSF2 antibody and SNRNP70 antibody were purchased from Millipore, and IgG antibody was included in kit (Sigma). Cell lysate (10%) was removed for input sample. Immunoprecipitation was performed with 2 µg SRSF2 antibody, snRNP70 antibody (positive control) or IgG antibody (as negative control). RNA was purified and treated with DNAse to remove genomic DNA. SYBR Green Real-time qPCR was performed as described above using MALAT1 primer sets and primers for U1 RNA, the binding partner for the positive control SNRNP70. The yield (% input) and specificity (fold enrichment) was calculated using Excel™ template for RIP from Sigma.

Cell Survival Assay:

WST-1 (Roche Molecular Biochemicals, IN) was added to HT22 cells (in triplicate) in the presence of hASC exosomes (10 µg) to a final concentration of 10% (vol/vol). Cells were incubated for 2 hours at 37° C. The formazon dye produced by viable cells is quantified using a spectrophotometer set at a wavelength of 440 nm and absorbance recorded for each well (reference wavelength 690 nm).

Cell Proliferation Assay:

HT22 cells were treated with hASC exosomes (10 µg). The treatments were performed in triplicate in a 48-well plate. The BrdU cell proliferation assay kit was purchased from Millipore, Catalog #2750 and used as per manufacturer's instructions to quantitatively evaluate the number of actively proliferating cells. Briefly, 100 µl BrdU was added per well of the 48 well plate and incubated overnight. BrdU incorporation was detected using peroxidase conjugate. The plate was read using spectrophotometer microplate reader set at dual wavelength of 450 nm/550 nm. The results were normalized against the blank and background readings.

Cell Migration Assay:

Scratch assay is an established method to measure cell migration and wound healing in vitro. HT22 cells were plated in 35 mm dishes. After 24 h, the cell monolayer was scraped with a P100 pipette tip creating a scratch. Cell debris was removed by washing with culture medium. Parallel lines on the outside surface of the dish were made to mark boundaries and create reference points. The cells were treated with hASC exosomes (10 µg) or insulin (10 nM) as indicated in the experiments. Nikon microscope was used to capture phase contrast images at 24h at original magnification ×20. Five separate fields of 1 $\mu m_2$ were counted for each plate for migration distances and averaged to determine overall scratch width after 24h post treatments compared to control. Experiments were repeated thrice.

Immunochemistry:

HT22 cells were plated in 8 well chamber plates and were either treated with exosomes from hASC and with or without 10 nM insulin treatment. After 24h, medium was removed, cells washed three times with PBS and fixed with 4% paraformaldehyde for 30 min. Cells rinsed with PBS and blocked with 1% BSA for 30 min. Primary antibodies for either Ki-67 or doublecortin were incubated overnight at 4° C. Cells were washed three times with PBS and were incubated with secondary fluorescent antibody for 1 hour at room temperature. To visualize nucleus, cells were stained with DAPI for 15 minutes at room temperature.

Statistical Analysis:

The gels were densitometrically analyzed using AlphaView™ software (ProteinSimple™). PRISM™ software was used for statistical analysis. A level of p<0.05 was considered statistically significant. The results are expressed as mean±SEM or as percent exon inclusion.

Exosome Isolation and Collection from ASCs:

hASC (Zenbio, catalog # ASC-F) were trypsinized and cell pellets were collected in 100 µL Nucleofector® kit (Lonza, catalog # VPE-1001) and combined with pMAX GFP (2 µg). The cell/DNA solution was transferred to a cuvette and the program initiated (0.34 kV, 960 microfarads). Medium (500 µL) was added immediately and cells were gently transferred to 100 mm plates and allowed to grow for 48 hours. To deplete MALAT from hASC exosomes, MALAT1 antisense oligonucleotide ID: 39524 ASO from Ionis Pharmaceuticals was used, validated for specificity and designed for efficient uptake by cells. The ASOs were added to hASC 48 hours. Exosomes were isolated from conditioned media. The expression levels of MALAT1 were determined in the exosomes using human MALAT1 primers in qPCR. 100 µg of exosomes were injected into each rat for treatment. Conditioned media (CM) derived from hASC was collected after 48h and centrifuged at 3000 g for 15 min to remove dead cells. Exosomes were isolated and verified that exosomes contain GFP. ExoQuick™ (System Biosciences, Catalog # EXOTC-50A-1) reagent was added to the CM and incubated overnight at 4° C. along with XenoLight 1,1- dioctadecyl-3,3,3,3-tetramethylindotricbocyanine iodide (DiR) (catalog #125964; Caliper Life Sciences). Following centrifugation at 1500 g for 30 min, the pellet was further processed. ExoCap™ (JSR Life Sciences, Catalog # EX-COM) composite reagent containing magnetic beads for CD9, CD63 and CD81 was used to purify exosomes. Exosomes were eluted from beads using 500 μL of the manufacturer's elution buffer. Buffer exchange by Ambicon columns. Nanoparticle tracking analysis from NanoSight (NTA3.1, Build 3.1.46 RRID SCR-014239) was used to analyze peak diameter and concentration of exosomes obtained from 106 hASC. Analysis showed exosomes size to be 89±7 nm.

Animal Model and Surgical Procedures:

A total of 79 Fisher 344 male rats were subjected to either mild TBI by controlled cortical impact injury model or no TBI in the case for the sham surgery only control group. The rats were randomly distributed into the following groups: Surgery with no TBI (Sham control C, N=11), TBI with unconditioned media as vehicle (T; N=20), TBI treated with exosomes (TE, N=18), TBI treated with exosomes depleted of MALAT1 (TEdM, N=20), TBI with injection of conditioned media depleted of exosomes (TdCM; N=7). Deep anesthesia was administered to all rats undergoing TBI surgery using 1-2% isoflurane in nitrous oxide/oxygen (69%/30%) and was maintained using a gas mask. TBI induced animals were fixed in a stereotaxic frame (David Kopf Instruments). The TBI procedure was performed as follows: the skull was exposed by a midline incision, coordinates of +0.2 mm anterior and +0.2 mm lateral to the midline were found and craniotomy performed, the brain was then impacted at the frontoparietal cortex with a velocity of 6.0 m/s reaching a depth of 0.5 mm (mild TBI) below the dura matter layer for 150 ms. Body temperature of the animals was maintained within normal limits by a computer-operated thermal pad and rectal thermometer. All animals were closely monitored postoperatively and analgesic ketoprofen was administered prior to surgery and as needed thereafter. Rats were maintained on regular rodent diet throughout the experiment Intravenous Administration of Exosomes and CM:

Three hours after TBI surgical procedures, rats were anesthetized using 1-2% isoflurane in nitrous oxide/oxygen (69%/30%) and was maintained using a gas mask. Intravenous injections through the jugular vein were divided as follows: TBI-Veh (T) received 500 μl unconditioned media, TBI animals with exosomes depleted conditioned media (TdCM) group received 500 μl conditioned media depleted of exosomes, TBI animals with exosomes (TE) received exosomes (100 μg in 500 μl of sterile saline), and TBI animals with exosomes depleted of MALAT1 (TEdM) received exosomes (100 μg in 500 μl of sterile saline). Sham animals did not receive any injection, and animals receiving unconditioned media were used as control groups. To evaluate the migration of the transplanted exosomes, exosomes were incubated with DiR during isolation as noted above.

XenoLight DiR for In Vivo and Ex Vivo Bio-Distribution Imaging Procedures:

To visualize DiR fluorescence emitted from the injected exosomes in vivo, animal's abdomens were shaved to avoid light scattering and anesthetized in a chamber with 3.0% isoflurane. Animals were then transferred from the chamber to the IVIS Spectrum 200 Imaging System (Xenogen), and the isoflurane level was maintained at 1-2% throughout image acquisition. The biodistribution of DiR-labeled exosomes were monitored in vivo at 1, 4, 12, 24, 48, 72 hours and again at 11 days post-surgery and transplantation. Images were also obtained of ex-vivo organs including brain, liver, lungs and spleen after 1, 3, 7, and 11 days post-surgery and transplantation. Animals full body imaging was performed ventrally at all time points, and a second set of images were obtained for the head region using a higher magnification. The parameters used throughout the experiment were as follows: Exposure time=Auto; Lamp voltage=High; F/stop=2; Binning=8; Excitation filter=745 nm; Emission filter=800 nm; Field of view=D (for whole body), C (for ex vivo organs) or B (for head region). All captured images were analyzed using Living Image Software 4.0 (Xenogen RRID:SCR_014247). To analyze the change in DiR fluorescence intensity, identical regions of interest (ROIs) were placed on the abdomen and head area for animals. The same ROI was also placed on the control animal as the background reference. Background efficiency was subtracted from each of the individual animal's efficiency and presented as an average radiant efficiency (photons per second per square centimeter per steridian divided by microwatts per square centimeter).

Behavioral Testing:

Each rat was subjected to a series of behavioral tests to reveal motor and neurological performance of animals, at baseline before and after TBI at days 0, 3, and 7 days.

Elevated Body Swing Test (EBST): EBST is a measure of asymmetrical motor behavior that does not require animal training or drug injection. The rats were held, in the vertical axis, 1 inch from the base of its tail and then elevated to an inch above the surface on which it has been resting. The frequency and direction of the swing behavior were recorded for 20 tail elevations. A swing was counted when the head of the rat moved 10° from the vertical axis to either side. The total number of swings made to the biased side was added per group and divided by the n, giving us the average number of swings per treatment group.

Forelimb Akinesia: Before and after TBI surgery, rats from all groups were evaluated for forelimb akinesia. Ipsilateral and contralateral forepaw strength and motility were scored by two experimentally blinded evaluators using the following forelimb. Scores were tallied for each individual animal, and then mean scores for treatment groups were used for analyses.

Paw Grasp: Before and after TBI surgery, grip strength of rats from all groups were evaluated. An abnormal grip is indicative of impaired neuromuscular function. In this test, rats were held by their bodies against a pole. Both ipsilateral and contralateral paw grip strength were scored by two experimentally masked evaluators using the following grip strength scale. In a scale of 1 to 3, 1 is normal, 2 is impaired, and 3 is severely impaired. Scores were tallied for each individual animal, and then mean scores for treatment groups were used for analyses.

Brain and Organ Harvesting, Fixation, and Sectioning:

Under deep anesthesia, rats were sacrificed on day 1, 3, 7 and 11 after TBI for protein analysis, RNA sequencing, and/or immunohistochemical investigations. Briefly, animals were perfused through the ascending aorta with 200 ml of cold PBS, followed by 200 ml of 4% paraformaldehyde in phosphate buffer (PB). Brains, spleen, lungs, and liver were removed and post-fixed in the same fixative for 24 h, followed by 30% sucrose in PB until completely sunk. Six series of coronal sections were cut at a thickness of 40 um with a cryostat and stored at −20° C. Six coronal sections between the anterior edge and posterior edge of the impacted area were collected and processed for GFP expression in exosome injected animals.

Measurement of Impact and Peri-Impact Area:

Nissl staining analysis: Serial sections corresponding to the same group of animals were stained with Nissl (Thermo Fisher Scientific Cat # N21483 RRID:AB_2572212) for impact- and peri-impact calculations. Six coronal sections between the anterior edge and posterior edge of the impacted area were collected and processed for Nissl staining from each brain perfused at day 11 after TBI. Sections were cut at a thickness of 40 µm by a cryostat. Every sixth coronal tissue section was randomly selected for measurement of impact- and peri-impact area. Brain sections were examined using a light microscope (Olympus) and Keyence microscope. The impact and peri-impact areas of brain damage was measured in each slice and quantified by a computer-assisted image analysis system (NIH Image RRID: SCR_003070). Impact and peri-impact area was then expressed as a percentage of the ipsilateral hemisphere compared with the contralateral hemisphere.

RNA Sequencing:

RNA Quality Control: RNA was isolated from brains (area near impact site) and spleens of rats at Day 7 following TBI in the sham surgery-control (C), TBI with vehicle (T), TBI treated with exosomes (TE) and TBI treated with MALAT1-depleted exosomes (TEdM) groups. 4 rats of each group were randomly chosen and pooled to maximize biological diversity and sent for RNASeq (Ocean Ridge Biosciences). 8 total RNA samples (4 rat spleen tissue and 4 rat brain tissue), were submitted to Ocean Ridge Biosciences for RNA-Sequencing. RNA was quantified by O.D. measurement, and assessed for quality on a 1% agarose-2% formaldehyde RNA Quality Control (QC) gel. The RNA was then digested with RNase free DNase I (Epicentre; Part # D9905K) and re-purified on RNeasy MinElute columns (Qiagen; Part #74204) using an alternative high ethanol protocol to preserve low molecular weight (LMW) RNAs. The newly purified RNA samples were then quantified by O.D. measurement.

Library Preparation: Ribosomal RNA was depleted from 1 microgram of DNA-free total RNA using the Ribo-Zero Gold rRNA Removal Kit for Human/Mouse/Rat (Illumina, part number MRZG126). Template DNA molecules suitable for cluster generation were then prepared from the rRNA-depleted samples using the ScriptSeq V2 RNA-Seq Library Prep Kit (Illumina, part number SSV21124). The quality and size distribution of the amplified libraries were determined by chip-based capillary electrophoresis on an Agilent 2100 Bioanalyzer. Libraries were quantified using the KAPA Library Quantification Kit (Kapa Biosystems, Boston, Mass.).

Sequencing: The libraries were pooled at equimolar concentrations and diluted prior to loading onto the flow cell of the Illumina cBot cluster station. The libraries were extended and bridge amplified to create sequence clusters using the Illumina HiSeq PE Cluster Kit v4 and sequenced on an Illumina HiSeq Flow Cell v4 with 50-bp paired-end reads plus index read using the Illumina HiSeq SBS Kit v4. Real time image analysis and base calling were performed on the instrument using the HiSeq Sequencing Control Software version 2.2.58. All samples had a minimum of 43,303,826 passed-filter single-end reads. The sequences aligned at an average of 72%+/−2% (SD) efficiency to the reference genome.

Alignment to Genome: Sequence alignment was performed using TopHat v1.4.1 (RRID SCR-013035) with the following settings:

tophat -p 2 -o [OUTPUT FOLDER]--library-type fr-second-strand -r [Dx]-mate-std-dev [Ds] [rn5 BOWTIE GENOME INDEX] [FASTQ 1] [FATSQ 2]

where Dx and Ds represent sample-specific values for the mean and standard deviation, respectively, of the inner distance between reads, as determined by non-gapped alignment to rat mRNA. rn5 BOWTIE GENOME INDEX was built from the soft-masked genome sequence. In practice FASTQ files for each sample were split into multiple FASTQs having 4 million reads each in order to accelerate processing.

ncRNA Counting and Annotation: The number of reads aligning to each ncRNA feature were counted using BEDtools v2.16.2 (RRID SCR-006646) with the following settings: bedtools multicov -bams C80R4ANXX_s8illumina12index_4_SL134409.fastq_05.bam -bed macentral_active_v3_rat-mouse-human.gff C80R4ANXX_s8illumina12index_4_SL134409.fastq_05/counts.txt In practice FASTQ files for each sample were split into multiple FASTQs having 4 million reads each in order to accelerate processing. For each sample, the resulting BAM files were merged and the count files were also merged. For all ncRNAs having at least one read aligned, annotations were added using RNAcentral's RESTful API. The RPKM values were filtered to retain a list of ncRNAs with an RPKM equivalent to 50 mapped reads in one or more samples. The threshold of 50 mapped reads per ncRNA is considered the Reliable Quantification Threshold, since the RPKM values for a ncRNA represented by 50 reads should be reproducible in technical replicates. To avoid reporting large fold changes due to random variation of counts from low abundance ncRNA, RPKM values equivalent to a count of <=10 reads per ncRNA were replaced in the following way. First, for each sample the RPKM value equivalent to 10 reads/ncRNA was calculated (assuming a median ncRNA length of 0.122 kb). These RPKMs were then averaged across all the samples in the experiment, and this average value was used for replacement.

Fold Change Calculations: The filtered RPKM data for 19,058 detectable rat genes (RPKM values>Reliable Quantification Threshold (RQT) in at least one sample) were used for to calculate the fold changes TBI exosome/TBI vehicle, TBI exosome MALAT1/TBI exosome, and TBI vehicle/no TBI for independently for spleen and brain samples, fold changes are expressed as the negative reciprocal in tables and for additional analysis. The splicing index was calculated based on the formula: exon RPKM/gene RPKM.

Hierarchical Clustering: Similarly, the same RPKM data for all 19,058 detectable rat genes were used for hierarchical clustering analysis by Cluster 3.0 software4 (RRID SCR-013505). Genes were log-2 transformed and median centered prior to hierarchical clustering. Hierarchical clustering was conducted on genes and samples using centered correlation as the similarity metric and average linkage as the clustering method. Intensity scale shown is arbitrary.

Real Time qPCR Using SYBR Green:

Total RNA as described above for RNA seq was used for validation. 1 µL of cDNA was amplified by real-time quantitative PCR using Maxima SYBR Green/Rox qPCR master mix (Thermo Scientific) in an ABI ViiA7 sequence detection system (PE Applied Biosystems) to quantify the relative levels of the transcripts in the samples. The primers are: GAPDH sense primer 5'-TGACGTGCCGCCTGGA-GAAAC-3' (SEQ ID NO: 5) and anti-sense 5'-CCGGCATC-GAAGGTGGAAGAG-3' (SEQ ID NO: 6); human MALAT1 sense: 5'-GAGTTCTAATTCTTTTTACTGCT- CAATC-3' (SEQ ID NO: 7) and antisense 5'-TCAAGTGC-CAGCAGACAGCA-3' (SEQ ID NO: 8); mouse MALAT1 sense: 5'-TGCAGTGTGCCAATGTTTCG-3' (SEQ ID NO: 9) and antisense 5'-GGCCAGCTGCAAACATTCAA-3' (SEQ ID NO: 10); U1snRNA sense: 5'-TCCCAGGGCGAG-GCTTATCCATT-3' (SEQ ID NO: 11) and antisense 5'-GAACGCAGTCCCCCACTACCACAAAT-3' (SEQ ID NO: 12). Real-time PCR was then performed in triplicate on samples. The plate setup included a no template control, no RNA control, no reverse transcriptase control, and no amplification control. After primer concentrations were optimized to give the desired standard curve and a single melt curve, relative quotient (RQ) was determined using the ΔΔCT method with U6snRNA or GAPDH as the endogenous control and No TBI sample as the calibrator sample. Experiments were repeated four times.

Example 2: Exosomes Secreted by hASC Increase Expression of PKCδII in HT22 Cells The immortalized mouse hippocampal cell line HT22 is widely used to study neuronal survival and is established as an in vitro model for mechanistic studies for neuronal diseases. PKCδ is alternatively spliced to PKCδI and PKCδII in mouse HT22 cells. PKCδI is pro-apoptotic while PKCδII promotes survival. PKCδII increases neuronal survival via Bcl2 in HT22 cells. The effect of hASC secretome (collected as conditioned media—CM) on PKCδ alternative splicing was examined in HT22 cells. hASC cells were grown to confluency and CM collected after 48h. Exosomes were isolated from CM (methods). HT22 cells were treated with 10 g hASC exosomes for 24h. Whole cell lysates were collected and western blot analysis performed with antibodies as indicated in FIG. 1A. The gels represent three experiments performed separately with similar results. FIG. 1B shows percent densitometric units normalized to GAPDH for each antibody and represents three separate experiments. The results were analyzed with two-tailed Student's t-test using PRISM4 statistical analysis software (GraphPad, San Diego, Calif.). A level of $p<0.05$ was considered statistically significant. *** is $p<0.0001$ highly significant between control and hASC exosome treated cells for PKCδII and Bcl2. FIG. 1C shows SYBR Green Real Time qPCR using PKCδI and PKCδII primers. GAPDH served as control. For absolute quantification, a standard curve was generated for each gene in every assay. Absolute quantification of mRNA expression levels for PKCδI and PKCδII was calculated by normalizing the values to GAPDH.

Experiments repeated four times with similar results. The results were analyzed with two-tailed Student's T-test using PRISM4 statistical analysis software (GraphPad, San Diego, Calif.). A level of $p<0.05$ was considered statistically significant. *** is $p<0.0001$ highly significant between control and hASC exosome treated cells for PKCδII.

Example 3: Exosomes from hASC are Taken Up by HT22 Cells

To verify that exosomes from hASC are taken up by HT22 cells, hASC were transiently transfected with pmax-GFP using nucleofection. The cells were allowed to recover for 48 hours and fresh dye-free media was added to the hASC. After 48h, the conditioned media was collected and exosomes were isolated (GFP-hASC Ex). 10 μg GFP-hASC Ex were added to HT22 cells for 24h. Cells were harvested and pPCR was performed to assess GFP levels in recipient HT22 cells (FIG. 2A). Results are quantified in FIG. 2B, which shows increased GFP expression in HT22 cells treated with GFP-hASC Ex and no GFP expression in untreated control cells. FIG. 2C shows western blot analysis for the presence of human exosome cell-surface markers CD9, CD63 and CD81 in HT22 cells treated with GFP-hASC Ex. Blots represent three experiments performed separately with similar results. Taken together, these results demonstrate successful uptake of exosomes in HT22 cells treated with GFP-hASC Ex.

Example 4: Exosomes from hASC Enhance Neuronal Survival and Proliferation

The ability of hASC exosomes to increase survival and proliferation in HT22 cells was assessed. BrdU-coupled enzyme-linked immunosorbent assay was performed in HT22 cells treated with 10 μg hASC exosomes for 24h. The incorporation of 5-bromo-2'-deoxyuridine (BrdU) into replicating DNA was used to label proliferating cells. BrdU is incorporated into S-phase cells and serves as a proliferation marker and can be quantitatively assayed to determine cell proliferation. BrdU is detected immunochemically allowing for the assessment of neuronal cells synthesizing DNA. As shown in FIG. 3A, treatment with hASC increased the amount of BrdU concentration in HT22 cells.

Next, to verify that hASC exosomes increases cell survival and proliferation, a cell proliferation assay based on WST1 (a tetrazolium salt) cleavage to formazan by mitochondrial dehydrogenases was performed. Increased proliferation of cells results in increased activity of the mitochondrial dehydrogenases in the sample which can be measured quantitatively by increases in formazan dye production. As shown in FIG. 3B, hASC exosomes increased HT22 cell survival and proliferation. The measurements were made in triplicate in three separate experiments. The results were analyzed with two-tailed Student's t-test using PRISM4 statistical analysis software (GraphPad, San Diego, Calif.). A level of $p<0.05$ was considered statistically significant. *** is $p<0.0001$.

Example 5: hASC Exosomes Contain Long Noncoding RNA MALAT1

Long noncoding RNAs (lncRNAs) are emerging as important modulators of gene expression. Exosomes secreted from subcutaneous hASC are significantly enriched in the lncRNAs MALAT1, GAS5 and lincRNA-VLDLR. MALAT1 predominantly regulates alternative splicing of genes by modulating the activity of splice factors. MALAT1 has been extensively studied in several cancers where it is shown to regulate gene expression either by promoting alternative splicing or by regulating assembly of complexes mediating gene expression.

To delineate the amount of MALAT1 taken up from exosomes as compared to endogenous MALAT1 in HT22 cells, HT22 cells were treated with 10 μg of exosomes from hASC (hASC Ex). RNA was isolated and primers specific for either mouse or human MALAT1 were used in SYBR Green qPCR. As shown in FIG. 4A, human MALAT1 levels are increased in HT22 cells treated with hASC exosomes. Experiments were repeated five times with similar results. The results were analyzed with two-tailed Student's t-test using PRISM4 statistical analysis software (GraphPad, San Diego, Calif.). A level of $p<0.05$ was considered statistically significant. *** is $p<0.0001$ highly significant between hASC exosomes and control for MALAT1.

hASC secretome contains a milieu of protein and RNA factors. The RNA component is encapsulated in vesicles such as exosomes to prevent its degradation. To determine if an RNA component of the exosome increases PKCδII expression, 10 μg hASC exosomes were incubated with a cocktail of ribonucleases (1 μL RiboShredder RNase Blend Epicenter, cat # RS12100) at 37° C. for 1h. Total RNA was isolated from hASC-Ex ribonuclease and absolute SYBR Green real time qPCR was performed using human MALAT1 primers. As shown in FIG. 4B, hASC exosomes treated with the ribonuclease cocktail were depleted of MALAT1. HT22 cells were then either treated with 10 μg of hASC exosomes or 10 μg of ribonuclease cocktail treated exosomes (which are depleted in MALAT1). Total RNA was isolated from HT22 cells and SYBR Green real time qPCR was performed for PKCδI and PKCδII. As shown in FIG. 4C, qPCR results indicated that ribonuclease cocktail treated hASC exosomes did not increase PKCδII expression in HT22 cells. Experiments repeated three times with similar results. The results were analyzed with two-tailed Student's t-test using PRISM4 statistical analysis software (GraphPad, San Diego, Calif.). A level of $p<0.05$ was considered statistically significant. *** is $p<0.0001$ highly significant between HT22 control and hASC exosomes treated cells for MALAT1.

Example 6: Depletion of MALAT1 Impacts hASC Mediated PKCδII Splicing

Given that hASC exosomes had significantly higher levels of MALAT1 and that PKCδII levels were increased in HT22 following treatment with hASC exosomes, whether depletion of MALAT1 in hASC exosomes affected PKCδII levels in HT22 cells was investigated. Two antisense oligonucleotides (ASOs) to human MALAT1 were evaluated (IDs: 395254 and 395240) along with the scrambled antisense oligonucleotides (control) (ASOs from Ionis Pharmaceuticals (formerly known as ISIS Pharm), validated for specificity and designed for efficient uptake by cells). hASC were treated with 50 nM ASOs 395254 and 395240 or scrambled ASO control (ASOscr) for 48 h. Exosomes were isolated from the conditioned media (abbreviated as M1ASO-254 Ex or M1ASO-240 Ex or ScrASO Ex). ScrASO Ex, M1ASO-254 Ex or M1ASO-240 Ex (10 μg each) were added to HT22 cells for 24h. Total RNA was isolated from HT22 cells and real time absolute qPCR was performed to determine levels of MALAT1 and PKCδ splicing variants.

Results indicated 80% decline in human MALAT1 RNA (h MALAT1) in the M1ASO-254 Ex or M1ASO-240 Ex samples. MALAT1 levels remained constant in ScrASO Ex (FIG. 5A) As shown in FIG. 5B, M1ASO-254 exosomes or M1ASO-240 exosomes did not increase PKCδII splicing in HT22 cells. The scrambled ASO exosomes increased PKCδII splicing mimicking control hASC exosomes treated HT22 cells. PKCδI splicing was not affected significantly with hASC exosomes or M1ASO-254 exosomes or M1ASO-240 exosomes. As a control, levels of endogenous MALAT1 levels in HT22 cells using mouse MALAT1 primers were measured in qPCR. As shown in FIG. 5C, addition of hASC-exosomes did not significantly alter mouse MALAT1 levels (m MALAT1) in HT22 cells.

Experiments were repeated five times with similar results. The results for all experiments were analyzed with two-tailed Student's t-test using PRISM4 statistical analysis software (GraphPad, San Diego, Calif.). A level of $p<0.05$ was considered statistically significant. * is $p<0.0001$ highly significant between HT22 control and $Scr_{ASO}$ Ex treated cells for PKCδII. * is $p<0.0001$ highly significant between $Scr_{ASO}$ Ex and $M1_{ASO}$-254 Ex or $M1_{ASO}$-240 Ex treated cells for PKCδII.

Example 7: MALAT1 Promotes PKCδII Alternatively Splicing Via SRSF2

MALAT1 interacts with several pre-mRNA splice factors and modulates alternative splicing. In HT22 cells, PKCδII alternative splicing is regulated by the serine-arginine rich splice factor 2 (SRSF2) also known as SC35. Whether MALAT1 in hASC exosomes could promote PKCδII splicing in the absence of SRSF2 was evaluated. SRSF2 siRNA (50 nM for 48h; SRSF2 siRNA from Ambion 12444) was transfected into HT22 cells for 48h to deplete SRSF2. Fresh medium was replaced and HT22 cells were treated with 10 μg hASC exosomes for 24h. RNA was isolated for qPCR analysis. Absolute SYBR Green qPCR was performed with GAPDH as internal control.

As shown in FIG. 6A, HT22 cells treated with MALAT1 containing hASC exosomes increased PKCδII while the SRSF2 depleted HT22 cells did not show an increase in PKCδII with hASC exosome treatment. A standard curve was generated for each gene. Absolute quantification of mRNA expression levels for PKCδI and PKCδII was calculated by normalizing the values to GAPDH. The experiments were repeated four times with similar results. *** is $p<0.0001$ highly significant.

SRSF2 regulates PKCδII alternative splicing. As such, whether MALAT1 influenced the binding of SRSF2 to PKCδ pre-mRNA was evaluated. HT22 cells were treated with 10 μg hASC exosomes containing MALAT1. RNA coimmunoprecipitation (RIP) assay was performed using primers to PKCδ pre-mRNA. Immunoprecipitated RNA was analyzed by qPCR for PKCδ using primers flanking the SRSF2 binding site on PKCδ pre-mRNA. As shown in FIG. 6B, SRSF2 binds to PKCδ pre-mRNA. HT22 cells treated with hASC exosomes showed an enrichment of SRSF2 on PKCδ pre-mRNA. Graph is plotted as fold enrichment of SRSF2 using qPCR in the RIP assay with SRSF2 IP; fold enrichment of U1 RNA using SNRP70 IP (positive control). Results show SRSF2 binding to PKCδ pre-mRNA. Inset show immunoblot of SRSF2 IP and IgG IP (negative control) using antibody against SRSF2. Experiments were repeated four times with similar results.

Separately, HT22 cells were transfected with 2 μg of PKCδ heterologous splicing minigene and treated with or without hASC exosomes (10 μg) for 24h. PKCδ splicing minigene was developed by cloning mouse exon 9 of PKCδ along with its flanking 3' and 5' introns were into the pSPL3 splicing vector. Utilization of 5' splice site I results in PKCδI while utilization of 5' splice site II results in PKCδII. Total RNA was isolated, reverse transcribed and 2 μl cDNA was used in PCR. The primers used were on SD and SA exon of pSPL3 splicing vector as indicated in the schematic of the PKCδ splicing minigene. 5% of the products were separated by PAGE and silver stained for visualization. As shown in FIG. 6C, treatment with hASC exosomes increased utilization of 5' splice site II in the pSPL3-PKCδ minigene. Graphs represent percent exon inclusion calculated as SS II/(SS II+SSI)×100 in the samples and are representative of four experiments performed separately.

Cells utilize lncRNAs to maximize the ability of splice factors to regulate splicing. The results described above suggest that MALAT1 recruits SRSF2 and stabilizes its association with PKCδ premRNA to promote PKCδII splicing. SRSF2 regulates PKCδII alternative splicing. To evaluate whether MALAT1 bound to SRSF2 in HT22 cells, RNA co-immunoprecipitation (RIP) assay was performed. MALAT1 is shown to co-localize in the nuclear speckles with SRSF2. Hence, whether MALAT1 and SRSF2 associated in the nucleus of HT22 cells was evaluated. HT22 cells were treated with hASC exosomes (10 g) containing MALAT1 for 24h. The nuclear and cytoplasmic RNA from HT22 cells were separated and isolated (RNA subcellular isolation kit-ActiveMotif). RNA coimmunoprecipitation (RIP) assay was performed using SRSF2 antibody and primers in RTqPCR specific for human MALAT1. As shown in FIG. 6C, human MALAT1 from the hASC exosomes bound to SRSF2 in HT22 cells with a 2-fold higher affinity when compared to binding of the positive control snRNP70 and U1 RNA in the nuclear fraction while no association was observed in the cytoplasmic fraction. is plotted as fold enrichment of MALAT1 using qPCR in the RIP assay with SRSF2 IP; fold enrichment of U1 RNA using SNRP70 IP (positive control). Inset show immunoblot of SRSF2 IP and IgG IP (negative control) using antibody against SRSF2. Experiments were repeated four times with similar results.

Example 8: Insulin Enhances hASC Secretome's Ability to Increase Neuronal Proliferation and Survival The effect of combining insulin treatment with hASC exosomes treatment in enhancing neuronal proliferation and survival was evaluated. To determine if hASC exosomes and insulin may be neuroprotective, oxidative stress with hydrogen peroxide was induced. Oxidative stress induced cell damage is common in etiology of several neurobiological disorders including traumatic brain injury (TBI). HT22 cells were administered 100 μM H2O2 for 24h. The cells were then treated with either 10 μg hASC exosomes, 10 μg MALAT1 depleted exosomes (M1ASO-254 exosomes) or insulin (10 nM) alone or in combination with exosomes treatment. Immunochemistry was performed with either Ki67 (for proliferating cells) or DAPI (for nuclei). As shown in FIG. 7, H2O2 treatment significantly decreased the number of proliferating HT22 cells. FIG. 7A shows merged images demonstrating the amount of proliferating cells compared to total HT22 cells. Treatment of H2O2 treated HT22 cells with hASC exosomes significantly increased HT22 proliferation while MALAT1 depleted exosomes (M1ASO-254 exosomes) had lower ability to increase HT22 proliferation post-H2O2 treatment. Additionally, the results demonstrate that addition of insulin post-H2O2 treatment along with hASC exosomes in HT22 cells significantly increased proliferation in HT22 cells. White bar in images is 50 μm. Inset below shows HT22 cells stained with doublecortin confirming neuronal cells. Experiments were performed five times with similar results. Images were captured on Nikon microscope.

Next, an in vitro scratch assay was used to study injury to the neurons and its wound healing in response to treatment with exosomes. HT22 cells were plated in a 35 mm plate and cells were scratched using a pipette tip to mimic injury. The boundary of scratch on each side was marked on the outside bottom of the plate. 10 μg hASC exosomes, 10 μg MALAT1 depleted exosomes (M1ASO-254 exosomes) insulin (10 nM), or a combination thereof were added to the HT22 cells for 24 hours. Using a Nikon microscope, cell images were captured for five different fields of 1 μm2 area and wound width was measured 24h later post treatments. As shown in FIG. 7B and FIG. 7C, hASC exosomes and insulin treatment either separately or in combination enhances wound healing as measured by decrease in wound width compared to the control wound width. MALAT1 depleted exosomes increased wound healing but to a smaller extent compared to hASC exosomes.

Figure 7D:
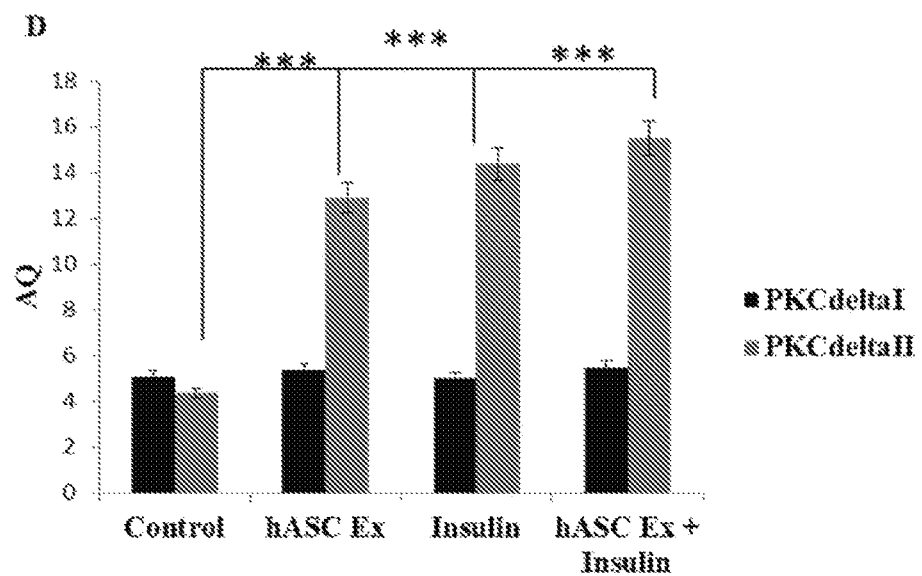

The above proliferation and migration assay were designed to verify that the increase in neuronal proliferation and survival due to hASC exosomes and insulin treatment was due to increased splicing of PKCδII. In the above experiments, separately total RNA was isolated and SYBR Green Real Time qPCR was performed using PKCδI and PKCδII primers for absolute quantification. GAPDH served as control. As shown in FIG. 7D, SYBR Green qPCR results show PKCδII alternative splicing was increased by hASC exosomes and hASC exosomes with insulin treatment, whereas PKCδI levels were not significantly affected. These results demonstrate that insulin enhances hASC and its secretome's ability to increase neuronal survival via PKCδII. For absolute quantification, a standard curve was generated for each gene in every assay. Absolute quantification of mRNA expression levels for PKCδI and PKCδII was calculated by normalizing the values to GAPDH. Experiments repeated four times with similar results. The results were analyzed with two-tailed Student's t-test using PRISM4 statistical analysis software (GraphPad, San Diego, Calif.). A level of p<0.05 was considered statistically significant. *** is p<0.0001 highly significant between hASC exosomes treated with or without insulin.

Example 9: Insulin Increases Association of MALAT1 with SRSF2

Figure 8:
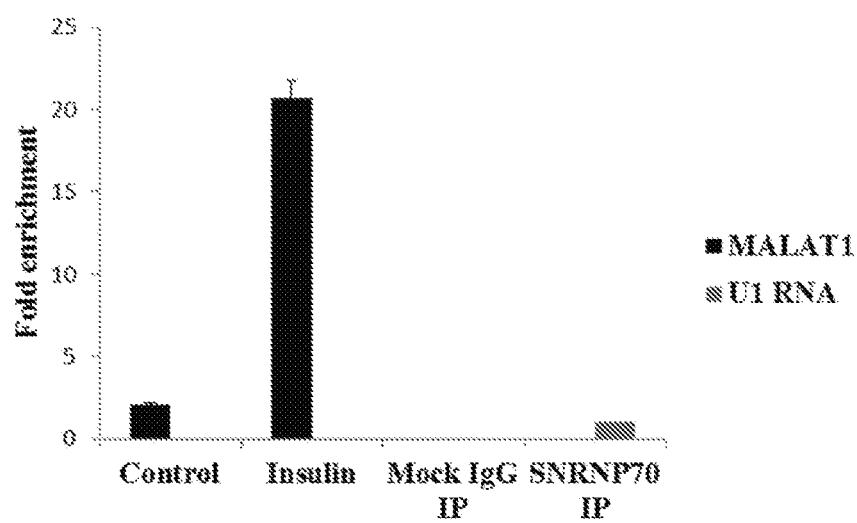
FIG. 8 shows insulin increases association of MALAT1 with SRSF2.

The results above demonstrate that MALAT1 sequesters SRSF2 in HT22 cells. As such, the effect of insulin treatment on association of MALAT1 and SRSF2 in HT22 cells was investigated. HT22 cells were treated with or without 10 nM insulin for 24h. RIP assay was performed on HT22 cells treated with or without 10 nM insulin. Immunoprecipitated RNA was analyzed with primers for MALAT1 flanking SRSF2 putative binding site. As shown in FIG. 8, insulin dramatically increased the association of MALAT1 and SRSF2 in HT22 cells in the RIP assay compared to HT22 cells without insulin treatment. These results suggest that MALAT1 sequesters SRSF2 to enhance the ability of kinases (such as AKT2) to phosphorylate SRSF2 which is essential for the function of SRSF2 to promote alternative splicing of PKCδII. Graph is plotted as fold enrichment of MALAT1 using qPCR in the RIP assay with SRSF2 IP; fold enrichment of U1 RNA using SNRP70 IP (positive control). Experiments were repeated four times with similar results.

Example 10: Exosome Treatment Improves Motor Impairment and Reduces Lesion Volume in a MALAT1 Dependent Manner Fisher 344 male rats were subjected to either TBI by controlled cortical impact (CCI) injury model or no TBI (sham surgery only, control group) and treated with hASC exosomes after 3 hours of surgery. The rats were randomly distributed into the following groups: Surgery with no TBI (Sham control C, N=11), TBI with unconditioned media as vehicle (T; N=20), TBI treated with exosomes (TE, N=18), TBI treated with exosomes depleted of MALAT1 (TEdM, N=20). To delineate the effect of exosomes from other vesicles of the secretome, a group of rats where the conditioned media (CM) was depleted of exosomes was included: TBI with injection of conditioned media depleted of exosomes (TdCM; N=7). Each rat was subjected to a series of behavioral tests to reveal motor and neurological performance of animals, before and after TBI and after exosome transplantation. The tests included the elevated body swing test (EBST), forelimb akinesia, and paw-grasp test before injury and after TBI at days 0, 1, 3, and 7.

The EBST records the number of lateral swings to one side or the other and defines a swing bias to one side as a motor defect. A score of 10 equals no bias and higher scores indicate asymmetry. EBST revealed that rats subjected to TBI exhibited heightened swing bias and therefore significant asymmetry in motor activity after injury. TBI (T) animals displayed no recovery when tested on Days 3 and 7, whereas significant recovery of motor symmetry was detected in TBI-exosome treated rats (TE) (Two way ANOVA followed by Tukey's post-hoc, $p<0.01$ versus TBI-Veh; FIG. 9A) Treatment with either conditioned media depleted of exosomes (TdCM) or exosomes depleted of MALAT1 (TEdM) did not affect recovery of the animals, and scores from these groups were not significantly different from the TBI-vehicle (T) group.

The forelimb akinesia test indicated an apparent loss of motor strength in TBI rats after injury when compared with sham controls. TBI-Veh (T) animals retained impairment through day 7 and did not display any significant amelioration of forelimb akinesia. The TBI animals treated with exosomes (TE) animals recovered by day 3 (FIG. 9B), whereas TBI animals treated with conditioned media depleted of exosomes (TdCM) had only modest recovery after day 3, but not day 7.

Assessment of paw grasp function is indicative of TBI-associated loss of strength and was apparent in all animals subjected to injury. After day 3 post TBI, TBI exosomes treated (TE) animals scored significantly better on the paw grasp test compared to TBI-vehicle treated (T) animals. The animals in the conditioned media depleted of exosomes and the exosomes depleted of MALAT1 groups again showed a modest improvement at Day 3 that was not maintained at day 7 (FIG. 9C). Results show only cohort treated with exosomes maintained this significant treatment effect on the paw grasp assessment demonstrating continued recovery of strength for the exosome treated group compared to TBI sham treatment cohort (Two way ANOVA followed by Tukey's post-hoc, $p<0.001$), and this was not observed for rats treated with either conditioned media depleted of exosomes (TdCM) or exosomes depleted of MALAT1 (TEdM).

Figure 9G:
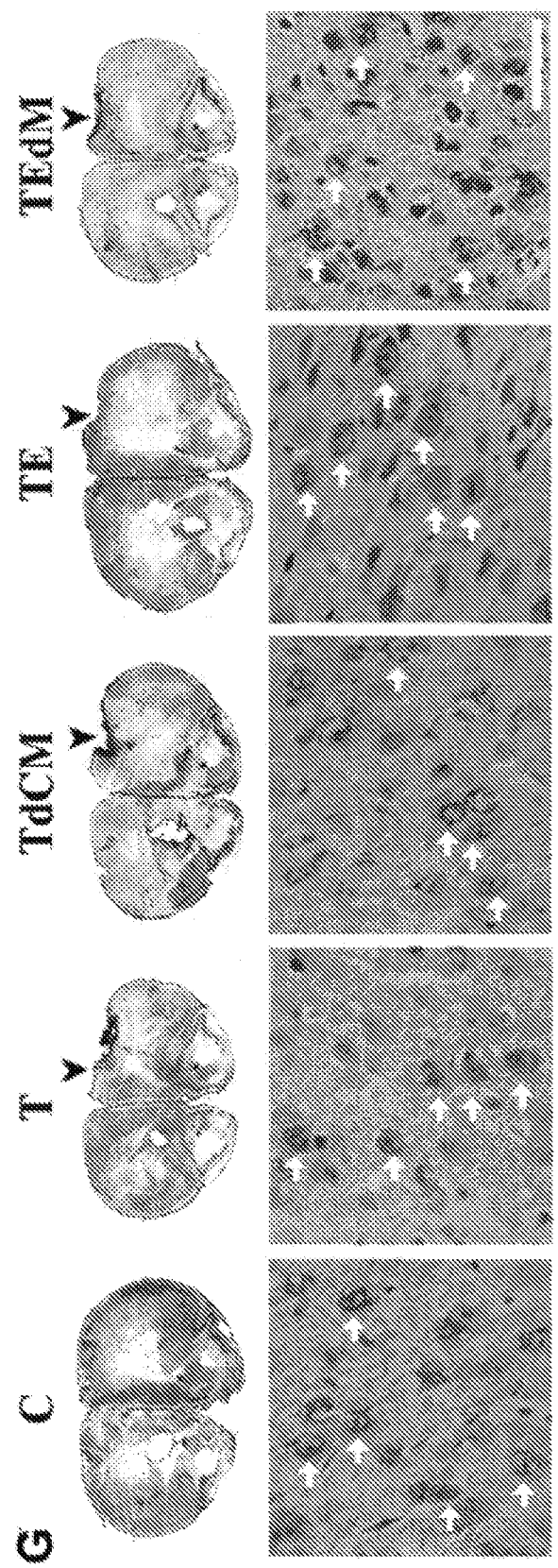

Nissl staining was performed to quantify the lesion volumes and surrounding damage after TBI in the per-impact area. Administration of exosomes was found to significantly reduce both the impact (FIG. 9D) and peri-impact (FIG. 9E) area of TBI-associated injury in the ipsilateral hemisphere. Exosomes depleted of MALAT1 (TEdM) had moderate improvement in peri-impact measures, but not impact area (FIG. 9D,E) Treatment with conditioned media depleted of exosomes did not show recovery in either the impact or peri-impact area after TBI injury. Examples of images used for analysis are shown in FIG. 9G, also shown are examples of images used to quantify the neurons in the peri-impact area.

Figure 10A:
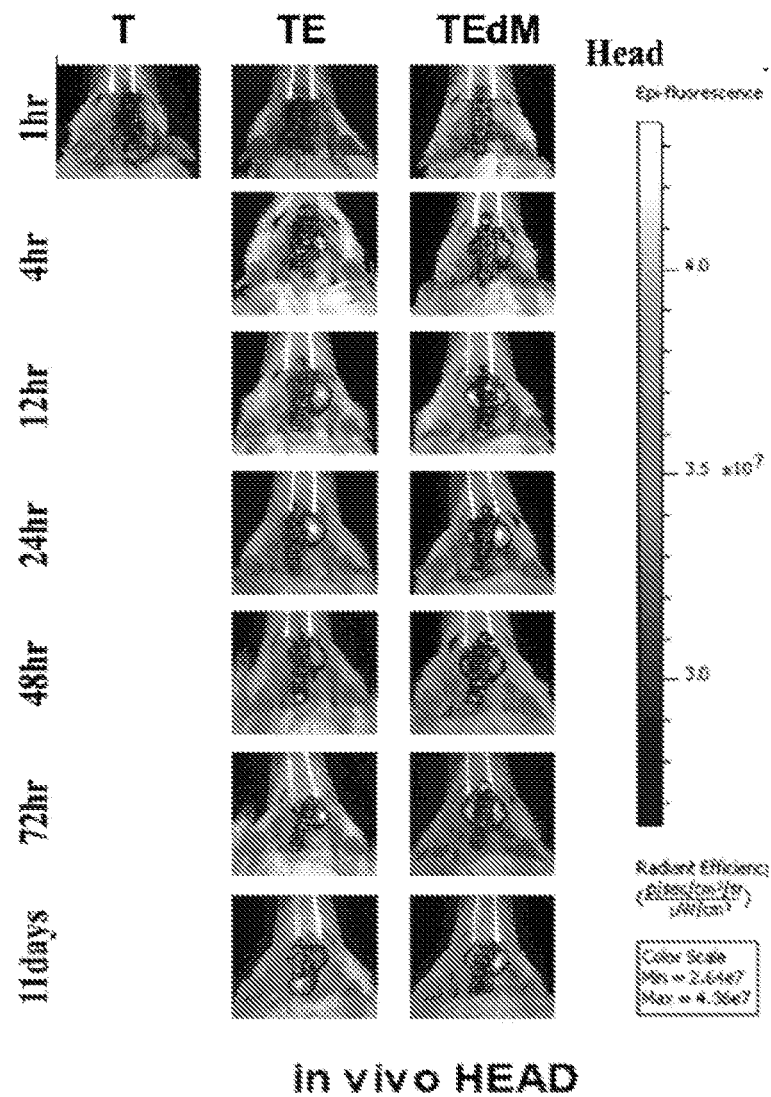
FIGS. 10A-B show in vivo biodistribution of DiR labeled exosomes after TBI. Imaging revealed exosomes migrated robustly to the spleen and liver at 1 and 4 hours after transplantation before gradually decreasing. Exosomes also migrated to the impact site of the brain 4 hours after transplantation and steadily increased through 72 hours relative to sham controls. Graphs in FIG. 10C show radiant efficiency is expressed as photons per second per square centimeter per steridian divided by microwatts per square centimeter$(((p/s)/[cm]^2/sr)/(\mu W/[cm]^2))$. Data in bar graphs represent the mean±SEM values N=3 per group.
Figure 10B:
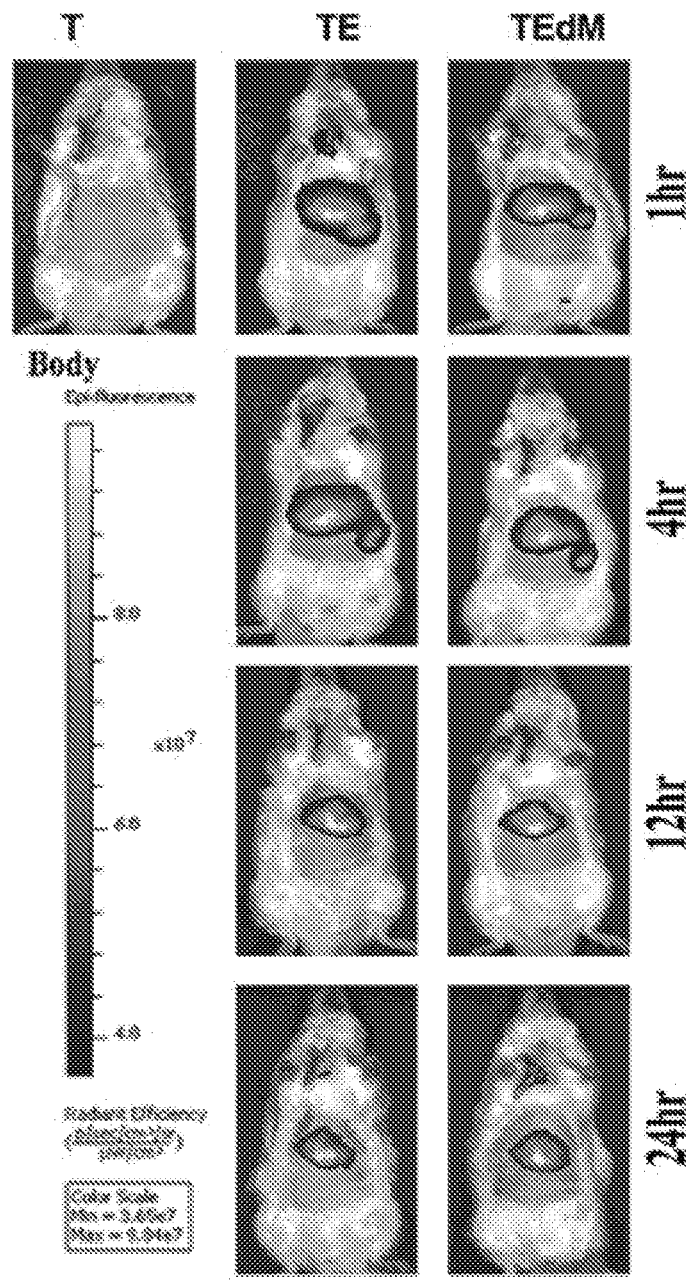
Figure 10C:
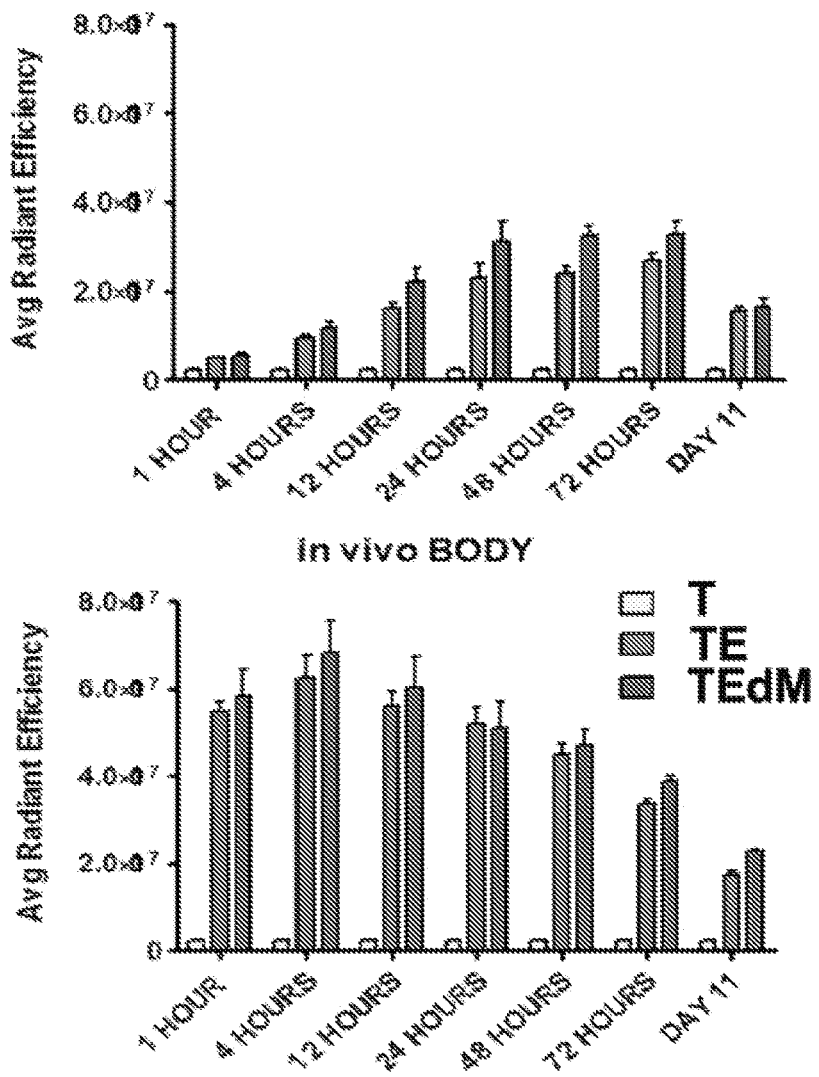

Example 11: Imaging of Exosomes In Vivo Show Distribution Primarily to Abdomen and Head Regions The biodistribution of exosomes was determined in vivo in rats with CCI treated with exosomes. Exosomes were labeled with XenoLight DiR and administered through the jugular vein of TBI-animals 3 hours after injury and their biodistribution was tracked at time points 1, 4, 12, 24, 48, 72 hours and 11 days after surgery (FIGS. 10A-C). Minimal DiR signal was detected in both the head FIG. 10A) and body regions (FIG. 10B) of the sham control animals as expected which provided a reference value throughout the analysis. Within the first hour of transplantation, no noticeable signal was observed in the head region of either treatment groups, whereas a high level of fluorescent signal was present in the abdomen of both TBI groups treated with either exosomes (TE) or exosomes deleted of MALAT1 (TEdM) animals. Fluorescent signal slightly increased after 4 hours for both groups and in both the head and abdomen regions of the animals. At the 12-hour time point, the signal in the head region had increased from the previous time points and continued to increase at 24 hours where it seemed to plateau through 48 and 72 hours until decreasing on day 11 after transplantation. The abdomen region instead displayed the opposite trend and showed a gradually decreasing DiR signal after 4 hours that continued to decline at the 12, 24, 48, and 72 hour time points as well as a lower radiant efficiency on day 11 compared to previous radiant efficiencies at the earlier time points. Quantitative analysis confirmed these observations, as shown in FIG. 10C. Throughout all the data points, the group treated with exosomes depleted of MALAT1 showed a slightly higher average radiant efficiency while following the same trend as exosome treated animals, but this did not achieve significance.

Figure 11A:
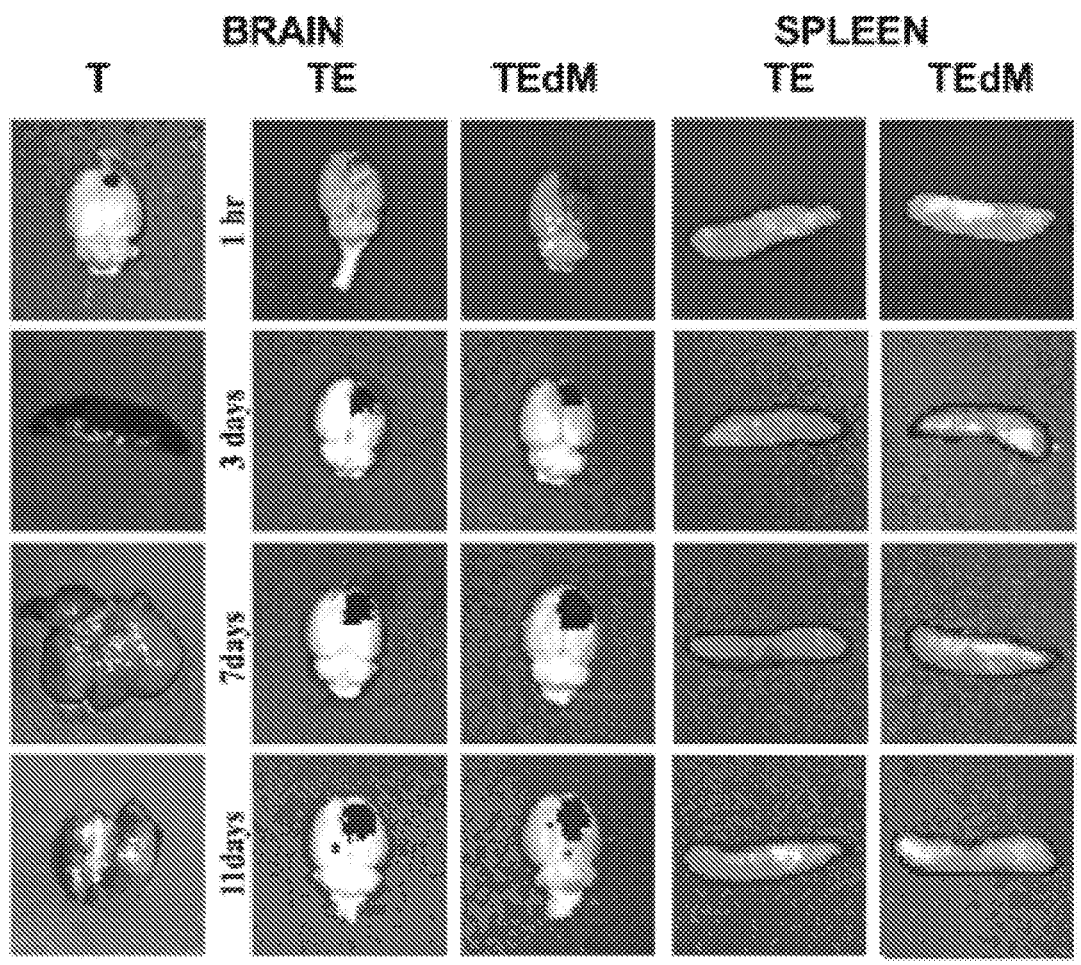
FIGS. 11A-B show ex vivo biodistribution of DiR labeled exosomes after TBI.
Figure 11B:
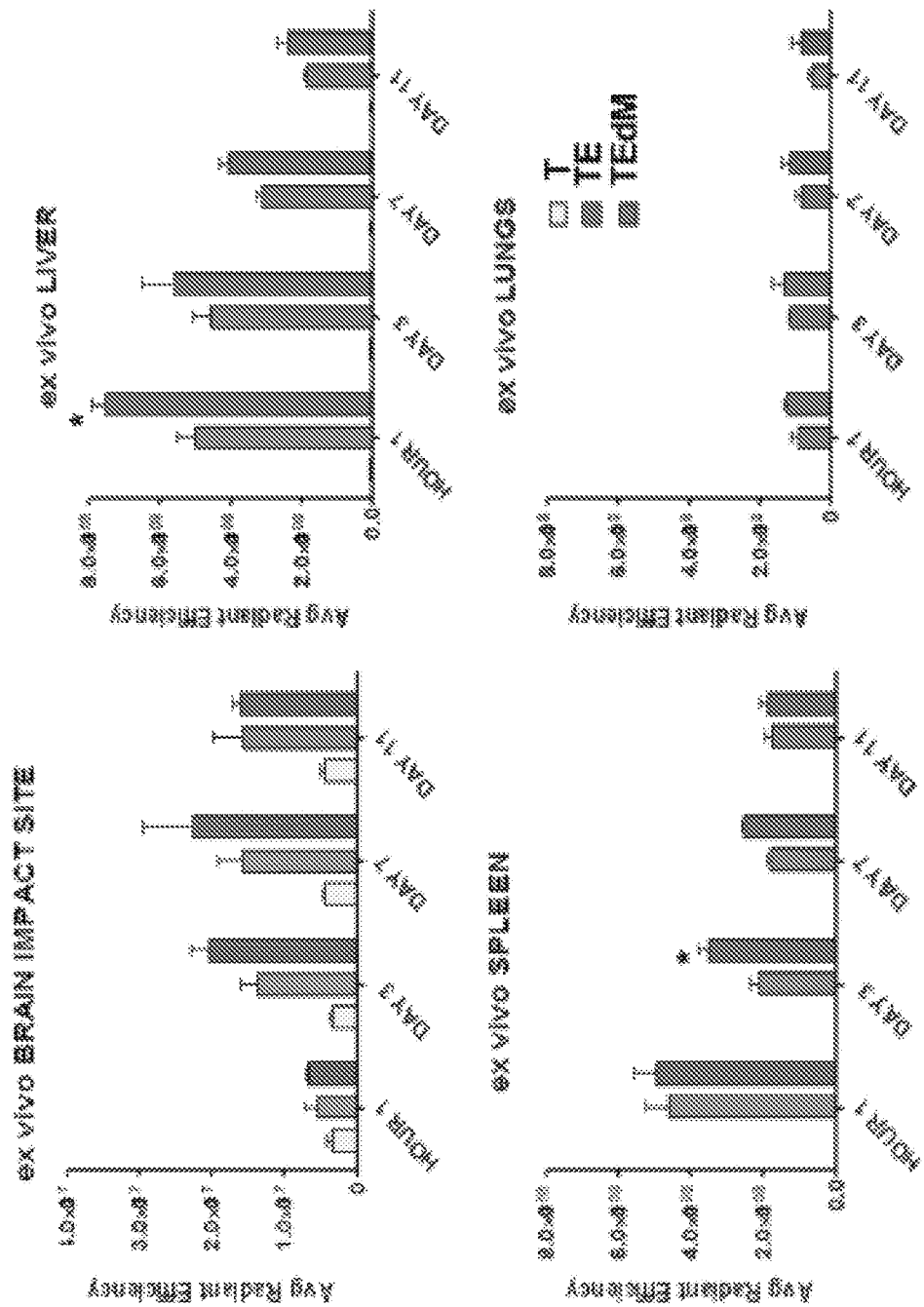

Example 12: Imaging of Exosomes Ex Vivo in Organs Show Localization Primarily to Spleen and Brain Next, the biodistribution of exosomes was determined ex vivo in organs of rats with CCI treated with exosomes. Exosomes were labeled with XenoLight DiR and administered as described above for in vivo imaging. A separate cohort was examined and organs imaged ex vivo at 1 hr, and 3, 7, and 11 days following TBI (FIGS. 11A-B) One hour after administration, the highest signal was observed in the spleen whereas the liver and the lungs showed lower signal intensity and there was no signal observed in the brain. Interestingly, there was higher signal for the exosomes depleted of MALAT1 (TEdM) in the liver at 1 hour suggesting a higher clearance. At day 3, a reduction in signal was observed in the spleen and liver and this continued over time. The brain however, increased in signal on day 3 and continued to increase through day 7.

Example 13: RNA Sequencing Transcriptome Analysis Identifies Cellular Processes Crucial to Recovery that are Specifically Mediated by MALAT1

To gain insight into genomic changes following CCI and its treatment with hASC exosomes, RNA Sequencing was performed. Transcriptome analysis provides valuable knowledge of genomic changes following brain injury and the response to treatment with exosomes. RNA was isolated from brains (area near impact site) and spleens of rats at Day 7 following TBI in the sham surgery-control (C), TBI with vehicle (T), TBI treated with exosomes (TE) and TBI treated with MALAT1-depleted exosomes (TEdM) groups. 4 rats of each group were randomly chosen and pooled to maximize biological diversity and sent for RNA Seq (Ocean Ridge Biosciences). The percent of mapped reads to total genome over total read across all sequencing was 96±0.7%.

Hierarchical clustering of the entire RNA-Seq transcriptome data was performed in order to evaluate the relationship between gene expression profiles in brain or spleen with respect to the different treatments i.e. No TBI sham surgery control (C), TBI treated with vehicle (T), TBI treated with exosomes (TE) and TBI treated with exosomes depleted of MALAT1 (TEdM). The same RPKM data for all 19,058 detectable genes were used for hierarchical clustering analysis by Cluster 3.0 software. Genes were log-2 transformed and median centered prior to hierarchical clustering. Hierarchical clustering (FIG. 12A) was conducted on genes and samples using centered correlation as the similarity metric and average linkage as the clustering method. FIG. 12B shows the hierarchical clustering conducted for ncRNAs as described above for gene expression. Each color-bar unit in both hierarchical clustering represents a difference of one log 2 unit in RPKM value. Zero (0) is the median RPKM value across all samples. Heat maps with row dendograms are shown to visualize the result of the hierarchical clustering calculation. This depicts the distance or similarity between rows and which nodes each row belongs to, as a result of clustering. In either brain or spleen, the results of the clustering heat map show groups of genes or ncRNAs whose expression is affected by TBI and the exosome treatments. Principal component analysis showed similar distinction between groups (data not shown).

Example 14: RNA Seq of Brain and Spleen Transcriptome Identifies Genes Affected by TBI and Treatment with Exosomes The highly enriched genes for spleen and brain were further analyzed. The results (above FIG. 12A-B) indicated specific sets of genes that were affected by TBI that were distinct between the spleen and brain sets as expected based on cell type and cell-specific markers. Based on fold changes, the top genes affected by TBI and treatment with exosomes in the spleen, were enzymes such as pancreatic α-amylase, pancreatic α-amylase precursor, phospholipase A2, caroxypeptidase B precursor, bile salt-activated lipase precursor, chymotrypsinogen B precursor, carboxypeptidase A2 precursor and anionic trypsin 1 which were elevated after TBI and reduced with exosome treatment. Further in the spleen, genes that were upregulated following TBI were related to GO categories of enzyme inhibitor activity, defense response, platelet alpha granule lumen and protein-DNA complexes. In the brain, RNASeq data revealed previously undescribed transcripts ENSRNOG00000047520, ENSRNOG00000049727, ENSRNOG00000050024, ENSRNOG00000046742 whose levels changed with TBI and exosomes treatment. Additionally, genes in the brain that were upregulated following TBI were related to immune responses, cellular response to stress, aging and DNA damage. The splicing index of genes in spleen that were predominantly changed with TBI and exosomes treatment were Tbcd, Chmp1a, Cnst, Lphn1, Zfp560, Mrpl23, Emc4, Zfp329. The splicing index of genes in brain that were predominantly changed with TBI and exosomes treatment were Rps6ka3, Nrtk3, Nap1l1, Eif4g1, Fsd1, Trim44, Dst, Rps15, Fkbp2, Rabgap1l.

Example 15: Gene Expression Patterns Following Treatment with hASC Exosomes

Gene changes that fit the pattern observed with both the behavior and lesion area are of high interest. This expression pattern changes with TBI and responds in the opposite direction with exosomes treatment and reverts to the direction of TBI alone with exosomes depleted of MALAT1. The genes that fit this pattern of gene expression responses were labeled (+1; up with TBI (T), down with TBI+exosomes (TE) and up with TBI+MALAT-depleted exosomes (TEdM)) or the opposite pattern (−1; down with TBI (T), up with TBI+exosomes (TE) and down with TBI+MALAT-depleted exosomes (TEdM)) the data was further filtered for a minimum of 2 fold gene expression change compared with TBI and analyzed using Ingenuity Pathway Analysis (IPA) for both the brain and the spleen separately. The IPA bioinformatics package identifies regulatory nodes (upstream regulators) based upon the fold change values of dataset to predict a relationship of these nodes to drive the detected changes in gene expression. In this manner the top upstream regulators that fit this Pattern +1 and −1 are listed for brain and spleen in FIG. 20 Only values with a significant −log (p Value) were included in the tables and if the Z score indicates a predicted significant up or down regulation within each pattern that is also noted in the table. Canonical pathways identified as significant are listed in Table 1.

Figure 13:
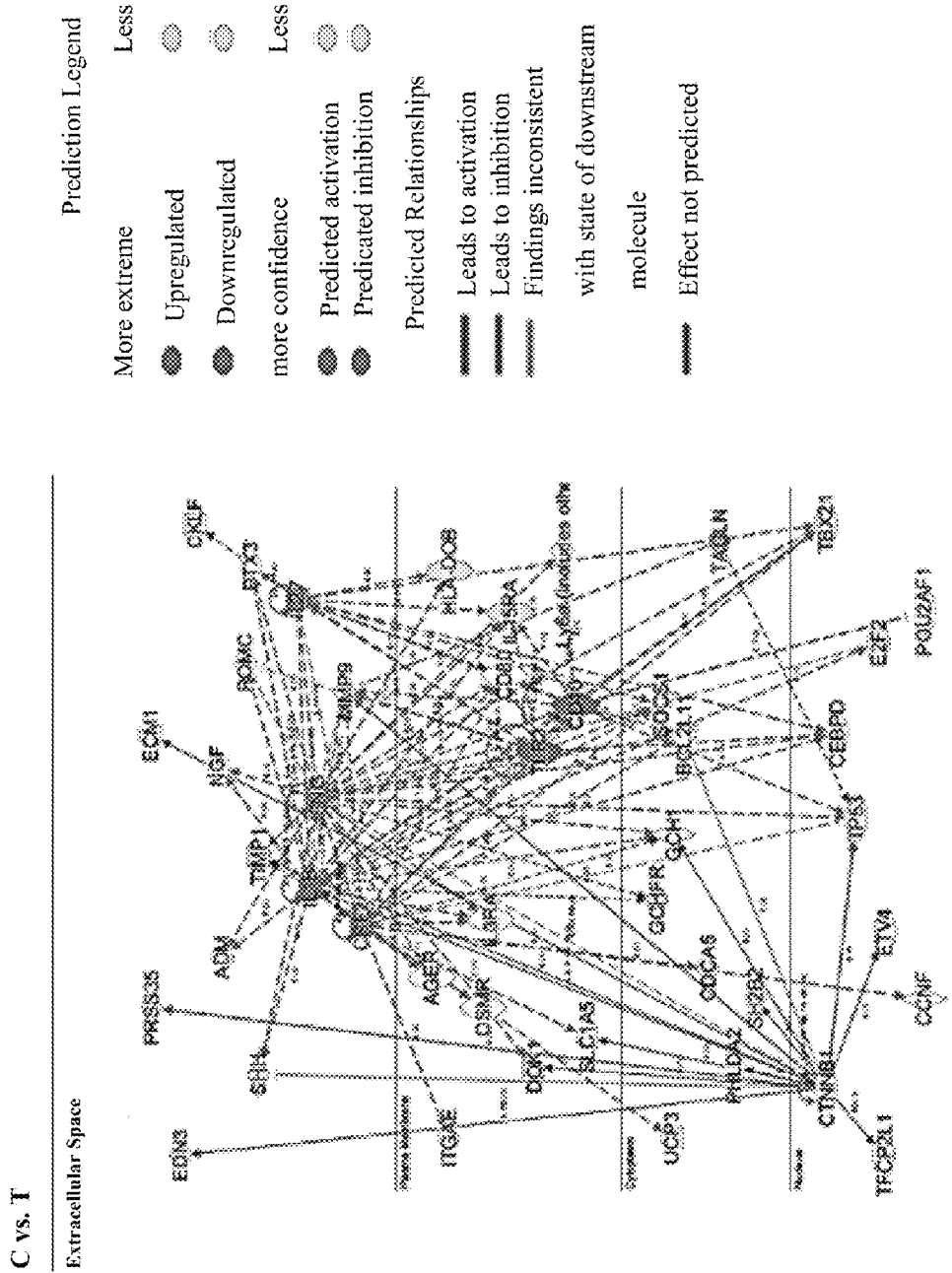
FIG. 13 shows upstream nodal regulators for brain. This panel illustrates several of the top predicted upstream nodal regulators for brain from the IPA analysis of the genes for the +1 pattern. On the left C vs T, the upstream regulators IL1β, IFNG, IL27, CSF2, TLR2, CD40 and CTNNB1 are illustrated along with the gene expression driving their predicted upregulation. As you can see there is significant overlap in the gene expression driving these upstream regulators. The gene expression patterning is shown with cellular location, thus you can see the relationship between the nuclear transcription factors that are driving expression of targets that impact inflammation and cellular proliferation. On the right side of the panel, C vs TE, is an illustration of how gene expression in these networks changes with exosome treatment. All of the inflammation related regulators move from a predicted activation depicted by the orange color on the left panel to no change from control as indicated by the lack of color in the right panel. A number of the genes driving these changes such as MMP9, TIMP1, POMC, and PTX3 which show upregulation following TBI (red) show downregulation (green) following treatment with exosomes. This shows a powerful modulation of many of the gene expression patterns following exosome treatment. Not shown is the pattern for treatment with exosomes depleted of MALAT1 as this gene expression network is almost identical to that observed on the left with TBI treatment alone. The legend inserted on the top right describes the meaning of the various color assignments.

Brain mRNA Changes:

For the pattern +1 the several of the predominant predicted upstream nodal regulators from the IPA analysis are related to inflammatory pathways, IL1β, IFNG, etc. which is in agreement with the literature on TBI alone. To illustrate this graphically, FIG. 13 shows top upstream regulatory networks in the C vs T comparison. There is a strong predicted upstream activation of inflammatory regulators such as IL1β, IFNG, TLR2, IL27 and CD40 (indicated in orange). Also illustrated in this figure are the actual gene expression changes driving the predictions, which show significant overlap in the nodal networks depicted. Furthermore, CTF1 was also predicted to be an upstream regulator by this analysis, which is consistent with its role in other brain injury models and inflammation. In addition, there were changes in CTNNB1: the gene for beta catenin which is a regulator for the WNT pathway. WNT is known to be involved in neural repair pathways and neurogenesis, and is also related to SOX15 which is discussed further below. This pathway is downregulated with TBI and the extent of down regulation is lessened following treatment with exosomes as reflected in the color of the regulator moving from a darker orange to a lighter color. The right side of the figure illustrates the overlay of the pattern of gene expression and predictions for the nodal regulation in the TBI treated with exosomes group. All of the inflammatory nodes such as IL1β, IFNG, CD40 and IL27 show no predicted upregulation from controlled which is indicated by lack of color, demonstrating that the exosomes significantly lower the pro-inflammatory gene expression patterns observed with injury. This is driven by decreased gene expression of pro-inflammatory genes PTX3, MMP9, POMC, and CD80 in this dataset which is shown by the green color. Not shown in this figure is the network of these upstream regulators for the third aspect of this pattern which is C vs. TdM comparison, when exosomes depleted in MALAT1 are given after TBI the network of gene expression and predicted upstream regulators is an almost identical pattern to the C vs. T network shown here. This is in agreement with the pattern of behavioral and histological changes presented above.

The predicted upstream regulators for the pattern −1 with gene expression going down with TBI are related to transcription regulators such as SOX15, RFX3, TCF7L1 as well as ubiquitin and HSP70 (FIG. 20 different functional groups depicted by colors). This suggests that there is a decline in transcriptional activation in regenerative pathways as illustrated by changes in SOX15 expression, which is part of the WNT/β-catenin pathway involved in cellular proliferation and stem cell proliferation.

For canonical pathways identified, the +1 pattern shows the highest p value of overlap with no significant canonical pathways identified in the brain for the −1 pattern. Canonical pathways that are increased with TBI and responsive to the exosome treatment also include inflammatory pathways. Cell cycle and cancer related pathways are further noted, most likely changing due to cell death and injury caused by CCI (Table 1).

Spleen mRNA Expression:

Gene expression in the spleen was also examined, as the data shows predominant localization of exosomes to spleen. The data shows the presence of exosomes in the spleen at an early time point following injection, prior to the exosomes being observed in the brain. FIG. 20 shows the top ranking predicted upstream regulators based upon p-value of overlap, and if there was a significant Z score for predicted activation or inhibition. For the +1 pattern of expression that increases with TBI, there was a predicted inhibition of CDKN1A suggesting a decrease in cellular proliferation. This is supported by changes in other proliferation related pathways like CCND1 which is a cell cycle regulator related to both AMPK and PTEN bioenergetics pathways as well as inflammation pathways like IL8 and ILK. Many of the predicted upstream regulators are nuclear transcription factors influencing many aspects of cellular function including cellular proliferation, cell cycle control and well as DNA damage. This again is likely a reflection of the response to the brain injury effecting other organ systems.

Figure 14:
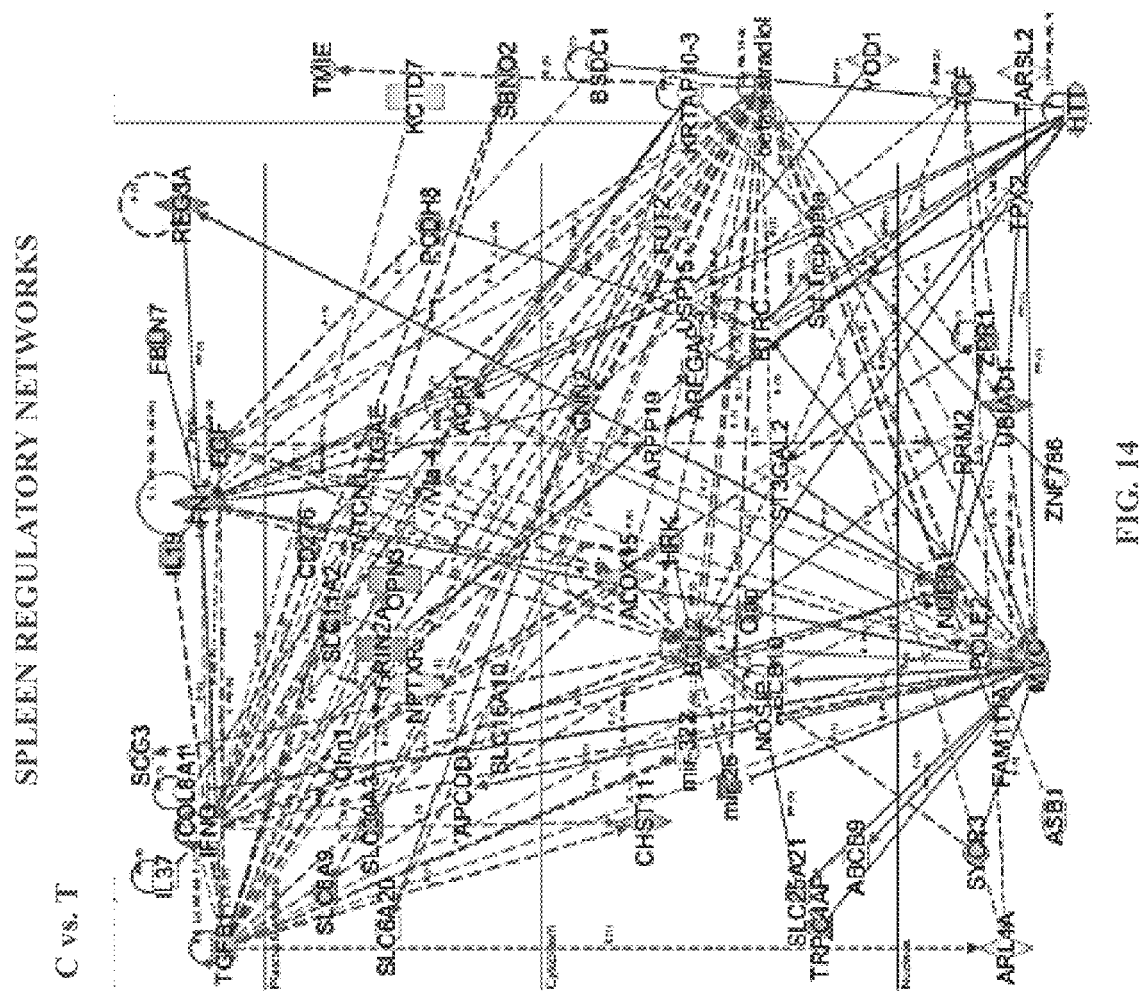
FIG. 14 shows spleen Regulatory Networks. Gene networks altered by TBI in the spleen are depicted in this figure. On the left C vs T, is the gene expression in these networks when comparing control and TBI gene expression showing activation of inflammatory pathways TGFB1, IL19, IL37. BCL2 is activated, likely in response to the impact of the brain injury as a compensatory process in the spleen. NUPR1 is a transcriptional cofactor involved in apoptosis and is reciprocally inhibited by TBI. In the right panel C vs TE, it is shown that exosome treatment returns NUPR1 expression back towards control levels. Also of interest is a predicted regulation of these networks by beta-estradiol activation following TBI, which is inhibited following exosome treatment. A number of genes related to this pathway are the inflammatory changes and also mir-322 which is responsive to hypoxia and oxidative stress. Beta estradiol is known to play a role in splenic response to injury by modulating macrophage and dendritic cell function.

To explore the regulatory networks of genes affected in the spleen in response to the +1 pattern of expression, two of the top networks identified in IPA were merged and this is illustrated in FIG. 14. The left panel shows these network changes along with predicted nodes in addition to relationships with canonical pathways. Again, as in the brain, a number of inflammation-related pathways including TGFβ and INFG are altered with TBI. Also shown are a number of the changes to pathways related to the transcriptional regulators MYC and NUPPR1. The predicted inhibition of NUPPR1 with TBI is mitigated with the exosome treatment as shown in the right panel and might be related to an increase in POLE2 in the exosome treated group. Also of interest is a predicted regulation of these networks by beta-estradiol activation following TBI which is inhibited following exosome treatment (FIG. 14). A number of genes related to this pathway are involved in inflammatory responses and cellular stress, such as mir-322 which is responsive to hypoxia and oxidative stress. Beta estradiol is known to play a role in splenic response to injury by modulating macrophage and dendritic cell function, thus are consistent with effects of estradiol in other injury models. It is important to note that this does not necessarily mean that estradiol is driving this alteration in the dataset, it simply means that estradiol alters splenic inflammatory markers in the same way as what is observed in the dataset. Several investigations have suggested that estradiol reduces MALAT1, thus a predicted inhibition of estradiol by exosome treatment may reflect increased action of MALAT1. Further studies are needed to elucidate an interaction of exosome treatment with estradiol.

The expression of genes in the −1 pattern demonstrated inhibition of several aspects of splenic function including the ephrins A2, 3, 4, and 5, which regulate interaction with hematopoiesis. While these processes are more related to ephrin A1, for this study ephrin A2 is of particular interest as it plays a role in monocyte adhesion and transendothelial migration via integrins. Increase in ephrin A2 has been reported to stimulate monocyte infiltration and sequestration into the red pulp of the spleen via an interaction with integrin and additional undetermined molecular pathways. The release of monocytes from the red pulp of the spleen is a known consequence of injury. Therefore, inhibition of ephrin A2 would be consistent with release of monocytes from the splenic red pulp into the bloodstream. As presented, this predicted loss of the inhibition of ephrins is seen following treatment with exosomes, but treatment with exosomes depleted of MALAT1 showed similar results to those observed with rats that received TBI with no treatment. This is a potentially interesting finding, and although at this point a direct correlation between this predicted change in ephrin A2 regulation following TBI and treatment with exosomes cannot be made, it is consistent with the observed behavioral and histological improvement with the exosome treatment. As previously discussed, one possible role of the spleen in TBI and other brain insults is the release of monocytes into circulation then participate in the secondary insult at the site of injury.

TABLE 1

| Canonical Pathways |
|---|
| Brain Pattern 1 |
| Pancreatic Adenocarcinoma Signaling |
| Role of CHK Proteins in Cell Cycle Checkpoint Control |
| T Helper Cell Differentiation |
| Cyclins and Cell Cycle Regulation |
| Th1 Pathway |
| Bladder Cancer Signaling |
| Inhibition of Angiogenesis by TSP1 |
| Dopamine Receptor Signaling |
| ILK Signaling |
| B Cell Development |
| Cell Cycle Regulation by BTG Family Proteins |
| Inhibition of Matrix Metalloproteases |
| Thyroid Cancer Signaling |
| HIF1α Signaling |
| Crosstalk between Dendritic Cells and Natural Killer Cells |
| Th1 and Th2 Activation Pathway |

TABLE 1-continued

Canonical Pathways

Role of JAK family kinases in IL-6-type Cytokine Signaling
Role of JAK1 and JAK3 in γc Cytokine Signaling
Role of Oct. 4 in Mammalian Embryonic Stem Cell Pluripotency
Autoimmune Thyroid Disease Signaling

Spleen

| Pattern 1 | Pattern -1 |
| --- | --- |
| Heme Biosynthesis II | cAMP-mediated signaling |
| Mitotic Roles of Polo-Like Kinase | G-Protein Coupled Receptor Signaling |
| Heme Biosynthesis from Uroporphyrinogen-III I | Serine Biosynthesis |
| Tetrapyrrole Biosynthesis II | Superpathway of Serine and Glycine Biosynthesis I |
| Estrogen-mediated S-phase Entry | LPS/IL-1 Mediated Inhibition of RXR Function |
| GADD45 Signaling | Protein Kinase A Signaling |
| Cell Cycle: G2/M DNA Damage Checkpoint Regulation | Cardiac Hypertrophy Signaling |
| Cyclins and Cell Cycle Regulation | Fatty Acid Activation |
| dTMP De Novo Biosynthesis | nNOS Signaling in Skeletal Muscle Cells |
| Cell Cycle Control of Chromosomal Replication | Corticotropin Releasing Hormone Signaling |
| DNA damage-induced 14-3-3σ Signaling | |
| Rapoport-Luebering Glycolytic Shunt | |
| Pyrimidine Deoxyribonucleotides De Novo Biosynthesis I | |
| ATM Signaling | |
| Antiproliferative Role of TOB in T Cell Signaling | |
| Role of CHK Proteins in Cell Cycle Checkpoint Control | |
| Cell Cycle: G1/S Checkpoint Regulation | |
| Cell Cycle Regulation by BTG Family Proteins | |
| Asparagine Biosynthesis I | |
| γ-glutamyl Cycle | |

Example 16: Validation of RNA Seq Results of Gene Expression

Confocal microscopy confirmed positive localization of GFP labelled exosomes within both the contralateral and ipsilateral brain regions as well as in the spleen (FIGS. 15A-F). The GFP signal was more robust in the ipsilateral hemisphere compared to the contralateral, and it was located mainly in close proximity to the impacted area. This may be the result of a breakdown of the blood brain barrier at the site of injury. It was next valided that exosomes were taken by the brain and spleen. RNA isolated from either brain or spleen was reverse transcribed to cDNA and used in quantitative SYBR Green real time qPCR using primers for rat and human MALAT1. Results show that endogenous rat MALAT1 is depleted in spleen and the cortex near the injury site following injury and increased with exosomes treatment. Further, exosomes not depleted of MALAT1 were shown to deliver human MALAT1 to the brain and spleen (FIG. 15G-H). These results show that exosomes are efficiently taken by the brain and spleen.

To validate results from RNA Seq, real-time qPCR was used to determine levels of the top genes from altered in spleen and brain following TBI and TBI with exosomes treatment. FIGS. 16A-I show validation of spleen expression of PLAg2, TNFα, E2F4 and RABL6 and brain cortex expression of IL1β, TNFα, IFNG and IL10. These genes showed significant fold changes in RNA Seq data and are components of the predicted networks. Although the pattern of expression for IL10 is not consistent with the overall predicted changes in inflammatory networks, it does replicate the data in the RNA Seq dataset. The qPCR results show expression of these genes that are in agreement with the RNA Seq data.

Example 17: Noncoding RNA Levels Change with Injury and Exosome Treatment in a MALAT1 Dependent Manner Long noncoding RNAs promote epigenetic modifications and regulate gene expression by direct interaction with pre-mRNA of genes or by acting as scaffolding to tether a complex of micro RNAs to promote transcription of genes. There is an emerging appreciation for its ability to not only interact with other noncoding RNAs but also promote transcription of these noncoding RNAs. Amongst the noncoding RNAs (ncRNAs) detected in the brain and spleen, a large number are associated with tRNA, rRNA and small nuclear RNAs (snRNAs) whose function is constitutive in transcription and translation processes. This study points to two primary classes of ncRNAs that are directly affected by the lncRNA exosomes containing MALAT1: The microRNAs (miR) and the small nucleolar RNAs (snoRNAs).

miRNAs regulate gene expression by directly binding to their target mRNA. The RNA-seq data presented herein identified miR-200b, miR-200a, miR-183, miR-182, miR-96, and miR-451a as being significantly upregulated 4-8 fold in the brain with TBI (Table 2). These miRNAs were previously shown to regulate apoptosis in various diseases. Significantly, treatment with exosomes downregulated their expression; MALAT1 depleted exosomes did not have a significant change in the expression of these miRNAs. When the RNA Seq data of brain is sorted and analyzed by pattern (+1) described above, miR-96-5p, miR-182, miR-183-5p, miR-200b-5p, miR-429, mir-6216, miR-1193-3p and miR-218a-2-3p increase following TBI, decreased by exosome treatment and the reversal is not seen with MALAT1 deficient exosomes. miR200b-3p and miR-182-5p are increased following TBI in the brain, the latter of which is directly modulated by MALAT1. Both of these miRNA's also show a reduction following treatment with exosomes, but not exosomes depleted of MALAT1, opening the possibility that MALAT1 in exosomes may be responsible for the shift in pattern. A second set of miRNAs include miR-487b-3p, miR-672-3p, miR-10a-5p, miR-770-5p, miR-666-5p, miR-29c-3p, miR-139-3p, miR-668, miR-344a-3p, miR1843a-3p that follow the −1 pattern such that they decrease following TBI, increased by exosome treatment and the reversal is not seen with MALAT1 deficient exosomes. Of the miRNAs whose expression changes in the with injury and exosome treatment, miR10a-5p follows −1 pattern in the brain and the spleen. miR10a-5p is extensively studied for its role in development and regulation of TOP mRNAs. miR10a-5p promotes expression of ribosomal proteins, elongation factors and other proteins associated with translation apparatus thereby influencing global protein synthesis. miR10a-5p expression is increased in stem cells and in the disclosed experiments, it is possible that miR10a-5p is part of the exosomal cargo which is transferred both to the brain and spleen and has a predominant role in enhancing the response to injury and aiding the recovery upon treatment with exosomes.

SnoRNAs function as sequence specific guides to direct site-specific nucleoside modifications for other noncoding RNAs such as rRNA and snRNA. A select few snoRNAs are shown to interact with mRNA and regulate its splicing. Recent breakthroughs have predicted the interaction of lncRNAs with snoRNAs; however their association are not shown in vivo. SnoRNAs are transcribed as nuclease products from genes. The data shows, for the first time, that a long noncoding RNA MALAT1 regulates the expression of snoRNAs in the brain. Notably, SNORA31, SNORD33, SNORD64, SNORA18, SNORA17, SNORD44, SNORD47, SNORD28, SNORD113, SNORD62, SNORA29, SNORD2 were upregulated 2-4 fold with exosome treatment following TBI; MALAT1 depleted exosomes did not increase the levels of these snoRNAs (Table 2). Brain specific snoRNAs in mice MBI48 and MBI52 were shown to promote memory and learning. While lncRNAs are known to have a role in pre-mRNA splicing, mRNA editing, mRNA stability control, this is the first evidence showing that lncRNA MALAT1 regulating the expression and transcription of brain snoRNAs.

TABLE 2

| | | | | | | | |
|---|---|---|---|---|---|---|---|
| Changes in noncoding RNA miRNA | | | | | | | |
| | C vs T | C vs TE | C vs TEdM | | C vs T | C vs TE | C vs TEdM |
| Brain +1 | | | | Spleen +1 | | | |
| rno-miR-429 | 346.52 | 26.50 | 208.76 | rno-miR-451-3p | 3.70 | −1.15 | 4.82 |
| rno-miR-200b-5p | 99.01 | 7.42 | 127.07 | rno-miR-1949 | 1.78 | −1.05 | 1.45 |
| rno-miR-183-5p | 59.14 | 6.56 | 122.37 | rno-miR-6216 | 1.38 | −1.22 | 1.30 |
| rno-miR-182 | 56.38 | 1.00 | 43.57 | rno-miR-17-5p | 1.51 | −1.13 | 1.52 |
| rno-miR-96-5p | 48.13 | 1.00 | 61.72 | rno-miR-144-5p | 3.85 | 2.01 | 4.19 |
| rno-miR-6216 | 2.67 | −1.04 | 2.82 | rno-miR-484 | 1.52 | −1.10 | 1.88 |
| rno-miR-1193-3p | 1.34 | 1.03 | 1.20 | rno-miR-132-3p | 2.07 | 1.01 | 1.83 |
| rno-miR-218a-2-3p | 1.24 | 1.07 | 1.30 | rno-miR-702-3p | 4.89 | 2.44 | 3.59 |
| | | | | rno-miR-409a-5p | 1.85 | 1.04 | 1.84 |
| | | | | rno-miR-92a-3p | 1.33 | −1.08 | 1.29 |
| | | | | rno-miR-339-5p | 1.39 | −1.07 | 1.30 |
| | | | | rno-miR-93-5p | 1.53 | 1.07 | 1.74 |
| | | | | rno-miR-361-5p | 1.30 | −1.01 | 1.50 |
| | | | | rno-miR-31a-5p | 1.18 | −1.13 | 1.30 |
| | | | | rno-miR-21-3p | 1.29 | −1.07 | 1.31 |
| | | | | rno-miR-423-5p | 1.19 | −1.10 | 1.26 |
| | | | | rno-miR-210-p | 1.35 | 1.11 | 1.45 |
| | | | | rno-miR-532-3p | 1.25 | 1.11 | 1.26 |
| | | | | rno-miR-103-3p | 1.18 | −1.01 | 1.24 |
| | | | | rno-miR-6319 | 1.39 | 1.12 | 1.27 |
| | | | | rno-miR-378a-5p | 1.10 | 1.05 | 1.17 |
| | | | | rno-miR-342-3p | 1.06 | −1.05 | 1.09 |
| Brain −1 | | | | Spleen −1 | | | |
| rno-miR-154-5p | −1.48 | −1.17 | −1.32 | rno-miR-708-3p | −10.9 | 1.69 | −1.39 |
| rno-miR-7b | −1.65 | −1.04 | −1.80 | rno-miR-6329 | −3.33 | −1.07 | −1.57 |
| rno-miR-665 | −2.57 | −1.11 | −1.69 | rno-miR-148b-5p | −1.22 | 1.14 | −1.10 |
| rno-miR-487b-3p | −1.38 | 1.32 | −1.54 | rno-miR-212-5p | −1.44 | −1.09 | −2.17 |
| rno-miR-672-3p | −1.77 | 1.09 | −1.41 | rno-miR-181a-1-3p | −1.55 | 1.23 | −1.16 |
| rno-miR-10a-5p | −1.47 | 1.29 | −1.29 | rno-miR-1843b-5p | −1.79 | 1.07 | −1.37 |
| rno-miR-770-5p | −1.53 | 1.12 | −1.60 | rno-miR-10a-5p | −1.49 | 1.16 | −1.22 |
| rno-miR-666-5p | −1.29 | 1.24 | −1.32 | rno-miR-379-5p | −1.92 | −1.01 | −1.32 |
| rno-miR-29c-3p | −1.52 | 1.07 | −1.22 | rno-miR-411-5p | −1.66 | −1.12 | −2.09 |
| rno-miR-3594-3p | −1.61 | −1.04 | −1.37 | rno-miR-192-5p | −1.72 | 1.01 | −1.80 |
| rno-miR-485-3p | −1.41 | −1.13 | −1.32 | rno-let-7f-5p | −1.58 | 1.12 | −1.20 |
| rno-miR-139-3p | −1.45 | 1.02 | −1.27 | rno-miR-1 b | −1.53 | 1.14 | −1.37 |
| rno-miR-139-5p | −1.54 | −1.09 | −1.41 | rno-miR-148a-3p | −1.40 | −1.10 | −1.20 |
| rno-miR-668 | −1.19 | 1.12 | −1.20 | rno-miR-126a-5p | −1.46 | 1.09 | −1.47 |
| rno-miR-342-5p | −1.15 | 1.10 | −1.11 | rno-miR-28-5p | −1.39 | 1.08 | −1.30 |
| rno-miR-344a-3p | −1.18 | 1.01 | −1.21 | rno-miR-204-5p | −1.47 | 1.00 | −1.20 |
| rno-miR-330-3p | −1.30 | −1.05 | −1.19 | rno-miR-181c-3p | −1.67 | −1.14 | −1.42 |
| rno-miR-1843a-3p | −1.13 | 1.01 | −1.16 | rno-miR-3068-3p | −1.58 | −1.08 | −1.24 |
| rno-miR-328a-3p | −1.18 | −1.08 | −1.18 | rno-miR-30c-5p | −1.41 | 1.03 | −1.15 |
| | | | | rno-miR-27a-3p | −1.16 | 1.06 | −1.21 |
| | | | | rno-miR-139-5p | −1.33 | −1.07 | −1.24 |
| | | | | rno-miR-140-5p | −1.30 | 1.06 | −1.25 |

TABLE 2-continued

| Changes in noncoding RNA miRNA | | | |
|---|---|---|---|
| rno-miR-337-5p | −1.42 | −1.05 | −1.34 |
| rno-miR-30a-5p | −1.16 | 1.03 | −1.08 |
| rno-miR-150-5p | −1.29 | −1.10 | −1.16 |
| rno-miR-147 | −1.12 | 1.04 | −1.09 |
| rno-miR-30e-5p | −1.24 | −1.08 | −1.14 |

| ncRNA including snoRNA, snRNA | | | | | | | | |
|---|---|---|---|---|---|---|---|---|
| | | C vs T | C vs TE | C vs TEdM | | | C vs T | C vs TE | C vs TEdM |

| Brain +1 | | | | | Brain −1 | | | | |
|---|---|---|---|---|---|---|---|---|---|
| snRNA | U6 | 1.57 | 1.00 | 1.37 | snoRNA | SNORD42 | −1.90 | −1.24 | −1.82 |
| snoRNA | SNORD24 | 1.28 | 1.11 | 1.38 | lncRNA | PVT1 3 | −1.98 | −1.34 | −2.18 |
| snoRNA | SNORD60 | 1.25 | 1.00 | 1.22 | snoRNA | SNORA28 | −1.29 | −1.07 | −1.97 |
| snRNA | U6 | 1.09 | 1.00 | 1.06 | rRNA | Rnr2 | −1.25 | −1.07 | −1.23 |
| snoRNA | ACEA U3 | 1.64 | 1.05 | 1.59 | rRNA | Rnr2 | −1.09 | −1.10 | −1.29 |
| snoRNA | SNORA62 | 1.51 | −1.04 | 1.27 | lncRNA | RMST 2 | −1.19 | −1.06 | −1.13 |
| snoRNA | SNORA73 | 1.39 | −1.24 | 1.30 | | | | | |
| snoRNA | SNORD62 | 1.76 | −1.21 | 1.32 | | | | | |
| snoRNA | SNORD15 | 3.17 | −1.38 | 3.12 | | | | | |
| snoRNA | SNORA38 | 1.06 | 1.00 | 1.06 | | | | | |

| Spleen +1 | | | | | Spleen −1 | | | | |
|---|---|---|---|---|---|---|---|---|---|
| snoRNA | SNORD74 | 1.85 | −1.39 | 1.52 | snoRNA | SNORA41 | −3.84 | −1.14 | −1.85 |
| snRNA | U6 | 1.67 | −1.27 | 1.67 | snoRNA | SNORD33 | −3.68 | −1.64 | −3.91 |
| snoRNA | SNORD75 | 1.68 | −1.03 | 1.50 | snoRNA | SNORA54 | −3.49 | 1.06 | −1.98 |
| scRNA | | 1.32 | −1.23 | 1.14 | snoRNA | SNORD21 | −3.48 | −1.48 | −3.88 |
| lncRNA | LOC100909539 | 1.37 | −1.06 | 1.48 | snoRNA | SNORA71 | −2.94 | −1.55 | −3.67 |
| misc_RNA | | 1.31 | 1.10 | 1.42 | vault_RNA | Vault | −2.93 | −1.49 | −5.34 |
| lncRNA | Bc1 | 1.15 | 1.04 | 1.25 | snoRNA | SNORA11 | −2.71 | −1.08 | −2.24 |

Example 18: Discussion

In summary, exosomes secreted from hASC's have a beneficial role in modulating pathology following mild TBI, particularly those containing MALA1. The results presented herein show an attenuation in TBI-induced motor deficits as well as decreased cortical damage at both the impact and peri-impact level after administration of exosome treatment, which is dependent on MALAT1. MALAT1 has a role in neuroprotection in vitro, and hASC exosomes increase neuronal survival and proliferation in vitro after several models of injury and this activity is lost when the exosomes are depleted of MALAT1. These results suggest that intravenous administration of exosomes generated from hASC's may represent a novel therapeutic approach for treatment of TBI. To distinguish the actions of subcomponents of conditioned media, rats were treated with CM that did not contain exosomes. This treatment had a reduced effect on most measures when compared to exosome treatment. However, there was still some effect seen from CM depleted of exosomes. The difference between the exosome treatment compared to the CM depleted of the exosomes suggests the importance of the cargo found in the exosomes for providing significant neuroprotection and regeneration after injury; and secondly, the effect provided by the CM depleted of the exosomes, though not significantly different from vehicle treatment, still suggests the possibility that the CM depleted of exosomes maintains valuable secreted factors.

Exosomes are known to hold a plethora of biological molecules in its complex cargo including proteins, lipids, mRNAs and miRNAs capable of interacting with surrounding cells in order to modify the host environment. Exosomes generated from MSCs have been shown to significantly increase brain angiogenesis and neurogenesis as well as reduce neuroinflammation, however, the specific molecular constituents driving regeneration were not identified in most studies. It is thought that RNA cargo plays a role in the cell-to-cell communication driving neuroprotection making it a key component promoting the recovery seen following injury. This study demonstrates that lncRNA MALAT1 is a critical component of the hASC exosomes and drives the recovery process. Many single molecular pathway approaches have shown little or no promise in clinical trials, and this emphasizes a need for combination therapies to tackle the complexity of secondary neurological injury post TBI. Treatment with exosomes is considered to be a multi-targeted approach, as they are able to seek and modulate multiple targets and enforce a neuroprotective environment, providing further promise for their use as a therapeutic approach.

In this study, it is demonstrated for the first time the in vivo and ex vivo biodistribution of intravenous DIR-labeled exosomes derived from hASCs. It is well known that when administering cell therapy intravenously, the cells migrate to multiple organs and here exosomes are shown to migrate to the same organ sites, with some differences in time course and degree of migration. The exosomes are observed in the spleen and liver area when observed both in vivo and ex vivo within one hour of IV treatment followed by a decrease in radiance efficiencies over time. Though migration to the liver probably serves as a filtering and elimination technique, the migration of the exosomes to the spleen implicates a probable immune interaction. It has been shown that injury induces the release of immune cells from the spleen with consequent infiltration into the brain and that this is a significant aspect of the secondary insult following TBI. It has been shown that blocking entry of inflammatory monocytes into the brain can significantly reduce the observed damage and offers recovery of cognitive function. The spleen is one source of peripheral macrophages and monocytes, and it is possible that the exosome treatment inhibits the release of these immune cells into circulation. This in turn lessens the infiltration into the brain through the disrupted BBB and prevents the contribution of peripheral immune cells to the secondary injury. This was supported by the observed inhibition of ephrin family gene expression following TBI as a predicted upstream regulator in the spleen following injury. This inhibition was modulated by exosome treatment but not by treatment with exosomes depleted of MALAT1. Ephrins are regulators of transendothelial migration of monocyte/macrophages and have been shown to play a role in monocyte adhesion in the red pulp of the spleen. Thus a decrease with TBI could be reflective of a migration of monocytes into the circulation. Therefore, the observed migration of the exosomes to the spleen immediately after administration could be an aspect of the mechanism of action that elicits the improvement in both cellular and functional recovery as seen here post TBI. Future studies can look deeper into this potential mechanism of action and the role of MALAT1 in this action at the level of the spleen.

Exosomes were also observed in the brain, albeit with a much lower degree of signal and with a different time course than that observed for the spleen. Exosomes were primarily observed around the site of injury. The blood-brain barrier is known to be disrupted by the injury, peaking at 4-6 hours and 2-3 days after TBI injury, and therefore this may explain one factor for the observed delayed localization of exosomes. Alternatively, it is also possible that there is expression of chemokine or signaling molecules that would attract the exosomes to the area of injury. Furthermore, at this time it is not known if the primary site for the therapeutic effect of the exosomes is the level of the spleen or the brain, it is likely that both play some role. It has been shown that hASC-derived exosomes as those studied here have direct neuroprotective effect on neuronal cells and this is another area of future investigation.

RNASeq is a robust method to evaluate the effect of TBI at the genomic level. This study identifies genes and pathways that are affected by TBI as well as the genomic influences of exosome treatment. Taken together, it is demonstrated that treatment with exosomes post TBI significantly improves the outcome by modulating gene networks. The knowledge of specific genes and pathways as well as the influence of noncoding RNA in exosome treatment post-TBI is crucial to develop an understanding of the multitude of events that occur simultaneously to promote healing. The data indicates that not only genes involved in survival are affected but also those genes that are involved in the inflammatory and immune response to injury. The cargo carried by the exosomes is pivotal in cell-cell communication and influences the response to injury and recovery. Exosomes from hASC contain not only lncRNA MALAT1 but also additional lncRNAs and proteins. This study specifically focused on the role of MALAT1, however, as shown in the data, other ncRNAs or proteins carried in the exosomes may also aid in the recovery process.

The above results demonstrate that the lncRNA MALAT1 regulates expression of mRNA and ncRNA involved in the inflammatory response, apoptosis and cell survival, signal transduction by MAPK pathways and transcription of genes. There is also an emerging appreciation for its ability to not only interact with other ncRNAs but also promote transcription of these ncRNAs. This disclosure demonstrates for the first time that a lncRNA promotes expression of snoRNAs. The data presented herein contains a tremendous amount of information on novel and known genes in the brain and spleen that were not previously recognized. This RNASeq data provides a valuable tool to elucidate additional genes and ncRNAs in the brain and spleen and provides a robust biological system to validate its findings.

Taken together, the data demonstrate that hASC-derived exosomes containing MALAT1 have a beneficial effect on function and pathology following a CCI injury. It is shown that the lncRNA MALAT1 affects not only mRNA expression by also expression of noncoding RNA. Thus, the action of the exosomes is multifold and impacts a number of cell survival, inflammatory, and regulatory pathways in both the spleen and the brain. As exosomes show tremendous promise as therapeutics, understanding the importance of the cargo of the exosomes is critical for understanding their mechanism of action as well as determining how to identify the exosomes with the most potential for benefit.

Example 19: Intranasal Delivery of Exosomes Post-TBI

Mild controlled cortical impact (CCI) was repeated in C57Bl/6 mice (n=12) and hASC exosomes were administered intranasally. The hASC cells were transfected with GFP (Nucleofector 4D, Lonza) and conditioned media was collected after 48h. Exosomes were isolated and characterized as described above. GFP was incorporated into the exosomes as verified by imaging and quantification on Nexcelom's K2. 10 µg of GFP-labeled hASC exosomes were administered intranasally (4 µl/nostril alternating) 24 hours post injury. 7 days later, RNA was collected from the cortex and real time SYBR Green qPCR was used to verify the presence of human MALAT1 and GFP (delivered by the exosomes) in the brain (FIG. 17)

Intranasal hASC exosomes at 48 hours post injury produce a functional recovery in mice. Intranasal delivery of exosomes is an ideal route of administration to deliver exosomes to the CNS. hASC exosomes were delivered intranasally at 48 hours following CCI in C57Bl/6 mice of 3 months of age. Motor function tests were performed, and showed an impact of the CCI at 24 hours (prior to exosome treatment) that was improved following the delivery of exosomes (FIG. 18A-C). The 6 arm radial arm water maze was also performed at 4 weeks after CCI and shows significant improvement by the training block 3 (FIG. 18D). With 6 arms, the CCI mice eventually learn the placement of the hidden platform.

Where exosomes go after intranasal delivery was examined. At 48 hours after TBI, the location of the GFP label was determined to locate exosomes. Exosomes show migration to the site of injury. They are observed inside neurons and microglia, but not astrocytes (FIG. 19A-C).

For reasons of completeness, various aspects of the invention are set out in the following numbered clauses:

Clause 1: A method of treating brain injury in a subject, the method comprising administering to the subject a composition comprising exosomes isolated from human adipose-derived stem cells (hASC).

Clause 2: The method of clause 1, wherein the composition further comprises insulin.

Clause 3: The method of clause 1, wherein the method further comprises administering insulin to the subject.

Clause 4: The method of clause 3, wherein the insulin is administered to the subject separately from the composition comprising exosomes isolated from hASC.

Clause 5: The method of clause 1, where in the subject is a mammal.

Clause 6: The method of clause 5, wherein the subject is a human.

What is claimed is:

1. A method of treating a traumatic brain injury in a subject, the method comprising intranasally or intravenously administering to the subject a composition comprising exosomes isolated from human adipose-derived stem cells (hASCs), wherein the isolated exosomes comprise metastasis associated lung adenocarcinoma transcript 1/nuclear-enriched abundant transcript 2 (MALAT1/NEAT2) long noncoding RNA, and wherein the method of treating a traumatic brain injury results in increased neuronal functioning.

2. The method of claim 1, wherein the composition further comprises insulin.

3. The method of claim 1, wherein the method further comprises administering insulin to the subject.

4. The method of claim 3, wherein the insulin is administered to the subject separately from the composition comprising isolated exosomes.

5. The method of claim 1, wherein the subject is a mammal.

6. The method of claim 1, wherein the subject is a human.

7. The method of claim 1, wherein administering to the subject comprises intravenous administration.

8. The method of claim 1, wherein administering to the subject comprises intranasal administration.

9. The method of claim 1, wherein the traumatic brain injury comprises a diffuse axonal injury, a concussion, a contusion, a coup-countrecoup injury, a recurrent traumatic brain injury, combinations thereof.

10. The method of claim 1, wherein the treating of a traumatic brain injury results in increased proliferation and survival of neurons.

11. The method of claim 1, wherein the treating of a traumatic brain injury results in increased motor function.

12. The method of claim 1, wherein the treating of a traumatic brain injury results in decreased cortical lesion volume.

* * * * *

UNITED STATES PATENT AND TRADEMARK OFFICE
CERTIFICATE OF CORRECTION

PATENT NO. : 10,857,187 B2
APPLICATION NO. : 16/011239
DATED : December 8, 2020
INVENTOR(S) : Niketa A. Patel and Paula Cole Bickford Page 1 of 1

It is certified that error appears in the above-identified patent and that said Letters Patent is hereby corrected as shown below:

On the Title Page

Column 2 (other publications), Line 7, please delete "PKōll" and insert -- PKCδII --, therefor.

In the Claims

Column 46, Line 8 (approx.), In Claim 9, please delete "countercoup" and insert -- contrecoup --, therefor.

Column 46, Line 9 (approx.), In Claim 9, before "combinations" insert -- or --.

Signed and Sealed this
Twenty-seventh Day of April, 2021

Drew Hirshfeld
*Performing the Functions and Duties of the*
*Under Secretary of Commerce for Intellectual Property and*
*Director of the United States Patent and Trademark Office*

SEQUENCE LISTING

<160> NUMBER OF SEQ ID NOS: 12

<210> SEQ ID NO 1
<211> LENGTH: 22
<212> TYPE: DNA
<213> ORGANISM: Artificial Sequence
<220> FEATURE:
<223> OTHER INFORMATION: Synthetic

<400> SEQUENCE: 1
acatcctaga caacaacggg ac                                              22

<210> SEQ ID NO 2
<211> LENGTH: 21
<212> TYPE: DNA
<213> ORGANISM: Artificial Sequence
<220> FEATURE:
<223> OTHER INFORMATION: Synthetic

<400> SEQUENCE: 2
accacgtcct tcttcagaca c                                               21

<210> SEQ ID NO 3
<211> LENGTH: 21
<212> TYPE: DNA
<213> ORGANISM: Artificial Sequence
<220> FEATURE:
<223> OTHER INFORMATION: Synthetic

<400> SEQUENCE: 3
caccatcttc cagaaagaac g                                               21

<210> SEQ ID NO 4
<211> LENGTH: 26
<212> TYPE: DNA
<213> ORGANISM: Artificial Sequence
<220> FEATURE:
<223> OTHER INFORMATION: Synthetic

<400> SEQUENCE: 4
tcgcaggtct cactactgcc ttttcc                                          26

<210> SEQ ID NO 5
<211> LENGTH: 21
<212> TYPE: DNA
<213> ORGANISM: Artificial Sequence
<220> FEATURE:
<223> OTHER INFORMATION: Synthetic

<400> SEQUENCE: 5
tgacgtgccg cctggagaaa c                                               21

<210> SEQ ID NO 6
<211> LENGTH: 21
<212> TYPE: DNA
<213> ORGANISM: Artificial Sequence
<220> FEATURE:
<223> OTHER INFORMATION: Synthetic

<400> SEQUENCE: 6
ccggcatcga aggtggaaga g                                               21

<210> SEQ ID NO 7
<211> LENGTH: 28
<212> TYPE: DNA
<213> ORGANISM: Artificial Sequence

```
<220> FEATURE:
<223> OTHER INFORMATION: Synthetic

<400> SEQUENCE: 7
gagttctaat tcttttact gctcaatc                                           28

<210> SEQ ID NO 8
<211> LENGTH: 20
<212> TYPE: DNA
<213> ORGANISM: Artificial Sequence
<220> FEATURE:
<223> OTHER INFORMATION: Synthetic

<400> SEQUENCE: 8
tcaagtgcca gcagacagca                                                   20

<210> SEQ ID NO 9
<211> LENGTH: 20
<212> TYPE: DNA
<213> ORGANISM: Artificial Sequence
<220> FEATURE:
<223> OTHER INFORMATION: Synthetic

<400> SEQUENCE: 9
tgcagtgtgc caatgtttcg                                                   20

<210> SEQ ID NO 10
<211> LENGTH: 20
<212> TYPE: DNA
<213> ORGANISM: Artificial Sequence
<220> FEATURE:
<223> OTHER INFORMATION: Synthetic

<400> SEQUENCE: 10
ggccagctgc aaacattcaa                                                   20

<210> SEQ ID NO 11
<211> LENGTH: 23
<212> TYPE: DNA
<213> ORGANISM: Artificial Sequence
<220> FEATURE:
<223> OTHER INFORMATION: Synthetic

<400> SEQUENCE: 11
tcccagggcg aggcttatcc att                                               23

<210> SEQ ID NO 12
<211> LENGTH: 26
<212> TYPE: DNA
<213> ORGANISM: Artificial Sequence
<220> FEATURE:
<223> OTHER INFORMATION: Synthetic

<400> SEQUENCE: 12
gaacgcagtc ccccactacc acaaat                                            26
```